(12) United States Patent
McLean et al.

(10) Patent No.: US 8,216,254 B2
(45) Date of Patent: Jul. 10, 2012

(54) ANCHOR DELIVERY SYSTEM WITH REPLACEABLE CARTRIDGE

(75) Inventors: Matthew McLean, San Francisco, CA (US); Mitchell C. Barham, San Mateo, CA (US); Michael Wei, Redwood City, CA (US); Floria Cheng, San Francisco, CA (US); Andrew L. Johnston, Redwood City, CA (US); Michael Gearhart, Fremont, CA (US); Joseph Catanese, III, San Leandro, CA (US); Theodore C. Lamson, Pleasanton, CA (US); Joshua Makower, Los Altos, CA (US)

(73) Assignee: Neotract, Inc., Pleasanton, CA (US)

( * ) Notice: Subject to any disclaimer, the term of this patent is extended or adjusted under 35 U.S.C. 154(b) by 237 days.

(21) Appl. No.: 12/512,674

(22) Filed: Jul. 30, 2009

(65) Prior Publication Data

US 2010/0030262 A1 Feb. 4, 2010

Related U.S. Application Data

(63) Continuation-in-part of application No. 11/775,162, filed on Jul. 9, 2007, which is a continuation-in-part of application No. 11/671,914, filed on Feb. 6, 2007, now Pat. No. 8,157,815, which is a continuation-in-part of application No. 11/492,690, filed on Jul. 24, 2006, now Pat. No. 7,896,891, which is a continuation-in-part of application No. 11/318,246, filed on Dec. 22, 2005, now Pat. No. 7,645,286, which is a continuation-in-part of application No. 11/134,870, filed on May 20, 2005, now Pat. No. 7,758,594.

(60) Provisional application No. 61/084,937, filed on Jul. 30, 2008.

(51) Int. Cl.
*A61B 17/10* (2006.01)
(52) U.S. Cl. .......... 606/139; 606/144; 606/146
(58) Field of Classification Search .......... 606/139, 606/151, 153, 41, 144–146, 148–150
See application file for complete search history.

(56) References Cited

U.S. PATENT DOCUMENTS

| | | | |
|---|---|---|---|
| 659,422 | A | 10/1900 | Shidler |
| 780,392 | A | 1/1905 | Wanamaker et al. |
| 789,467 | A | 5/1905 | West |
| 2,579,192 | A | 12/1951 | Kohl |
| 2,646,298 | A | 7/1953 | Leary |

(Continued)

FOREIGN PATENT DOCUMENTS

DE 10159470 6/2003

(Continued)

OTHER PUBLICATIONS

S. Kruck, et al., "Aktuelle Therapiemöglichkeiten des Benignen Prostata-Syndroms", J Urol Urogynäkol 2009; 16 (1): 19-22.

(Continued)

*Primary Examiner* — Corrine M McDermott
*Assistant Examiner* — Gregory Anderson
(74) *Attorney, Agent, or Firm* — Steptoe & Johnson LLP

(57) ABSTRACT

A system and associated method for manipulating tissues and anatomical or other structures in medical applications for the purpose of treating diseases or disorders or other purposes. In one aspect, the system includes a delivery device configured to deploy and implant anchor devices for such purposes.

23 Claims, 50 Drawing Sheets

U.S. PATENT DOCUMENTS

| | | |
|---|---|---|
| 2,697,624 A | 12/1954 | Thomas et al. |
| 2,734,299 A | 2/1956 | Masson |
| 2,825,592 A | 3/1958 | Semple |
| 3,326,586 A | 6/1967 | Frost et al. |
| 3,470,834 A | 10/1969 | Bone |
| 3,521,918 A | 7/1970 | Hammond |
| 3,664,345 A | 5/1972 | Dabbs et al. |
| 3,713,680 A | 1/1973 | Pagano |
| 3,716,058 A | 2/1973 | Tanner, Jr. |
| 3,756,638 A | 9/1973 | Stockberger |
| 3,873,140 A | 3/1975 | Bloch |
| 3,875,648 A | 4/1975 | Bone |
| 3,931,667 A | 1/1976 | Merser et al. |
| 3,976,079 A | 8/1976 | Samuels et al. |
| 4,006,747 A | 2/1977 | Kronenthal et al. |
| 4,210,148 A | 7/1980 | Stivala |
| 4,235,238 A | 11/1980 | Ogiu et al. |
| 4,291,698 A | 9/1981 | Fuchs et al. |
| 4,409,974 A | 10/1983 | Freedland |
| 4,493,323 A | 1/1985 | Albright et al. |
| 4,513,746 A | 4/1985 | Aranyi |
| 4,621,640 A | 11/1986 | Mulhollan et al. |
| 4,657,461 A | 4/1987 | Smith |
| 4,669,473 A | 6/1987 | Richards et al. |
| 4,705,040 A | 11/1987 | Mueller et al. |
| 4,714,281 A | 12/1987 | Peck |
| 4,738,255 A | 4/1988 | Goble et al. |
| 4,741,330 A | 5/1988 | Hayhurst |
| 4,744,364 A | 5/1988 | Kensey |
| 4,750,492 A | 6/1988 | Jacobs |
| 4,762,128 A | 8/1988 | Rosenbluth |
| 4,823,794 A | 4/1989 | Pierce |
| 4,899,743 A | 2/1990 | Nicholson et al. |
| 4,926,860 A | 5/1990 | Stice et al. |
| 4,946,468 A | 8/1990 | Li |
| 4,955,913 A | 9/1990 | Robinson |
| 4,968,315 A | 11/1990 | Gatturna et al. |
| 5,002,550 A | 3/1991 | Li |
| 5,041,129 A | 8/1991 | Hayhurst et al. |
| 5,046,513 A | 9/1991 | Gatturna et al. |
| 5,053,046 A | 10/1991 | Janese |
| 5,080,660 A | 1/1992 | Buelna |
| 5,100,421 A | 3/1992 | Christoudias |
| 5,123,914 A | 6/1992 | Cope |
| 5,129,912 A | 7/1992 | Noda et al. |
| 5,192,303 A | 3/1993 | Gatturna et al. |
| 5,203,787 A | 4/1993 | Noblitt et al. |
| 5,217,470 A | 6/1993 | Weston |
| 5,217,486 A | 6/1993 | Rice et al. |
| 5,234,454 A | 8/1993 | Bangs |
| 5,236,445 A | 8/1993 | Hayhurst et al. |
| 5,258,015 A | 11/1993 | Li et al. |
| 5,267,960 A | 12/1993 | Hayman et al. |
| 5,269,809 A | 12/1993 | Hayhurst et al. |
| 5,322,501 A | 6/1994 | Mahmud-Durrani |
| 5,330,488 A | 7/1994 | Goldrath |
| 5,334,200 A | 8/1994 | Johnson |
| 5,336,240 A | 8/1994 | Metzler et al. |
| 5,354,271 A | 10/1994 | Voda |
| 5,358,511 A | 10/1994 | Gatturna et al. |
| 5,364,408 A | 11/1994 | Gordon |
| 5,366,490 A | 11/1994 | Edwards et al. |
| 5,368,599 A | 11/1994 | Hirsch et al. |
| 5,370,646 A | 12/1994 | Reese et al. |
| 5,380,334 A | 1/1995 | Torrie et al. |
| 5,391,182 A | 2/1995 | Chin |
| 5,403,348 A | 4/1995 | Bonutti |
| 5,405,352 A | 4/1995 | Weston |
| 5,411,520 A | 5/1995 | Nash et al. |
| 5,417,691 A | 5/1995 | Hayhurst |
| 5,435,805 A | 7/1995 | Edwards et al. |
| 5,470,337 A | 11/1995 | Moss |
| 5,472,446 A | 12/1995 | de la Torre |
| 5,480,406 A | 1/1996 | Nolan et al. |
| 5,499,994 A | 3/1996 | Tihon et al. |
| 5,501,690 A | 3/1996 | Measamer et al. |
| 5,507,754 A | 4/1996 | Green et al. |
| 5,522,846 A | 6/1996 | Bonutti |
| 5,531,763 A | 7/1996 | Mastri et al. |
| 5,536,240 A | 7/1996 | Edwards et al. |
| 5,540,704 A | 7/1996 | Gordon et al. |
| 5,545,171 A | 8/1996 | Sharkey et al. |
| 5,545,178 A | 8/1996 | Kensey et al. |
| 5,550,172 A | 8/1996 | Regula et al. |
| 5,554,162 A | 9/1996 | DeLange |
| 5,554,171 A | 9/1996 | Gatturna et al. |
| 5,562,689 A | 10/1996 | Green et al. |
| 5,569,305 A | 10/1996 | Bonutti |
| 5,571,104 A | 11/1996 | Li |
| 5,573,540 A | 11/1996 | Yoon |
| 5,578,044 A | 11/1996 | Gordon et al. |
| 5,591,177 A | 1/1997 | Lehrer |
| 5,593,421 A | 1/1997 | Bauer |
| 5,611,515 A | 3/1997 | Benderev et al. |
| 5,626,614 A | 5/1997 | Hart |
| 5,630,824 A | 5/1997 | Hart |
| 5,647,836 A | 7/1997 | Blake, III et al. |
| 5,665,109 A | 9/1997 | Yoon |
| 5,667,486 A | 9/1997 | Mikulich et al. |
| 5,669,917 A | 9/1997 | Sauer et al. |
| 5,690,649 A | 11/1997 | Lehman |
| 5,690,677 A | 11/1997 | Schmiedling et al. |
| 5,697,950 A | 12/1997 | Fucci et al. |
| 5,707,394 A | 1/1998 | Miller et al. |
| 5,716,368 A | 2/1998 | de la Torre et al. |
| 5,718,717 A | 2/1998 | Bonutti |
| 5,725,556 A | 3/1998 | Moser et al. |
| 5,725,557 A | 3/1998 | Gatturna et al. |
| 5,733,306 A | 3/1998 | Bonutti |
| 5,741,276 A | 4/1998 | Poloyko et al. |
| 5,746,753 A | 5/1998 | Sullivan et al. |
| 5,749,846 A | 5/1998 | Edwards et al. |
| 5,752,963 A | 5/1998 | Allard et al. |
| 5,782,862 A | 7/1998 | Bonutti |
| 5,782,864 A | 7/1998 | Lizardi |
| 5,800,445 A | 9/1998 | Ratcliff et al. |
| 5,807,403 A | 9/1998 | Beyer et al. |
| 5,810,848 A | 9/1998 | Hayhurst |
| 5,814,072 A | 9/1998 | Bonutti |
| 5,830,179 A | 11/1998 | Milan et al. |
| 5,830,221 A | 11/1998 | Stein |
| 5,845,645 A | 12/1998 | Bonutti |
| 5,846,254 A | 12/1998 | Schulze et al. |
| 5,861,002 A | 1/1999 | Desai |
| 5,868,762 A | 2/1999 | Cragg et al. |
| 5,873,891 A | 2/1999 | Sohn |
| 5,879,357 A | 3/1999 | Heaton et al. |
| 5,897,574 A | 4/1999 | Bonutti |
| 5,899,911 A | 5/1999 | Carter |
| 5,899,921 A | 5/1999 | Caspari et al. |
| 5,904,679 A | 5/1999 | Clayman |
| 5,904,696 A | 5/1999 | Rosenman |
| 5,908,428 A | 6/1999 | Scirica et al. |
| 5,919,198 A | 7/1999 | Graves, Jr. et al. |
| 5,919,202 A | 7/1999 | Yoon |
| 5,921,982 A * | 7/1999 | Lesh et al. ............ 606/41 |
| 5,921,986 A | 7/1999 | Bonutti |
| 5,928,252 A | 7/1999 | Steadman et al. |
| 5,931,844 A | 8/1999 | Thompson et al. |
| 5,944,739 A | 8/1999 | Zlock et al. |
| 5,948,001 A | 9/1999 | Larsen |
| 5,948,002 A | 9/1999 | Bonutti |
| 5,954,057 A | 9/1999 | Li |
| 5,954,747 A | 9/1999 | Clark |
| 5,964,732 A | 10/1999 | Wilard |
| 5,971,447 A | 10/1999 | Steck, III |
| 6,010,514 A | 1/2000 | Burney et al. |
| 6,011,525 A | 1/2000 | Piole |
| 6,030,393 A | 2/2000 | Corlew |
| 6,033,430 A | 3/2000 | Bonutti |
| 6,036,701 A | 3/2000 | Roseman |
| 6,048,351 A | 4/2000 | Gordon et al. |
| 6,053,908 A | 4/2000 | Crainich et al. |
| 6,056,722 A | 5/2000 | Jayaraman |
| 6,056,772 A | 5/2000 | Bonutti |
| 6,068,648 A | 5/2000 | Cole et al. |
| 6,080,167 A | 6/2000 | Lyell |

| | | | | | | |
|---|---|---|---|---|---|---|
| 6,086,608 | A | 7/2000 | Ek et al. | 6,926,732 B2 | 8/2005 | Derus et al. |
| 6,110,183 | A | 8/2000 | Cope | 6,951,565 B2 | 10/2005 | Keane et al. |
| 6,117,160 | A | 9/2000 | Bonutti | 6,986,775 B2 | 1/2006 | Morales et al. |
| 6,117,161 | A | 9/2000 | Li et al. | 6,991,596 B2 | 1/2006 | Whalen et al. |
| 6,120,539 | A | 9/2000 | Eldridge et al. | 6,991,647 B2 | 1/2006 | Jadhav |
| 6,139,555 | A | 10/2000 | Hart et al. | 6,997,940 B2 | 2/2006 | Bonutti |
| RE36,974 | E | 11/2000 | Bonutti | 7,001,327 B2 | 2/2006 | Whalen et al. |
| 6,143,006 | A | 11/2000 | Chan | 7,011,688 B2 | 3/2006 | Gryska et al. |
| 6,152,935 | A | 11/2000 | Kammerer et al. | 7,015,253 B2 | 3/2006 | Escandon et al. |
| 6,159,234 | A | 12/2000 | Bonutti et al. | 7,048,698 B2 | 5/2006 | Whalen et al. |
| 6,200,329 | B1 | 3/2001 | Fung et al. | 7,048,747 B2 | 5/2006 | Arcia et al. |
| 6,206,895 | B1 | 3/2001 | Levinson | 7,060,077 B2 | 6/2006 | Gordon et al. |
| 6,228,096 | B1 | 5/2001 | Marchand | 7,081,126 B2 | 7/2006 | McDevitt et al. |
| 6,258,124 | B1 | 7/2001 | Darois et al. | 7,083,638 B2 | 8/2006 | Foerster |
| 6,261,302 | B1 | 7/2001 | Voegele et al. | 7,087,073 B2 | 8/2006 | Bonutti |
| 6,270,530 | B1 | 8/2001 | Eldridge et al. | 7,089,064 B2 | 8/2006 | Manker et al. |
| 6,280,460 | B1 | 8/2001 | Bolduc et al. | 7,090,690 B2 | 8/2006 | Foerster et al. |
| 6,290,711 | B1 | 9/2001 | Caspari et al. | 7,093,601 B2 | 8/2006 | Manker et al. |
| 6,312,448 | B1 | 11/2001 | Bonutti | 7,105,004 B2 | 9/2006 | Dicesare et al. |
| 6,319,263 | B1 | 11/2001 | Levinson | 7,108,655 B2 | 9/2006 | Whalen et al. |
| 6,322,112 | B1 | 11/2001 | Duncan | 7,141,038 B2 | 11/2006 | Whalen et al. |
| 6,332,889 | B1 | 12/2001 | Sancoff et al. | 7,153,314 B2 | 12/2006 | Laufer et al. |
| 6,398,795 | B1 | 6/2002 | McAllister et al. | 7,179,225 B2 | 2/2007 | Shluzas |
| 6,425,900 | B1 | 7/2002 | Knodel et al. | 7,226,558 B2 | 6/2007 | Nieman et al. |
| 6,428,562 | B2 | 8/2002 | Bonutti | 7,232,448 B2 | 6/2007 | Battles et al. |
| 6,436,107 | B1 | 8/2002 | Wang et al. | 7,288,063 B2 | 10/2007 | Petros et al. |
| 6,461,355 | B2 | 10/2002 | Svejkovsky et al. | 7,303,108 B2 | 12/2007 | Shelton, IV |
| 6,482,235 | B1 | 11/2002 | Lambrecht et al. | 7,320,701 B2 | 1/2008 | Haut et al. |
| 6,488,691 | B1 | 12/2002 | Carroll et al. | 7,322,974 B2 | 1/2008 | Swoyer et al. |
| 6,491,707 | B2 | 12/2002 | Makower et al. | 7,326,221 B2 | 2/2008 | Sakamoto et al. |
| 6,494,888 | B1 | 12/2002 | Laufer et al. | 7,334,822 B1 | 2/2008 | Hines, Jr. |
| 6,500,195 | B2 | 12/2002 | Bonutti | 7,340,300 B2 | 3/2008 | Christopherson et al. |
| 6,506,190 | B1 | 1/2003 | Walshe | 7,399,304 B2 | 7/2008 | Gambale et al. |
| 6,506,196 | B1 | 1/2003 | Laufer | 7,402,166 B2 | 7/2008 | Feigl |
| 6,517,569 | B2 | 2/2003 | Mikus et al. | 7,416,554 B2 | 8/2008 | Lam et al. |
| 6,527,702 | B2 | 3/2003 | Whalen et al. | 7,417,175 B2 | 8/2008 | Oda et al. |
| 6,527,794 | B1 | 3/2003 | McDevitt et al. | 7,481,771 B2 | 1/2009 | Fonseca et al. |
| 6,530,932 | B1 | 3/2003 | Swayze et al. | 7,553,317 B2 | 6/2009 | Weisenburgh, II et al. |
| 6,533,796 | B1 | 3/2003 | Sauer et al. | 7,608,108 B2 | 10/2009 | Bhatnagar et al. |
| 6,547,725 | B1 | 4/2003 | Paolitto et al. | 7,658,311 B2 | 2/2010 | Boudreaux |
| 6,551,328 | B2 | 4/2003 | Kortenbach | 7,674,275 B2 | 3/2010 | Martin et al. |
| 6,551,333 | B2 | 4/2003 | Kuhns et al. | 7,727,248 B2 | 6/2010 | Smith et al. |
| 6,565,578 | B1 | 5/2003 | Peifer et al. | 2001/0044639 A1 | 11/2001 | Levinson |
| 6,569,187 | B1 | 5/2003 | Bonutti et al. | 2002/0095154 A1 | 7/2002 | Atkinson et al. |
| 6,572,626 | B1 | 6/2003 | Knodel et al. | 2002/0128684 A1 | 9/2002 | Foerster |
| 6,572,635 | B1 | 6/2003 | Bonutti | 2002/0161382 A1 | 10/2002 | Neisz et al. |
| 6,572,653 | B1 | 6/2003 | Simonson | 2002/0193809 A1 | 12/2002 | Meade |
| 6,592,609 | B1 | 7/2003 | Bonutti | 2003/0109769 A1 | 6/2003 | Lowery et al. |
| 6,596,013 | B2 | 7/2003 | Yang et al. | 2003/0191497 A1 | 10/2003 | Cope |
| 6,626,913 | B1 | 9/2003 | McKinnon et al. | 2003/0204195 A1 | 10/2003 | Keane et al. |
| 6,626,916 | B1 | 9/2003 | Yeung et al. | 2003/0236535 A1 | 12/2003 | Onuki et al. |
| 6,626,919 | B1 | 9/2003 | Swanstrom | 2004/0030217 A1 | 2/2004 | Yeung et al. |
| 6,629,534 | B1 | 10/2003 | St. Goar et al. | 2004/0043052 A1 | 3/2004 | Hunter et al. |
| 6,641,592 | B1 | 11/2003 | Sauer et al. | 2004/0078046 A1 | 4/2004 | Barzell et al. |
| 6,656,182 | B1 | 12/2003 | Hayhurst | 2004/0193191 A1 | 9/2004 | Staksen et al. |
| 6,660,023 | B2 | 12/2003 | McDevitt et al. | 2004/0193194 A1 | 9/2004 | Laufer et al. |
| 6,663,589 | B1 | 12/2003 | Halevy | 2004/0194790 A1 | 10/2004 | Laufer et al. |
| 6,663,639 | B1 | 12/2003 | Laufer et al. | 2004/0243178 A1 | 12/2004 | Haut et al. |
| 6,699,263 | B2 | 3/2004 | Cope | 2004/0243179 A1 | 12/2004 | Foerster |
| 6,706,047 | B2 | 3/2004 | Trout et al. | 2004/0243180 A1 | 12/2004 | Donnelly et al. |
| 6,709,493 | B2 | 3/2004 | DeGuiseppi et al. | 2004/0243227 A1 | 12/2004 | Starksen et al. |
| 6,715,804 | B2 | 4/2004 | Beers | 2004/0260345 A1 | 12/2004 | Foerster |
| 6,719,709 | B2 | 4/2004 | Whalen et al. | 2005/0055087 A1 | 3/2005 | Starksen |
| 6,730,112 | B2 | 5/2004 | Levinson | 2005/0065550 A1 | 3/2005 | Starksen et al. |
| 6,736,823 | B2 | 5/2004 | Darois et al. | 2005/0107811 A1 | 5/2005 | Starksen et al. |
| 6,736,854 | B2 | 5/2004 | Vadurro et al. | 2005/0107812 A1 | 5/2005 | Starksen et al. |
| 6,740,098 | B2 | 5/2004 | Abrams et al. | 2005/0154401 A1 | 7/2005 | Weldon et al. |
| 6,767,037 | B2 | 7/2004 | Wenstrom, Jr. | 2005/0165272 A1 | 7/2005 | Okada et al. |
| 6,770,076 | B2 | 8/2004 | Foerster | 2005/0177181 A1 | 8/2005 | Kagan et al. |
| 6,773,438 | B1 | 8/2004 | Knodel et al. | 2005/0203344 A1 | 9/2005 | Orban, III et al. |
| 6,773,441 | B1 | 8/2004 | Laufer et al. | 2005/0203550 A1 | 9/2005 | Laufer et al. |
| 6,790,213 | B2 | 9/2004 | Cherok et al. | 2005/0216078 A1 | 9/2005 | Starksen et al. |
| 6,802,846 | B2 | 10/2004 | Hauschild et al. | 2005/0251157 A1* | 11/2005 | Saadat et al. .................. 606/153 |
| 6,821,282 | B2 | 11/2004 | Perry et al. | 2005/0251177 A1* | 11/2005 | Saadat et al. .................. 606/153 |
| 6,821,285 | B2 | 11/2004 | Laufer et al. | 2005/0267405 A1 | 12/2005 | Shah |
| 6,821,291 | B2 | 11/2004 | Bolea et al. | 2005/0273138 A1 | 12/2005 | Starksen et al. |
| 6,835,200 | B2 | 12/2004 | Laufer et al. | 2006/0025750 A1 | 2/2006 | Starksen et al. |
| 6,905,475 | B2 | 6/2005 | Hauschild et al. | 2006/0025784 A1 | 2/2006 | Starksen et al. |
| 6,908,473 | B2 | 6/2005 | Skiba et al. | 2006/0025789 A1 | 2/2006 | Laufer et al. |

| | | | |
|---|---|---|---|
| 2006/0025819 A1 | 2/2006 | Nobis et al. | |
| 2006/0030884 A1 | 2/2006 | Yeung et al. | |
| 2006/0058817 A1 | 3/2006 | Starksen et al. | |
| 2006/0089646 A1 | 4/2006 | Bonutti | |
| 2006/0167477 A1 | 7/2006 | Arcia et al. | |
| 2006/0265042 A1 | 11/2006 | Catanese, III et al. | |
| 2006/0282081 A1 | 12/2006 | Fanton et al. | |
| 2007/0049929 A1 | 3/2007 | Catanese, III | |
| 2007/0049970 A1 | 3/2007 | Belef et al. | |
| 2007/0060931 A1 | 3/2007 | Hamilton et al. | |
| 2007/0088362 A1 | 4/2007 | Bonutti | |
| 2007/0112385 A1 | 5/2007 | Conlon | |
| 2007/0142846 A1 | 6/2007 | Catanese, III et al. | |
| 2007/0173888 A1 | 7/2007 | Gertner et al. | |
| 2007/0260259 A1 | 11/2007 | Fanton et al. | |
| 2008/0009888 A1 | 1/2008 | Ewers et al. | |
| 2008/0021445 A1 | 1/2008 | Elmouelhi et al. | |
| 2008/0033488 A1 | 2/2008 | Catanese, III et al. | |
| 2008/0039894 A1 | 2/2008 | Catanese, III et al. | |
| 2008/0045978 A1 | 2/2008 | Kuhns et al. | |
| 2008/0058710 A1 | 3/2008 | Wilk | |
| 2008/0065120 A1 | 3/2008 | Zannis et al. | |
| 2008/0082113 A1 | 4/2008 | Bishop et al. | |
| 2008/0086172 A1 | 4/2008 | Martin et al. | |
| 2008/0091220 A1 | 4/2008 | Chu | |
| 2008/0091237 A1 | 4/2008 | Schwartz et al. | |
| 2008/0119874 A1 | 5/2008 | Merves | |
| 2008/0154378 A1 | 6/2008 | Pelo | |
| 2008/0195145 A1 | 8/2008 | Bonutti et al. | |
| 2008/0208220 A1 | 8/2008 | Shiono et al. | |
| 2010/0010631 A1 | 1/2010 | Otte et al. | |
| 2010/0114162 A1 | 5/2010 | Bojarski et al. | |
| 2010/0286106 A1 | 11/2010 | Gat et al. | |
| 2010/0286679 A1 | 11/2010 | Hoey et al. | |

FOREIGN PATENT DOCUMENTS

| | | |
|---|---|---|
| EP | 0246836 | 12/1991 |
| EP | 0464480 | 1/1992 |
| EP | 0632999 | 1/1995 |
| EP | 1016377 | 7/2000 |
| EP | 1082941 | 3/2005 |
| EP | 1006909 | 1/2007 |
| EP | 1852071 | 7/2007 |
| EP | 1670361 | 4/2008 |
| EP | 1884198 | 6/2008 |
| EP | 1884199 | 6/2008 |
| EP | 1331886 | 12/2008 |
| FR | 2750031 | 6/1996 |
| JP | 58036559 | 3/1983 |
| JP | 9122134 | 5/1997 |
| JP | 2004344427 | 12/2004 |
| RU | 2062121 | 6/1996 |
| RU | 2112571 | 6/1998 |
| RU | 2128012 | 3/1999 |
| RU | 2221501 | 1/2004 |
| SU | 0825094 | 4/1981 |
| WO | WO9210142 | 6/1992 |
| WO | WO9304727 | 3/1993 |
| WO | WO9315664 | 8/1993 |
| WO | WO0230335 | 4/2002 |
| WO | WO03039334 | 5/2003 |
| WO | WO03077772 | 9/2003 |
| WO | WO2004019787 | 3/2004 |
| WO | WO2004017845 | 4/2004 |
| WO | WO2004030569 | 4/2004 |
| WO | WO2004103189 | 12/2004 |
| WO | WO2007064906 | 6/2007 |
| WO | WO2007053516 | 10/2007 |
| WO | WO2008006084 | 1/2008 |
| WO | WO2008043044 | 4/2008 |
| WO | WO2008043917 | 4/2008 |
| WO | 2009009617 | 1/2009 |
| WO | WO2010011832 | 1/2010 |

OTHER PUBLICATIONS

Osamu Miyake, "Medical Examination and Treatment for BPH", Pharma Med vol. 22, No. 3, 2004, p. 97-103.

Ohashi Teruhisa, "Urinary Dysfunction by Lower Urinary Tract Obstruction in Male", Pharma Medica vol. 8, No. 8, p. 35-39.

Daito Takashi, "Low-Invasive Treatment for BPH", Medico vol. 34, No. 10, p. 366-369.

Koyanagi Tomohiko, et al., "Surgery View of 21st Century", Urological Surgery, vol. 84, No. 1, p. 47-53.

Yeung, Jeff, "Treating Urinary Stress Incontinence Without Incision with Endoscopic Suture Anchor & Approximating Device," Aleeva Medical, Inc., 2007.

Sharp, Howard T., M.D., et al., "Instruments and Methods—The 4-S Modification of the Roeder Knot: How to Tie It", Obstetrics & Gynecology, p. 1004-1006, vol. 90, No. 6, Dec. 1997.

P. Schauer et al., "New applications for endoscopy: the emerging field of endoluminal and transgastric bariatric surgery," Surgical Endoscopy, Received Apr. 24, 2006/Accepted Jun. 7, 2006.

Richard Berges et al., "Alternative Minimalinvasive Therapien Beim Benignen Prostatasyndrom", Medizin, Jg. 104, Heft 37, Sep. 14, 2007.

Rudolf Hartung, et al., "Instrumentelle Therapie der benignen Prostatahyperplasie", Medizin, Deutsches Ärzteblatt 97, Heft 15, Apr. 14, 2000.

Klaus Hofner, et al., "Operative Therapie des benignen Prostatasyndroms", Medizin, Dtsch Arztebl 2007; 104(36):A 2424-9.

R. Hubmann, "Geschichte der transurethralen Prostataeingriffe", Geschichte der Medizin, Urologe [B] 2000 40:152-160.

U. Jonas, et al., "Benigne Prostatahyperplasie", Der Urologe 2006—[Sonderheft] 45:134-144.

O.A. Bacharova, et al., "The Effect of Rhodiolae Rosea Extract on Incidence Rate of Superficial Bladder Carcinoma Relapses", Kozin 1995.

S. Kruck, et al., "Aktuelle Therapiennaglichkeiten des Benignen Prostata-Syndroms", J Urol Urogynakol 2009; 16 (1): 19-22.

Osamu Miyake, "Medical Examination and Treatment for BPH", Pharma Med vol. 22, No. 3, 2004, p. 97-103.

Ohashi Teruhisa, "Urinary Dysfunction by Lower Urinary Tract Obstruction in Male", Pharma Medica vol. 8, No. 8, p. 35-39, 1990.

O. Reich, et al., "Benignes Prostatasyndrom (BPS)", Der Urologe A Issue vol. 45, No. 6, Jun. 2006, p. 769-782.

Daito Takashi, "Low-Invasive Treatment for BPH", Medico vol. 34, No. 10, p. 366-369, 2003.

Trapeznikov et al., "New Technologies in the Treatment of Benign Prostatic Hyperplasia", Urologia Nefrol (Mosk) 1996, Jul.-Aug. (4):41-47.

Koyanagi Tomohiko, et al., "Surgery View of 21st Century", Urological Surgery, vol. 84, No. 1, p. 47-53, 2001.

Borzhievski, et al., "Tactics of the Surgical Treatment of Patients With Prostatic Adenoma and Acute Urinary Retention", Urologia Nefrol (Mosk), 1987, Jan.-Feb. (1):39-43.

* cited by examiner

ANCHOR DELIVERY SYSTEM WITH REPLACEABLE CARTRIDGE

CROSS-REFERENCES TO RELATED APPLICATIONS

This application is a continuation-in-part of copending U.S. patent application Ser. No. 11/775,162 entitled Multi-Actuating Trigger Anchor Delivery System, filed Jul. 9, 2007, which is a continuation-in-part of copending U.S. patent application Ser. No. 11/671,914, now U.S. Pat. No. 8,157, 815, entitled Integrated Handle Assembly For Anchor Delivery System, filed Feb. 6, 2007, which is a continuation-in-part of U.S. patent application Ser. No. 11/492,690, now U.S. Pat. No. 7,896,891, entitled Apparatus and Method for Manipulating or Retracting Tissue and Anatomical Structure, filed on Jul. 24, 2006, which is a continuation-in-part of U.S. patent application Ser. No. 11/318,246, now U.S. Pat. No. 7,645, 286, entitled Devices, Systems and Methods for Retracting, Lifting, Compressing, Supporting or Repositioning Tissues or Anatomical Structures, filed on Dec. 22, 2005, which is a continuation-in-part of U.S. patent application Ser. No. 11/134,870, now U.S. Pat. No. 7,758,594, entitled Devices, Systems and Methods for Treating Benign Prostatic Hyperplasia and Other Conditions, filed on May 20, 2005, the entire disclosures of which are expressly incorporated herein by reference and claims the benefit of Provisional Application Ser. No. 61/084,937 filed Jul. 30, 2008.

FIELD OF THE INVENTION

The present invention relates generally to medical devices and methods, and more particularly to systems and associated methods for manipulating or retracting tissues and anatomical or other structures within the body of human or animal subjects for the purpose of treating diseases or disorders and/or for cosmetic or reconstructive or other purposes.

BACKGROUND OF THE INVENTION

There are a wide variety of situations in which it is desirable to lift, compress or otherwise reposition normal or aberrant tissues or anatomical structures (e.g., organs, ligaments, tendons, muscles, tumors, cysts, fat pads, etc.) within the body of a human or animal subject. Such procedures are often carried out for the purpose of treating or palliating the effects of diseases or disorders (e.g., hyperplasic conditions, hypertrophic conditions, neoplasias, prolapses, herniations, stenoses, constrictions, compressions, transpositions, congenital malformations, etc.) and/or for cosmetic purposes (e.g., face lifts, breast lifts, brow lifts, etc.) and/or for research and development purposes (e.g., to create animal models that mimic various pathological conditions). In many of these procedures, surgical incisions are made in the body and laborious surgical dissection is performed to access and expose the affected tissues or anatomical structures. Thereafter, in some cases, the affected tissues or anatomical structures are removed or excised. In other cases, various natural or man made materials are used to lift, sling, reposition or compress the affected tissues.

Benign Prostatic Hyperplasia (BPH)

One example of a condition where it is desirable to lift, compress or otherwise remove a pathologically enlarged tissue is Benign Prostatic Hyperplasia (BPH). BPH is one of the most common medical conditions that affect men, especially elderly men. It has been reported that, in the United States, more than half of all men have histopathologic evidence of BPH by age 60 and, by age 85, approximately 9 out of 10 men suffer from the condition. Moreover, the incidence and prevalence of BPH are expected to increase as the average age of the population in developed countries increases.

The prostate gland enlarges throughout a man's life. In some men, the prostatic capsule around the prostate gland may prevent the prostate gland from enlarging further. This causes the inner region of the prostate gland to squeeze the urethra. This pressure on the urethra increases resistance to urine flow through the region of the urethra enclosed by the prostate. Thus the urinary bladder has to exert more pressure to force urine through the increased resistance of the urethra. Chronic over-exertion causes the muscular walls of the urinary bladder to remodel and become stiffer. This combination of increased urethral resistance to urine flow and stiffness and hypertrophy of urinary bladder walls leads to a variety of lower urinary tract symptoms (LUTS) that may severely reduce the patient's quality of life. These symptoms include weak or intermittent urine flow while urinating, straining when urinating, hesitation before urine flow starts, feeling that the bladder has not emptied completely even after urination, dribbling at the end of urination or leakage afterward, increased frequency of urination particularly at night, urgent need to urinate etc.

In addition to patients with BPH, LUTS may also be present in patients with prostate cancer, prostate infections, and chronic use of certain medications (e.g. ephedrine, pseudoephedrine, phenylpropanolamine, antihistamines such as diphenhydramine, chlorpheniramine etc.) that cause urinary retention especially in men with prostate enlargement.

Although BPH is rarely life threatening, it can lead to numerous clinical conditions including urinary retention, renal insufficiency, recurrent urinary tract infection, incontinence, hematuria, and bladder stones.

In developed countries, a large percentage of the patient population undergoes treatment for BPH symptoms. It has been estimated that by the age of 80 years, approximately 25% of the male population of the United States will have undergone some form of BPH treatment. At present, the available treatment options for BPH include watchful waiting, medications (phytotherapy and prescription medications), surgery and minimally invasive procedures.

For patients who choose the watchful waiting option, no immediate treatment is provided to the patient, but the patient undergoes regular exams to monitor progression of the disease. This is usually done on patients that have minimal symptoms that are not especially bothersome.

Surgical procedures for treating BPH symptoms include Transurethal Resection of Prostate (TURP), Transurethral Electrovaporization of Prostate (TVP), Transurethral Incision of the Prostate (TUIP), Laser Prostatectomy and Open Prostatectomy.

Minimally invasive procedures for treating BPH symptoms include Transurethral Microwave Thermotherapy (TUMT), Transurethral Needle Ablation (TUNA), Interstitial Laser Coagulation (ILC), and Prostatic Stents.

The most effective current methods of treating BPH carry a high risk of adverse effects. These methods and devices either require general or spinal anesthesia or have potential adverse effects that dictate that the procedures be performed in a surgical operating room, followed by a hospital stay for the patient. The methods of treating BPH that carry a lower risk of adverse effects are also associated with a lower reduction in the symptom score. While several of these procedures can be conducted with local analgesia in an office setting, the patient does not experience immediate relief and in fact often experiences worse symptoms for weeks after the procedure until the body begins to heal. Additionally all device approaches require a urethral catheter placed in the bladder, in some cases for weeks. In some cases catheterization is indicated because the therapy actually causes obstruction during a period of time post operatively, and in other cases it is indicated because of post-operative bleeding and potentially occlusive clot formation. While drug therapies are easy to administer, the results are suboptimal, take significant time to take effect, and often entail undesired side effects.

Urinary Incontinence (UI)

Many women experience loss of bladder control following childbirth or in old age. This condition is broadly referred to as urinary incontinence (UI). The severity of UI varies and, in severe cases, the disorder can be totally debilitating, keeping the patient largely homebound. It is usually associated with a cystocele, which results from sagging of the neck of the urinary bladder into or even outside the vagina The treatments for UI include behavioral therapy, muscle strengthening exercises (e.g., Kegel exercises), drug therapy, electrical stimulation of the pelvic nerves, use of intravaginal devices and surgery.

In severe cases of UI, surgery is generally the best treatment option. In general, the surgical procedures used to treat UI attempt to lift and support the bladder so that the bladder and urethra are returned to their normal positions within the pelvic cavity. The two most common ways of performing these surgeries is through incisions formed in the abdominal wall or though the wall of the vagina.

A number of different surgical procedures have been used to treat UI. The names for these procedures include the Birch Procedure, Marshall-Marchetti Operation, MMK, Pubo-Vaginal Sling, Trans-Vaginal Tape Procedure, Urethral Suspension, Vesicourethral Suspension. These procedures generally fall into two categories, namely a) retropubic suspension procedures and b) sling procedures.

In retropubic suspension procedures, an incision is typically made in the abdominal wall a few inches below the navel and a network of connectors are placed to support the bladder neck. The connectors are anchored to the pubic bone and to other structures within the pelvis, essentially forming a cradle which supports the urinary bladder.

In sling procedures, an incision is typically made in the wall of the vagina and a sling is crafted of either natural tissue or synthetic (man-made) material to support the bladder neck. Both ends of the sling may be attached to the pubic bone or tied in front of the abdomen just above the pubic bone. In some sling procedures a synthetic tape is used to form the sling and the ends of the synthetic tape are not tied but rather pulled up above the pubic bone.

The surgeries used to treat UI are generally associated with significant discomfort as the incisions heal and may require a Foley or supra-pubic urinary catheter to remain in place for at least several days following the surgery. Thus, there exists a need in the art for the development of minimally invasive (e.g., non-incisional) procedures for the treatment of UI with less postoperative discomfort and less requirement for post-surgical urinary catheterization.

Cosmetic or Reconstructive Tissue Lifting and Repositioning

Many cosmetic or reconstructive surgical procedures involve lifting, compressing or repositioning of natural tissue, natural tissue or artificial grafts or aberrant tissue. For example, surgical procedures such as face lifts, brow lifts, neck lifts, tummy tucks, etc. have become commonplace. In many cases, these procedures are performed by creating incisions through the skin, dissecting to a plane beneath muscles and fascia, freeing the muscles, fascia and overlying skin from underlying structures (e.g., bone or other muscles), lifting or repositioning the freed muscles, fascia and overlying skin and then attaching the repositioned tissues to underlying or nearby structures (e.g., bone, periostium, other muscles) to hold the repositioned tissues in their new (e.g., lifted) position. In some cases excess skin may also be removed during the procedure.

There have been attempts to develop minimally invasive devices and methods for cosmetic lifting and repositioning of tissues. For example, connector suspension lifts have been developed where one end of a standard or modified connector thread is attached to muscle and the other end is anchored to bone, periostium or another structure to lift and reposition the tissues as desired. Some of these connector suspension techniques have been performed through cannulas or needles inserted though relatively small incisions of puncture wounds.

There remains a need for the development of new devices and methods that may be used for various procedures where it is desired to lift, compress, support or reposition tissues or organs within the body with less intraoperative trauma, less post-operative discomfort and/or shorter recovery times. Further, there is a need for an apparatus and related method which is easy and convenient to repeatedly employ in an interventional procedure. In particular, there is an apparatus which can accomplish accessing an interventional site as well as be reused after reloading. Moreover, there is a need for a device including manual as well as automatic features so that successful use is facilitated.

The present invention addresses these and other needs.

SUMMARY OF THE INVENTION

Briefly and in general terms, the present invention is directed towards an apparatus and method for deploying an anchor assembly within a patient's body. The apparatus of the present invention includes various subassemblies which are mobilized via a trigger or other manually accessible structure. The operation of the subassemblies is coordinated and synchronized to ensure accurate and precise implantation of an anchor assembly. Structure for re-loading of the device is also described.

In one embodiment, the delivery device is embodied in a tissue approximation assembly. The tool includes a case assembly enclosing a trigger assembly, a needle spool assembly and a replaceable cartridge assembly. Extending from the case assembly and attached to the trigger assembly and needle spool assembly is a shaft assembly. Also, extending through the shaft assembly and connected to the trigger assembly are a pusher assembly, needle, and a cutter assembly. Operatively associated with the needle spool and cartridge assemblies are a needle actuator and a needle retraction actuator (e.g., a lever assembly). A rear actuator is operatively associated with the trigger assembly. This actuator can be positioned on a side of the instrument and can also be incorporated into the lever. It is also contemplated that each of the actuators can be incorporated into a single structure for creating movement of internal mechanisms of the device. Activation of the needle actuator accomplishes the advancement of a needle assembly and a first component of an anchor assembly attached to a connector member, to an interventional site. Activation of the needle retraction actuator withdraws the needle assembly leaving the first component of the anchor assembly at the interventional site. Thereafter, manipulation of the rear actuator results in lockingly engaging a second anchor component with the connector member and cutting the connector member to a desired length.

In one particular aspect, the present invention is directed towards a delivery device which accomplishes the delivery of a first or distal anchor assembly component at a first location within a patient's body and the delivery of a second or proximal anchor assembly component at a second location within the patient. The device also accomplishes imparting a tension during delivery and a tension between implanted anchor components as well as cutting the anchor assembly to a desired length and assembling the proximal anchor in situ. The procedure can be viewed employing a scope inserted in the device. Also, the delivery device can be sized and shaped to be compatible with a sheath in the range of 18 to 24 F, preferably a 19 F sheath.

Additionally, in a contemplated embodiment of an anchor delivery system, actuating a needle deploy actuator results in a needle assembly being advanced within a patient to an interventional site. Activating a needle retraction lever accomplishes the withdrawal of the needle and deployment of a first anchor component of an anchor assembly at the interventional site. Depression of a second actuator facilitates the incorporation of a second component into the anchor assembly and its release at the interventional site. A reset assembly is further provided to reset aspects of the delivery system as is a bail out assembly configured to release anchor structure from the delivery device. Moreover, various locking mechanisms are provided for both operational as well as safety reasons.

The present invention also contemplates a reversible procedure as well as an anchor assembly with sufficient visibility when viewed ultrasonically, by xray, MRI or other imaging modalities. In one aspect, the implant procedure is reversible by severing a connector of an anchor assembly and removing an anchor of the anchor assembly such as by removing a proximally placed anchor previously implanted in an urethra. Moreover, the anchor assemblies can be formed of structures such as that having increased density to thereby facilitate ultrasound viewing or other imaging modalities.

The anchor assembly can be configured to accomplish retracting, lifting, compressing, supporting or repositioning tissue within the body of a human or animal subject. Moreover, the apparatus configured to deploy the anchor assembly as well as the anchor assembly itself are configured to complement and cooperate with body anatomy. Further, the anchor assembly may be coated or imbedded with therapeutic or diagnostic substances, in particular Botulinum toxin, or a silver ion coating or such substances can be introduced into or near an interventional site by the anchor deployment device or other structure.

In one embodiment, the anchor delivery device includes a handle assembly with a actuator attached thereto. The actuator is associated with a body of the handle assembly and is operatively attached to the needle assembly and structure that advances the first anchor member. A second actuator is operatively associated with structure that accomplishes assembling the second anchor member to the connector member. Additionally, the handle assembly is equipped with structure that is configured in one contemplated embodiment, to effect the cutting of the anchor assembly to a desired length and deployment of the structure at an interventional site.

In a specific embodiment, the anchor delivery device includes a generally elongate tubular housing assembly member extending distally from a handle assembly including an actuator. The proximal end of the handle assembly is equipped with mounting structure configured to receive a telescope or other endoscopic viewing instrument. A bore sized to receive the telescope extends distally through a body of the handle assembly and continues through an outer tubular cover member forming the generally elongate member. Housed within the tubular housing assembly are a telescope tube having an interior defining a distal section of the bore sized to receive the telescope, an upper tubular member assembly sized to receive at least one component of the implant assembly through a needle housing configured to receive the needle assembly, and a lower tubular member assembly sized to receive at least one second component of the implant assembly through a cutter member.

Additionally, in a preferred embodiment the first anchor member includes a tubular portion, a mid-section and a tail portion. The tail portion of the member further includes a connector section which acts as a resilient member. A terminal end portion of the tail is further contemplated to have a surface area larger than the connector section to provide a platform for engaging tissue.

Further, in the preferred embodiment, one component of the second anchor member is embodied in a pin having a first end equipped with a pair of spaced arms and a second end defining a flattened tube.

Moreover, various alternative methods of use are also contemplated. That is, in some applications of the invention, the invention may be used to facilitate volitional or non-volitional flow of a body fluid through a body lumen, modify the size or shape of a body lumen or cavity, treat prostate enlargement, treat urinary incontinence, support or maintain positioning of a tissue, organ or graft, perform a cosmetic lifting or repositioning procedure, form anastomotic connections, and/or treat various other disorders where a natural or pathologic tissue or organ is pressing on or interfering with an adjacent anatomical structure. Also, the invention has a myriad of other potential surgical, therapeutic, cosmetic or reconstructive applications, such as where a tissue, organ, graft or other material requires retracting, lifting, repositioning, compression or support.

In one or more embodiments, the disclosed device can have a compact shaft profile which, for example, can fit into a 19 F cystoscopic sheath for patient tolerant access during an awake procedure. The device has a stiff distal shaft to allow manual compression of tissue at an interventional site by means of leveraging the tool handle. In a specific application, a spring-driven needle can be deployed to a single depth, and sized to pierce through a predominate population of urethral-prostatic distances. An automated deployment of the needle through anatomy is contemplated to pierce reliably with sufficient force and speed. Moreover, the device can be provided with structure providing manual retraction of the needle to provide tactile feedback to the user to confirm completion of needle retraction. This also simplifies the mechanics to provide the option to retract the needle at any time and results in depositing the first and second anchor components in the tissue after needle retraction.

Further, the device can be configured with suture guides which provide centering of the suture and/or a stop to hold the suture stable while an anchor is placed on it to ensure a reliable assembly of an anchor assembly. Additionally, an automated tensioning spring is provided for actuation during the lever retraction, thus providing consistent suture tension during the anchor deployment and making the anchor seating more reliable, as well as minimizing the distance between the two anchors and holding the target tissue approximated. Also, a delivery tool shaft lumen that has at least one flat registration surface to align the anchors to be registered with the tensioned suture as well as a spring-like obstructive tab are used to maintain the most distal anchor in position prior to deployment. Actuation of a final trigger can then translate a pusher element to advance the anchor onto the suture with sufficient speed and force to seat with reliable retention force.

Other features and advantages of the present invention will become apparent from the following detailed description, taken in conjunction with the accompanying drawings, which illustrate, by way of example, the principles of the invention.

DETAILED DESCRIPTION OF THE PREFERRED EMBODIMENTS

Turning now to the figures, which are provided by way of example and not limitation, the present disclosure is directed to a device configured to deliver anchor assemblies within a patient's body. As stated, the disclosed apparatus can be employed for various medical purposes including but not limited to retracting, lifting, compressing, approximating, supporting or repositioning tissues, organs, anatomical structures, grafts or other material found within a patient's body. Such tissue manipulation is intended to facilitate the treatment of diseases or disorders. Moreover, the disclosed invention has applications in cosmetic or reconstruction purposes or in areas relating the development or research of medical treatments.

In one particular aspect, the anchor assembly of the present disclosure is contemplated to be formed of a structure which is visible by ultrasound. Accordingly, the anchor assembly can be viewed during ultrasonic body scans such as during normal trans-rectal ultrasound when a medical professional is conducting diagnoses or treatment associated with conditions like prostate cancer.

In an aspect of the present invention, one portion of an anchor assembly or implant is positioned and implanted against a first section of anatomy. A second portion of the anchor assembly or implant is then positioned and implanted adjacent a second section of anatomy for the purpose of retracting, lifting, compressing, approximating, supporting or repositioning the second section of anatomy with respect to the first section of anatomy as well as for the purpose of retracting, lifting, compressing, approximating, supporting or repositioning the first section of anatomy with respect to the second section of anatomy. It is also to be recognized that both a first and second portion of the anchor assembly can be configured to accomplish the desired retracting, lifting, compressing, approximating, supporting or repositioning of anatomy due to tension supplied thereto via a connector assembly affixed to the first and second portions of the anchor assembly or implant.

Figure 1:
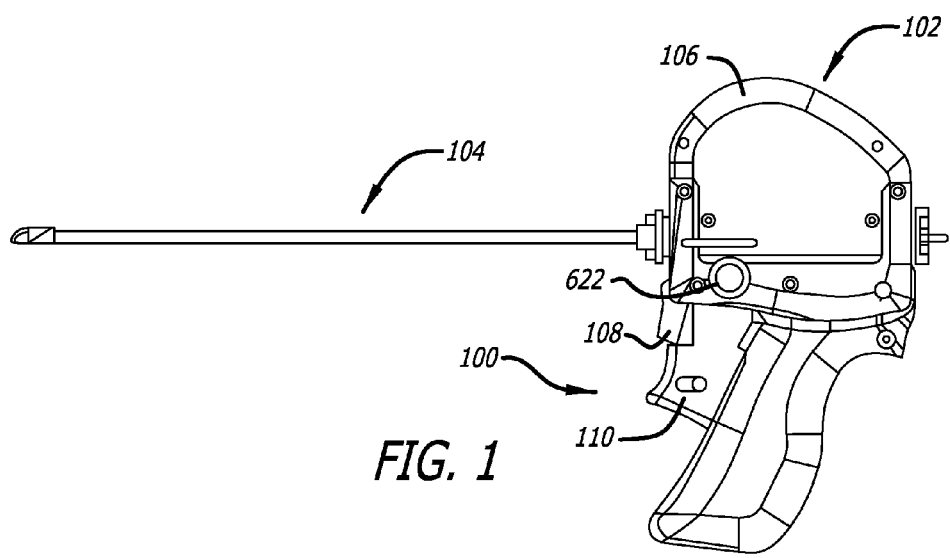
FIG. 1 is a left side view, depicting one embodiment of an anchor delivery system.
Figure 2:
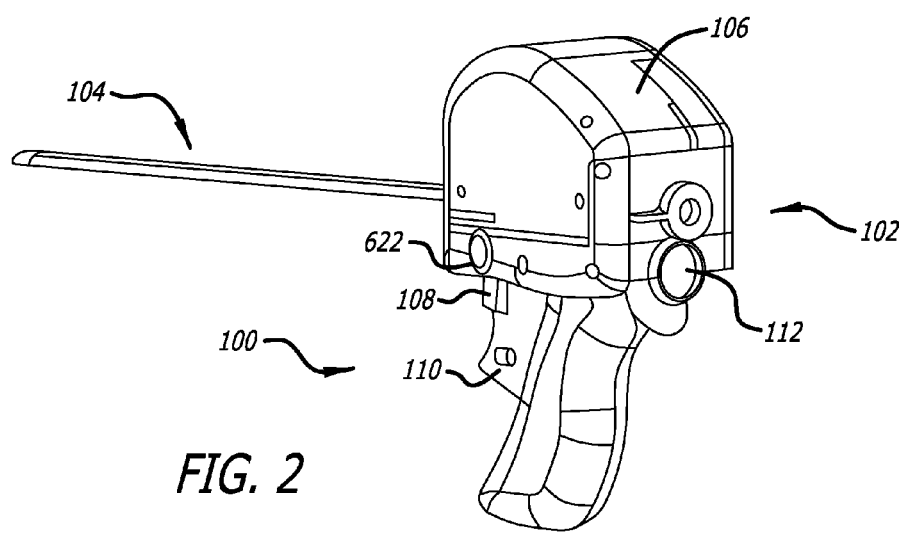
FIG. 2 is a perspective view, depicting the anchor delivery system of FIG. 1.
Figure 3:
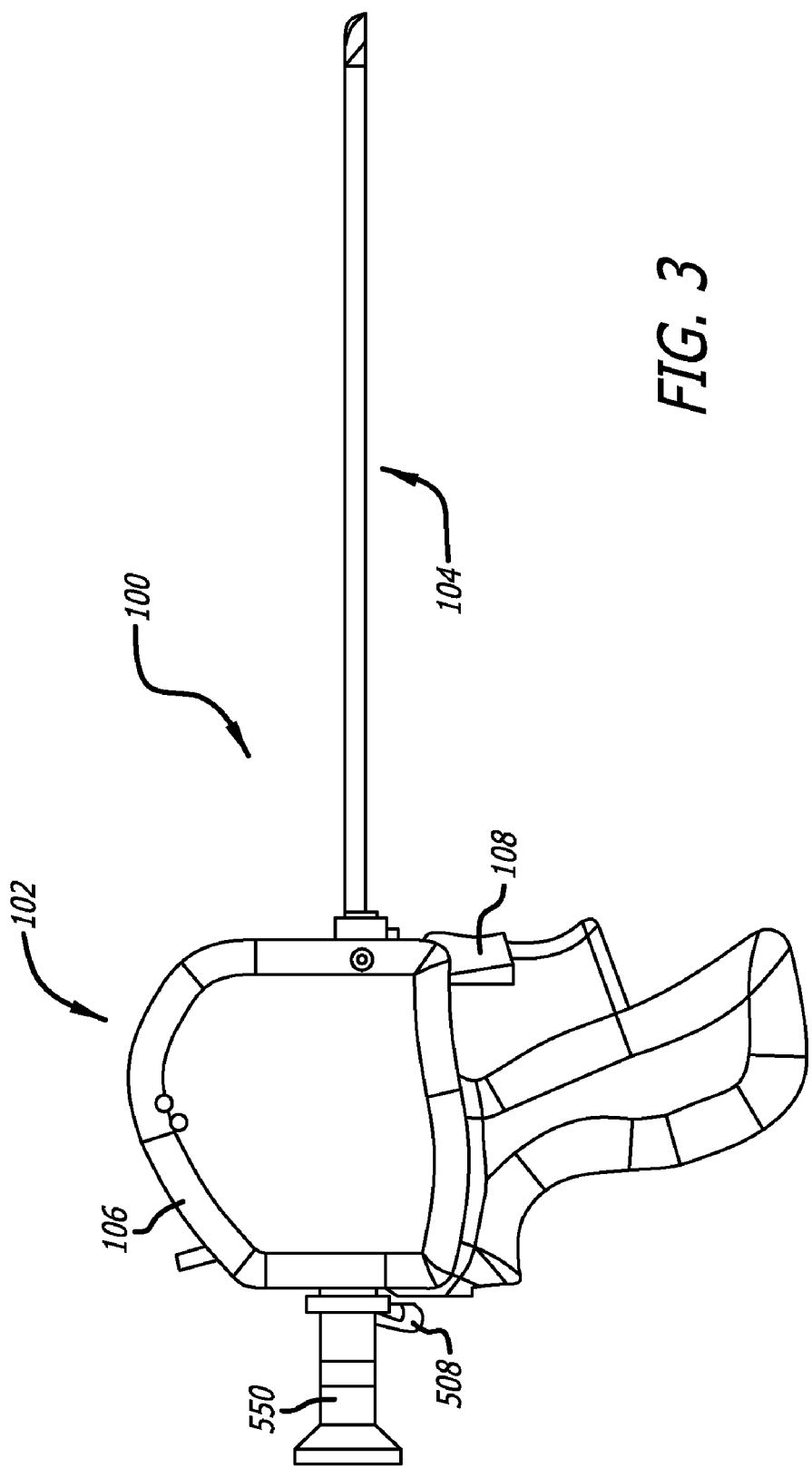
FIG. 3 is a right side view, depicting the anchor delivery system of FIG. 1.

Referring now to FIGS. 1-3, there is shown one embodiment of a device 100. This device is configured to include structure that is capable of both gaining access to an interventional site as well as assembling and implanting one or more anchor assemblies or implants within a patient's body. In one aspect, the device 100 is configured to assemble and implant a single anchor assembly or implant with a replaceable cartridge. If the user replaces the cartridge another anchor assembly or implant can be assembled and implanted. The device is further contemplated to be compatible for use with a 19 F sheath. The device additionally includes structure configured to receive a conventional remote viewing device (e.g., an endoscope) so that the steps being performed at the interventional site can be observed.

The anchor delivery device 100 includes a handle assembly 102 connected to an elongate tissue access assembly 104. The elongate tissue access assembly 104 houses components employed to construct an anchor assembly and is sized to fit into a 19 F cystosopic sheath for patient tolerance during a procedure in which the patient is awake rather than under general anesthesia. The tissue access assembly is stiff to allow manual compression of tissue at an interventional site by leveraging the handle assembly 102.

The anchor delivery device 100 further includes a number of subassemblies. A handle case assembly 106 including mating handle parts encase the handle assembly 102. The handle assembly 102 is sized and shaped to fit comfortably within an operator's hand and can be formed from conventional materials. Windows can be formed in the handle case assembly 106 to provide access to internal mechanisms of the device so that a manual override is available to the operator in the event the interventional procedure needs to be abandoned.

In one embodiment, the delivery device 100 is equipped with various activatable members which facilitate assembly and delivery of an anchor assembly at an interventional site. A needle actuator 108 is provided and as described in detail below, effectuates the advancement of a needle assembly (loaded with a first component of an anchor assembly) to an interventional site. In a preferred embodiment, the needle assembly has a needle that moves through a curved trajectory and exits the needle assembly in alignment with the handle element, in particular embodiments, in alignment with the grip. In various other embodiments, the needle housing is oriented such that the needles exits the housing at either the two o'clock or ten o'clock positions relative to a handle grip that is vertical. A needle retraction lever assembly 110 is also provided and when actuated causes the needle assembly to be withdrawn and expose the first anchor component. This action and the structure involved is also described in detail below. Finally, the delivery device 100 is equipped with a rear or proximal anchor actuator assembly 112 which as fully described below, upon actuation, accomplishes assembly of a second component to the anchor assembly and release of the anchor assembly at the interventional site.

Figure 4:
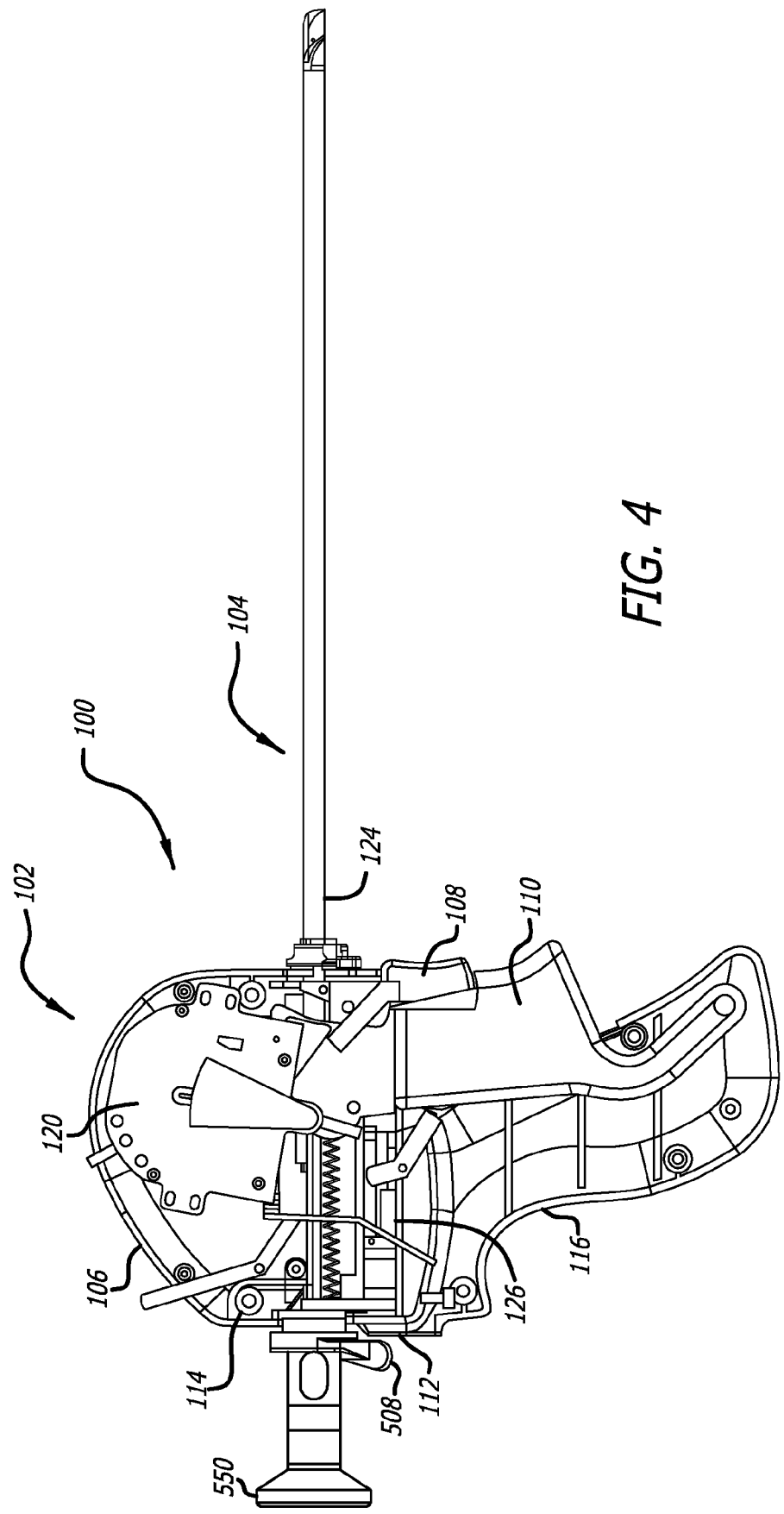
FIG. 4 is a side view, depicting the anchor delivery system of FIG. 3 with a portion of the casing removed.
Figure 5:
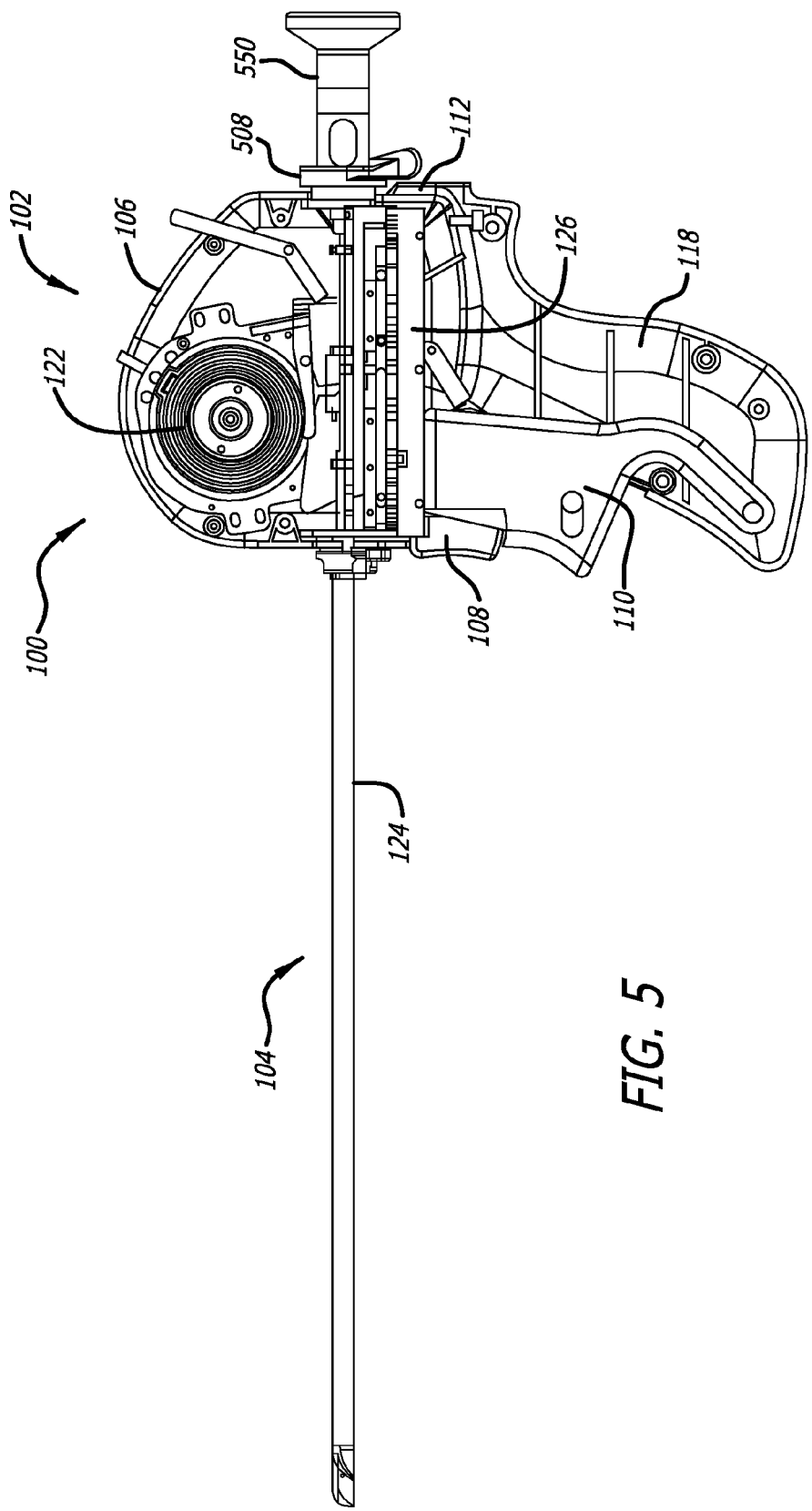
FIG. 5 is a left side view, depicting the anchor delivery device of FIG. 1 with a portion of the casing removed.
Figure 6:
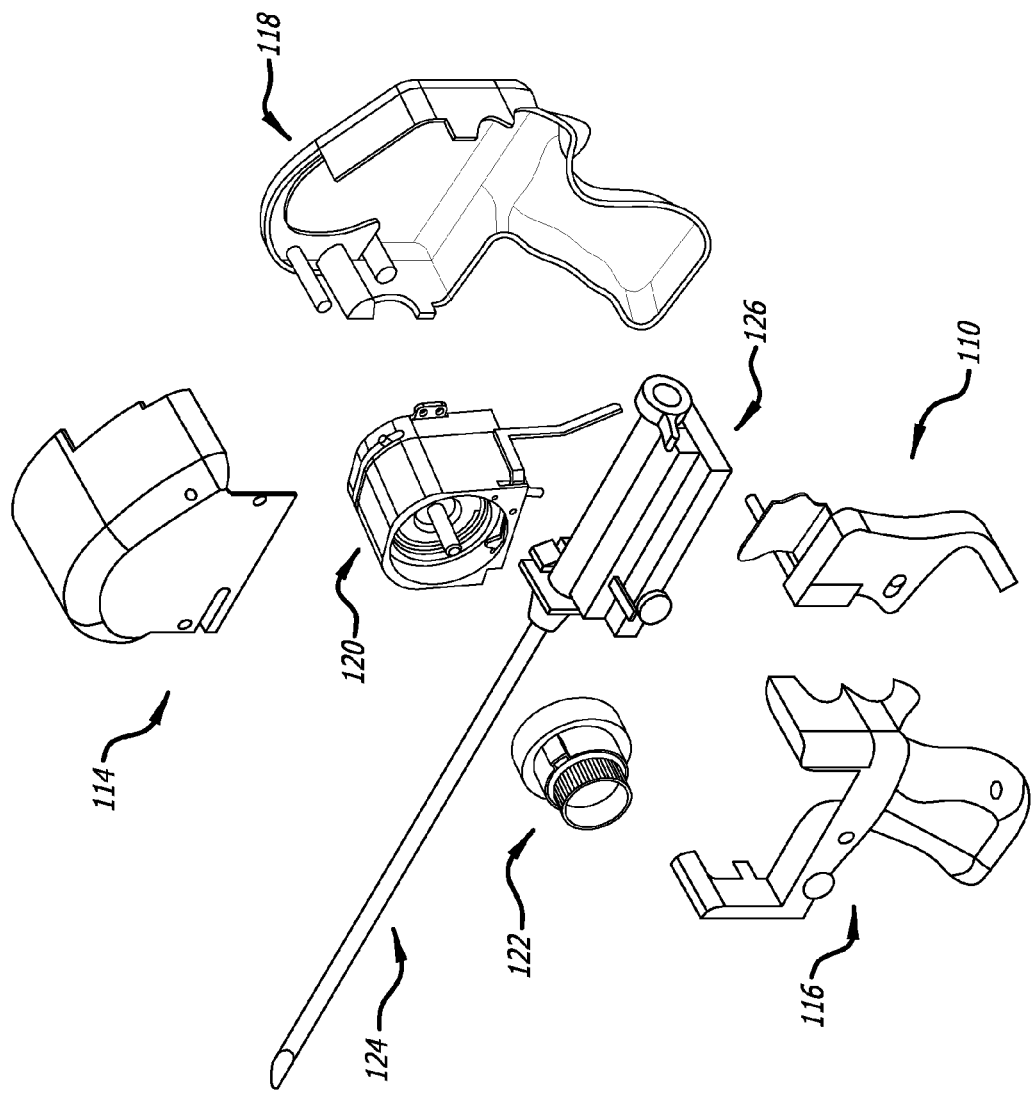
FIG. 6 is an exploded view, depicting the device of FIG. 1.

Turning now to FIGS. 4-6, a number of the subassemblies of the delivery device 100 are introduced, the function and structure of each of which are addressed in detail below. In the embodiment depicted, the case assembly 106 has three mating parts, a left top case 114, a left bottom case 116, and a right case 118. It is within the scope of the present invention that the case assembly be made of a variety of numbers of parts. In addition to mating to enclose subassemblies, the case parts also include structural features for providing rigidity and support for the enclosed components.

Housed within the case assembly 106 are a needle retract spool assembly 120 and a cartridge assembly 122. The rotational axes of the needle spool assembly and cartridge assembly are the same. A shaft assembly 124 includes a portion residing within the case assembly 106 and a portion extending from a forward end of the case assembly. Attached to and operatively associated with the shaft assembly 124 is a trigger assembly 126. The trigger assembly 126 is also housed within the case assembly 106. FIGS. 4 and 5 illustrate the juxtapositional relationships of the various subassemblies and FIG. 6 is an exploded view depicting the subassemblies.

Figure 7:
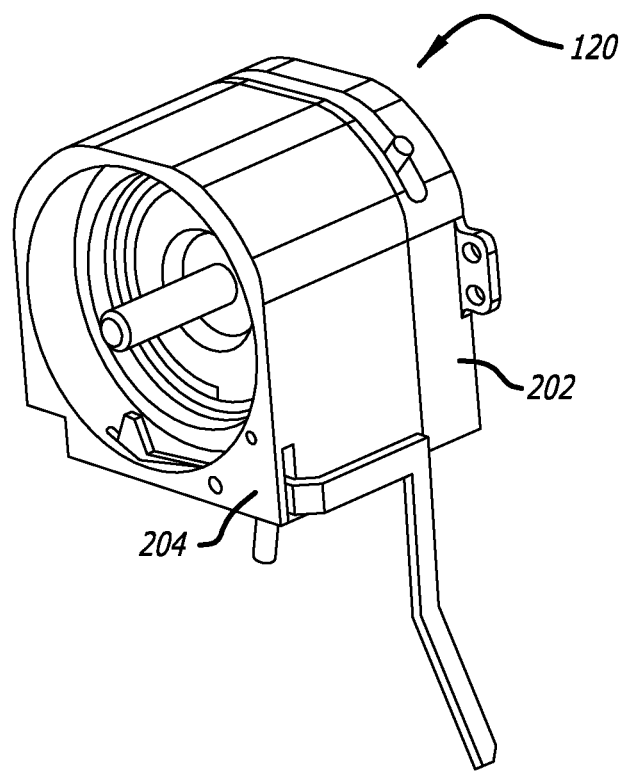
FIG. 7 is a perspective view, depicting a needle drive spool assembly.
Figure 8:
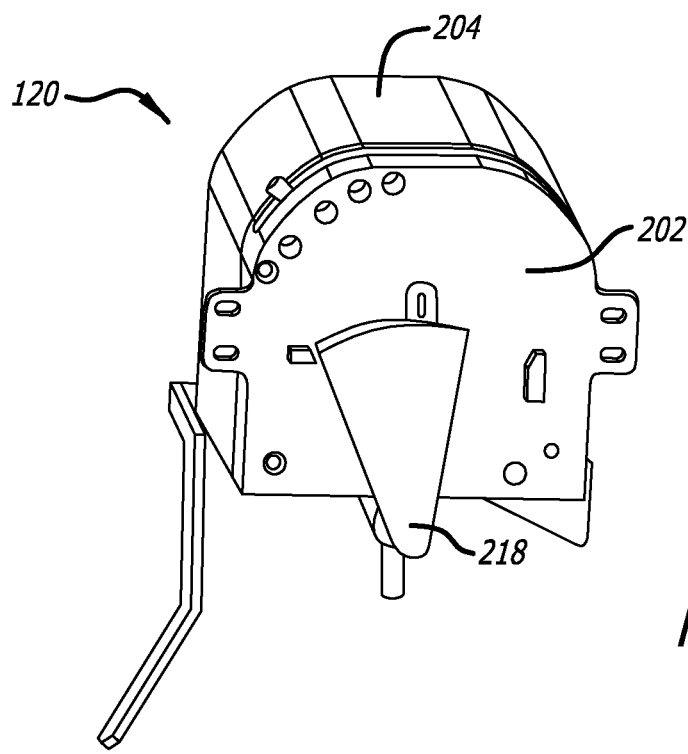
FIG. 8 is another perspective view, depicting the needle drive spool assembly of FIG. 7.
Figure 9:
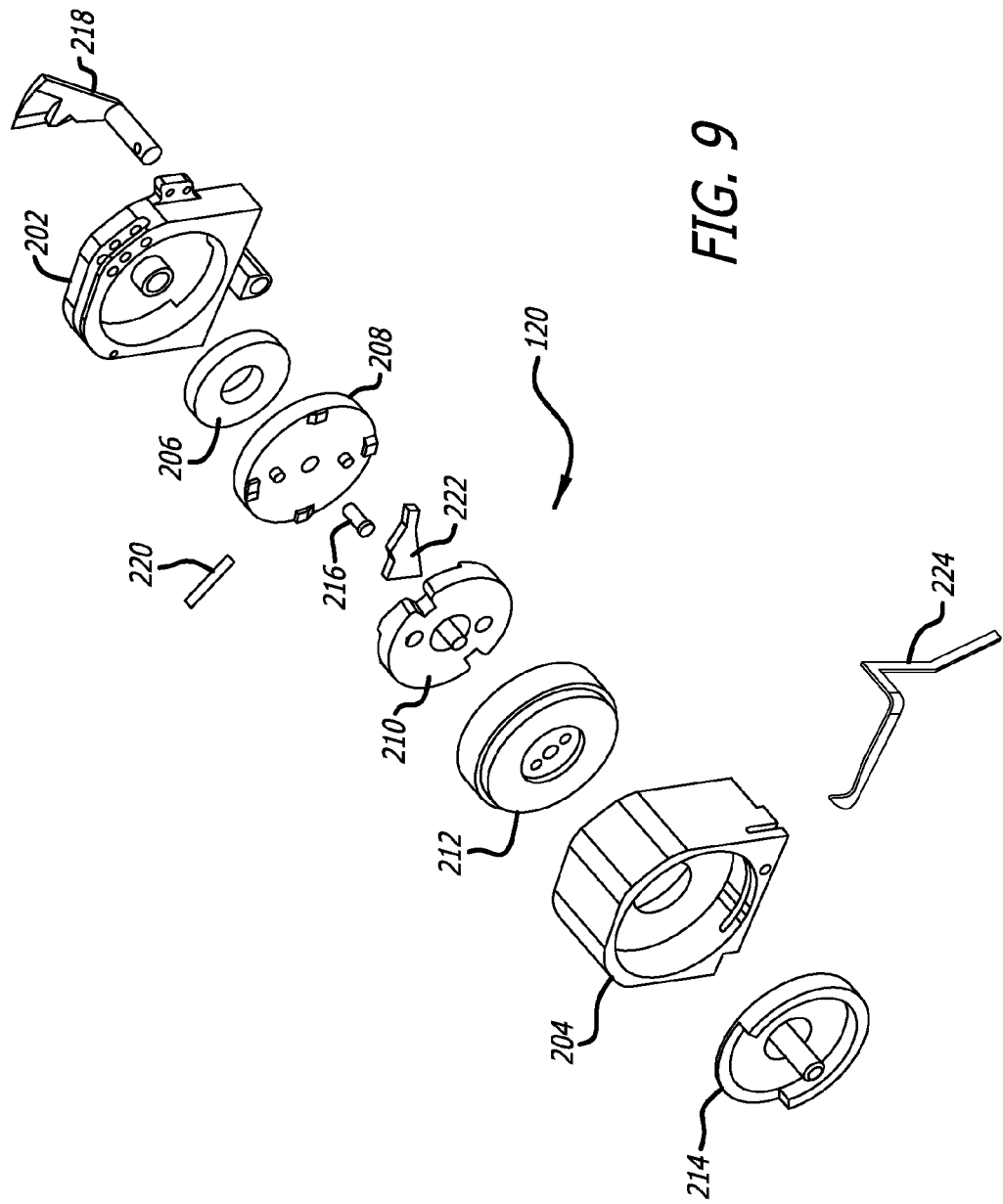
FIG. 9 is an exploded view, depicting the needle drive spool assembly of FIG. 7.

With reference to FIGS. 7-9, details concerning this embodiment of the structure of the needle spool assembly 120 are presented. As described further below, the needle retract spool assembly 120 cooperates with the needle actuator and needle retraction lever to advance and then withdraw a needle assembly at an interventional site.

The needle retract spool assembly 120 is a compact structure including a number of moving pieces. A needle spring housing 202 forms one side of the assembly 120 and is placed adjacent to a needle spool housing 204. An outer side of the needle spring housing 202 forms a generally flat surface and formed on the opposite side of the needle spring housing 202 is a circular recess. When the needle retract spool assembly 120 is in its assembled form, the circular recess of the needle spring housing 202 faces the needle spool housing 204. Formed in opposite sides of the needle spool housing 204 are two additional generally circular recesses.

Between the needle spring housing 202 and the needle spool housing 204 and within the facing circular recesses formed therein, are a needle deploy spring 206 configured within and adjacent a needle deploy spring arbor 208, which is adjacent to a needle clutch plate 210. The needle clutch plate 210, in turn, is adjacent and received within a circular recess formed in a needle clutch cup 212. Received in the needle spool housing 204 recess opposite of the needle spring housing 202 is a needle spool 214. The needle deploy spring 206 functions to rotate the needle spool 214 and to project a tip of the needle through tissue with force and speed. In one approach, it is contemplated that the device 100 be configured so that the needle is deployed to a single depth to pierce through a predominant population of urethral-prostatic distances.

Each of the generally circular profiled needle deploy spring 206 and needle deploy spring arbor 208 include a center through hole. Further, a clutch push rod 216 extends through such aligned holes of a completed assembly from the outer side of the needle spring housing 202 and through the needle deploy spring 206 and needle deploy spring arbor 208. A pivotable clutch actuator 218 configured on the outside surface of the needle spring housing 202, as described in further detail below through its interaction with the needle retraction lever, causes lateral movement of the push rod 216 so that it engages the needle clutch plate 210 separating it from the spring arbor 208. The spring arbor 206 is rotationally biased by the needle deploy spring 206, which can be formed of a helically arranged motor spring. A needle spring reset lever 220 is further provided, the same being accessible to reset the spring arbor 208 after an initial use.

As stated, the clutch plate 210 is received within the needle clutch cup 212. The interior of the clutch cup 212 includes bosses (not shown) sized to mate with corresponding recesses formed in the clutch plate 210. Further, a center hole formed in the clutch plate 210 is sized to receive a center post extending from an adjacent face of the clutch plate. Such structure facilitates complementary rotation of the clutch plate 210 and clutch cup 212. Complementary rotational motion of the clutch cup 212 and the needle spool 214 is also accomplished through an interconnection of these pieces through a center hole form in the needle spool housing 204.

The assembly further includes a needle deploy pawl 222 which is operatively associated with the needle actuator. As shown and described below, the needle actuator pivots the needle deploy pawl 222 away from engagement with the spring arbor 208, thereby permitting rotation of the same.

An unsheathing pawl 224 is also provided and configured at one end to engage the needle retraction lever. At another end of the unsheathing pawl 224 there is structure configured to engage a capsular cartridge spool (described below) to thereby fix its rotational position while the needle spool 214 rotates.

Figure 10:
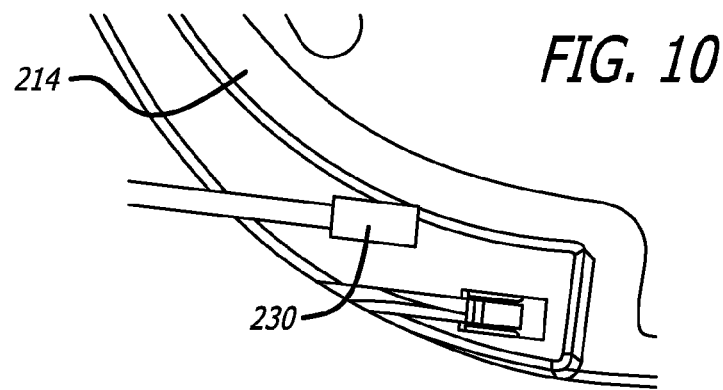
FIG. 10 is an enlarged view, depicting a portion of the needle drive spool assembly.
Figure 11:
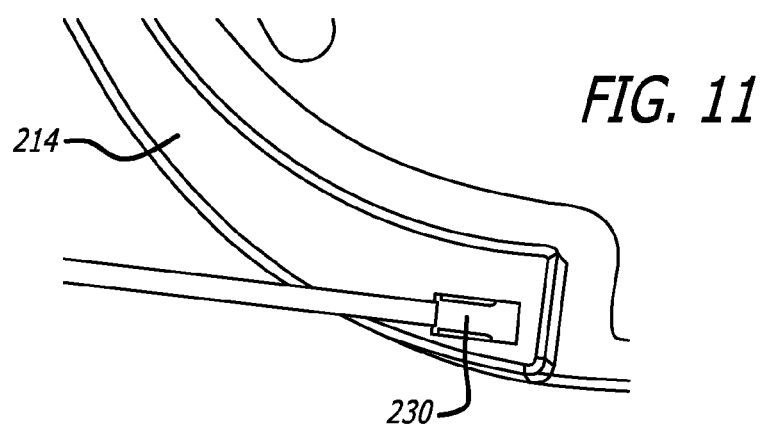
FIG. 11 is an enlarged view, depicting a portion of the needle assembly attached to the needle drive spool assembly.

As shown in FIGS. 10 and 11, a proximal end 230 of a needle assembly can be sized and shaped for connecting with other structure. In one approach, the proximal end of the needle assembly includes a shoulder sized and shaped for receipt within a corresponding recess formed near a periphery of the needle spool 214. Other approaches to effecting a connection are also contemplated such as using a shear wire (not shown) to engage a recess formed in the end of the needle assembly and hold the needle assembly in place relative to the needle spool. Through such connections, rotation of the needle spool 214 can result in advancing and withdrawing lengths of a needle assembly. In this regard, as shown in FIGS. 10-11, a peripheral recess formed in the needle spool 214 is provided to take up lengths of a needle assembly.

Figure 12:
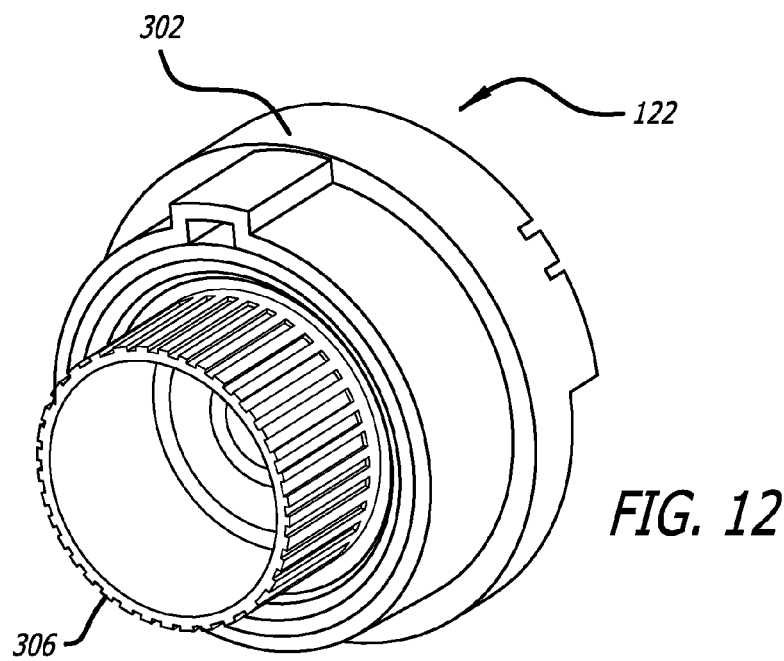
FIG. 12 is a perspective view, depicting a cartridge assembly of the delivery device.
Figure 13:
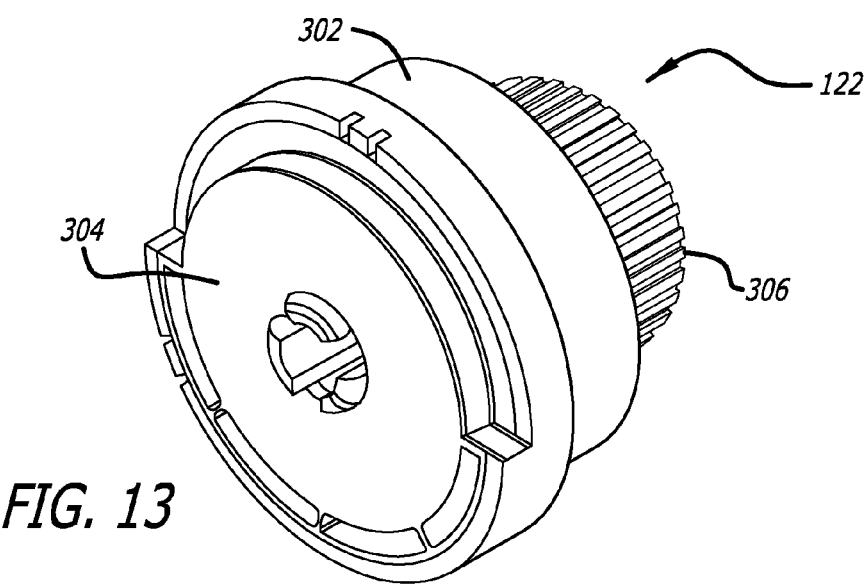
FIG. 13 is a rotated perspective view, depicting the cartridge assembly of FIG. 12.
Figure 14:
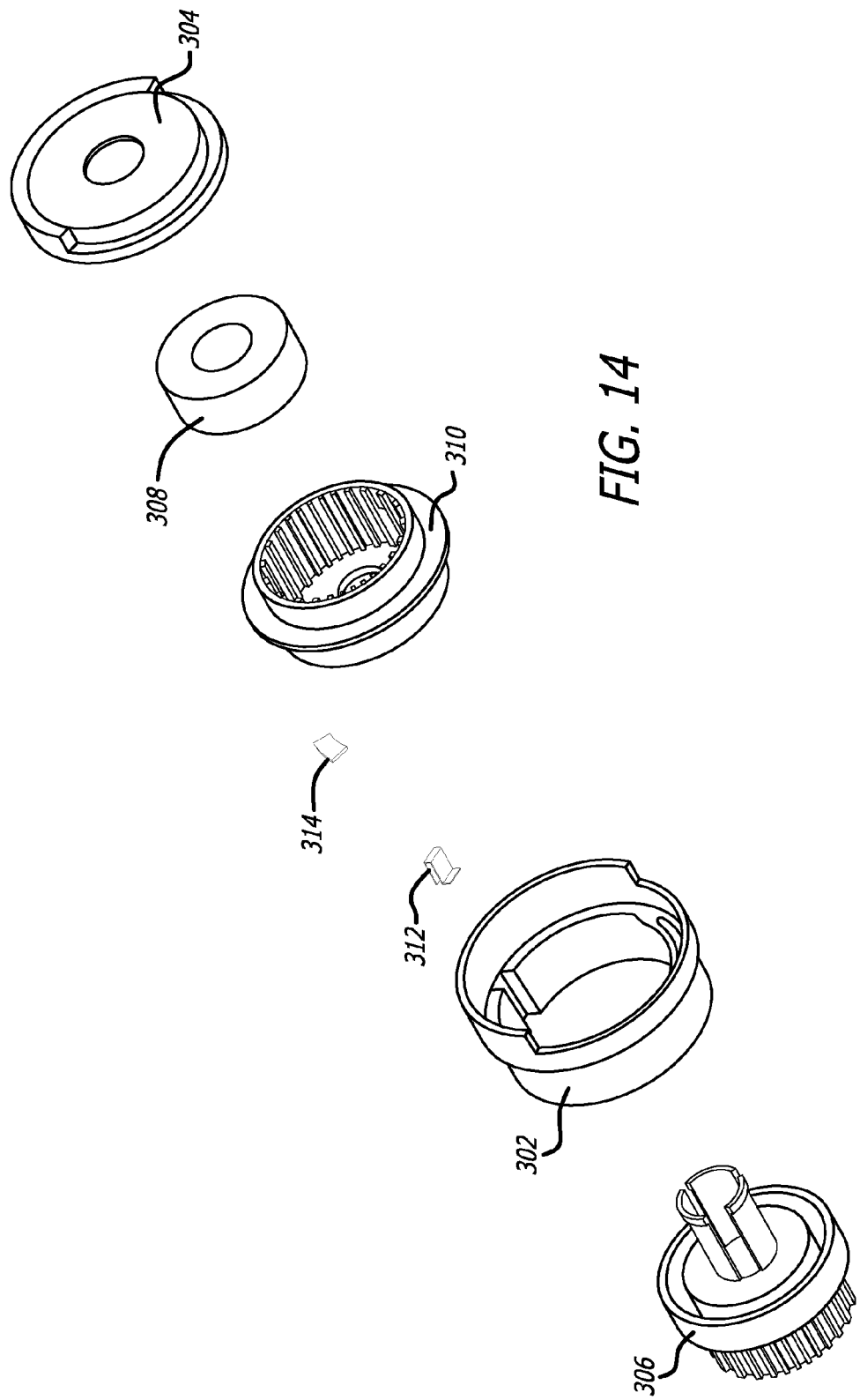
FIG. 14 is an exploded view, depicting components of the cartridge assembly.

Details of the cartridge assembly 122 are depicted in FIGS. 12-14. A generally circular profiled suture spool sleeve 302 forms an outer structure of the cartridge assembly 122. Between a generally disk shaped suture spool track 304 and a primary knob 306 and within the suture spool sleeve of an assembled cartridge 122, are a tensioning spring 308 and a suture spool 310. As is developed below, the tensioning spring 300 functions to provide a tension on a connector member (e.g., a suture) of an anchor assembly. Various different cartridges can be provided which embody springs having varying tensions associated therewith. Moreover, the system can be configured to provide a different tension when advancing the connector member from that generated subsequent to placement of the anchor assembly at an interventional site. The suture spool 310 is configured to releasably engage the unsheathing pawl 224. Also provided, the function of which is described below, are a knob follower 312 and wire clip 314.

Figure 15:
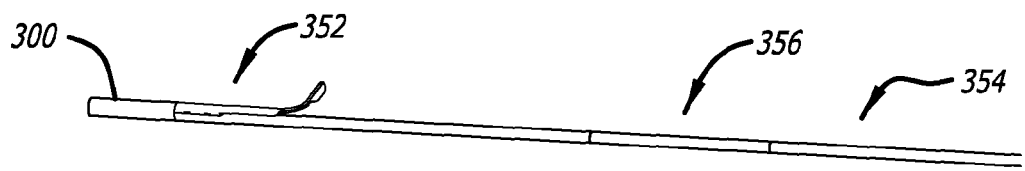
FIG. 15 is a side view, depicting a first component of an anchor and anchoring delivery system.
Figure 16:
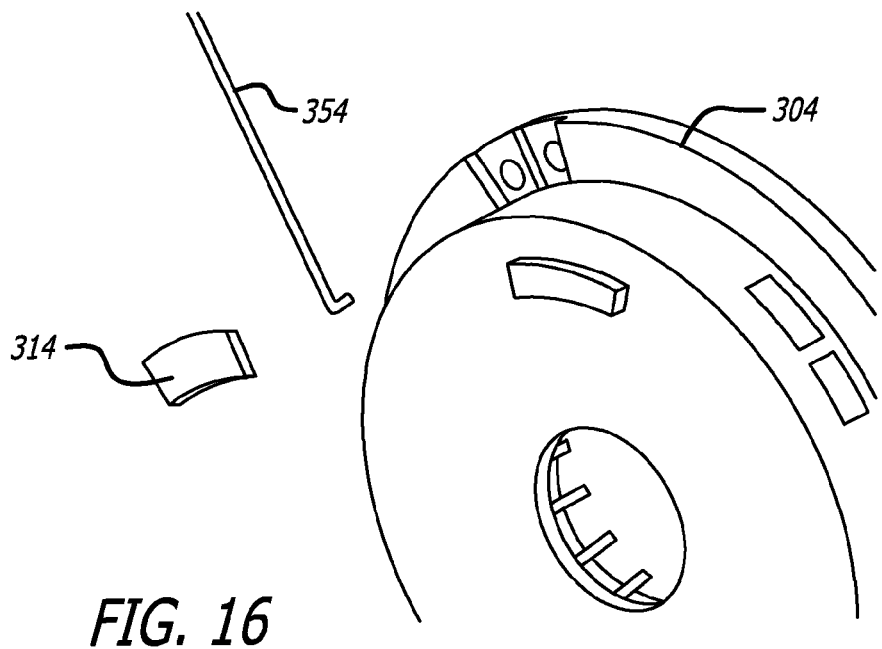
FIG. 16 is a perspective view, depicting components for attaching components of FIG. 15 to a cartridge assembly.
Figure 17:
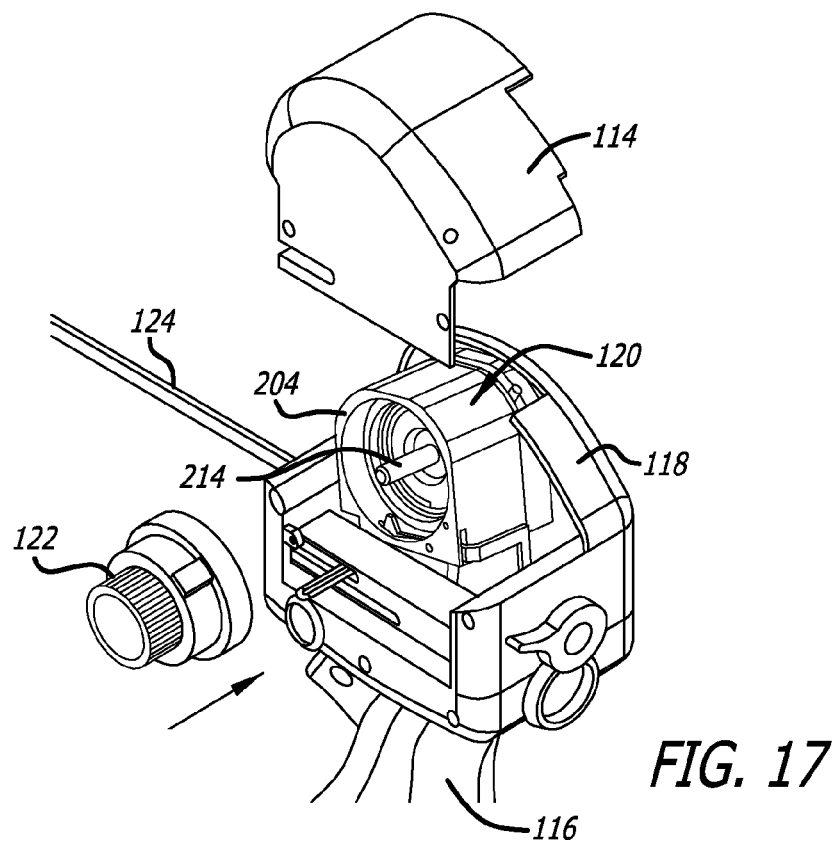
FIG. 17 is a perspective view, depicting replacing a cartridge assembly within an anchor delivery device.
Figure 18:
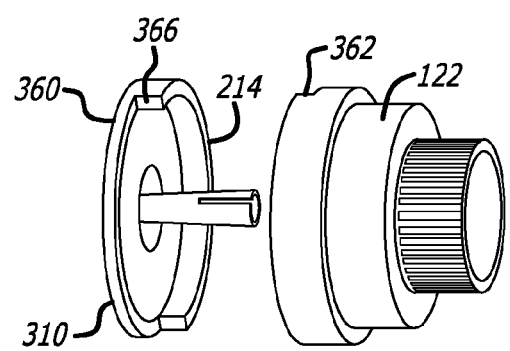
FIG. 18 is a perspective view, depicting attachment of a cartridge assembly to other components of anchor delivery system.
Figure 19:
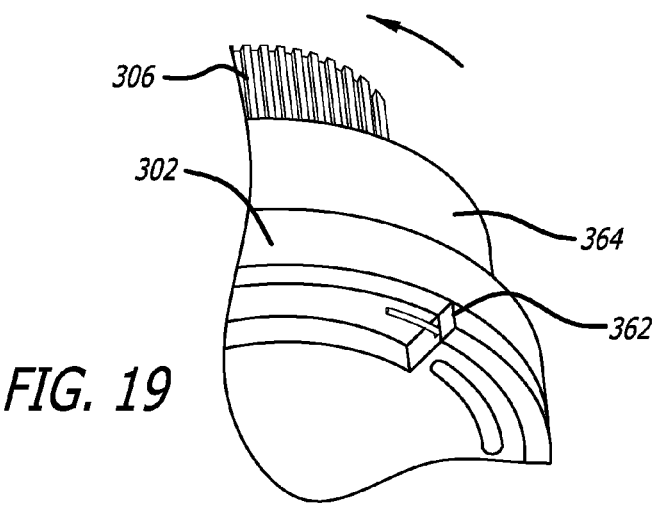
FIG. 19 is a perspective view, depicting loading a portion of an anchor assembly emerging from a cartridge to pass through a needle assembly within a delivery device.
Figure 20:
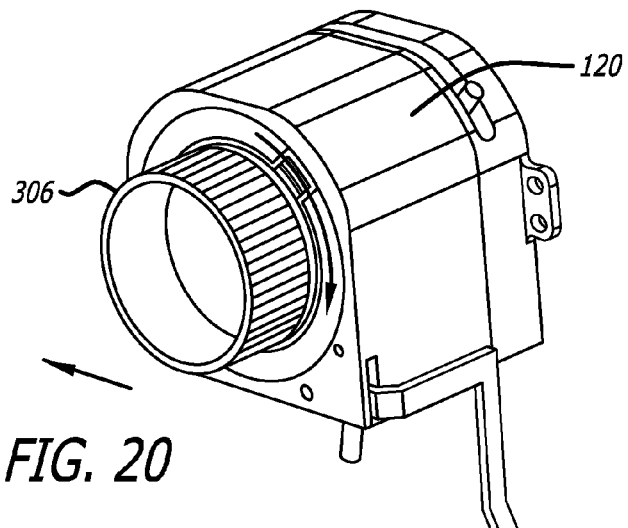
FIG. 20 is a perspective view, depicting a further step involving loading of a cartridge assembly.
Figure 21:
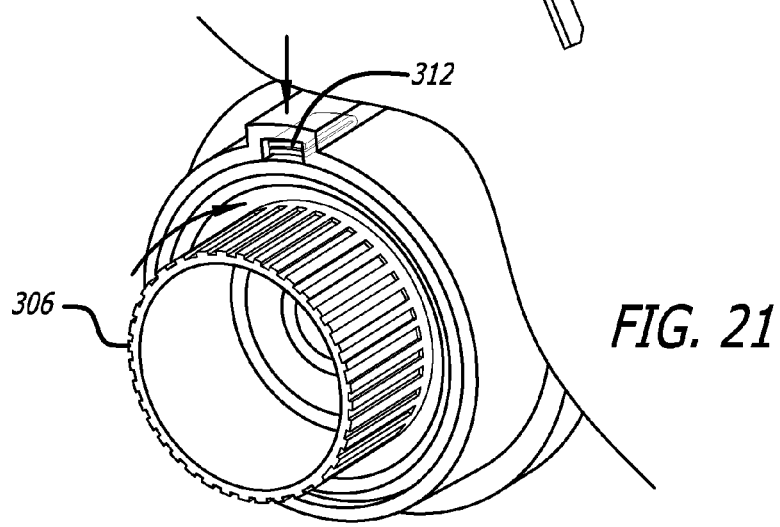
FIG. 21 is a perspective view, depicting yet another step in loading of a cartridge assembly involving advancing a portion of the anchor assembly to a distal end of the delivery device.

One form of a distal anchor 350 and connector member 352 of an anchor assembly is shown in FIG. 15. At a proximal end of the anchor assembly there can be configured a pusher (e.g., a PTFE coated stainless steel wire) 354 attached to the connector member 352 (e.g., a PET monofilament suture) by a sleeve (e.g., polyimide sleeve) 356. It is a proximal terminal end of the pusher 354 which is fixed to the suture spool 304 by the wire clip 314 (See FIG. 16). An annular space formed about the suture spool 304 is provided to receive a length of the pusher 354.

Referring now to FIGS. 17-21, a particular advantage of this embodiment is that the cartridge assembly 122 is removable and replaceable. In the preferred embodiment, a door on the case can be opened or an open window can be in the case to provide access to the interior of the delivery device. Alternatively, the left top case 114 can be removed providing access to an interior of the delivery device. When replacing, the cartridge assembly 122 can be placed within an outside recess of the spool housing 204 and into engagement with the needle spool 214. The center post extending from the needle spool 214 helps guide the cartridge assembly 122 perpendicularly to the needle spool 214. Shoulders 360, 362 formed on the needle spool 214 and the cartridge assembly 122, respectively, ensure proper alignment between the pieces. As shown best in FIG. 19, a leading terminal end 364 of an anchor assembly protrudes from a cartridge shoulder 362, a length of the assembly previously being configured about the suture spool. The terminal end 364 of the assembly aligns with and is insertable within a hole 366 formed in a shoulder 360 of the needle spool.

Once inserted, the primary knob 306 of the cartridge assembly 122 is rotated (FIGS. 20-21) to advance the leading terminal end and connector portion of the anchor assembly through the hole 366 then through the length of the needle assembly (See FIGS. 10-11). The primary knob 306 is continued to be rotated until the knob follower 312 registers at a completion point to thereby signal that the anchor assembly is fully loaded within the needle assembly and in one embodiment the leading end of the anchor assembly is just proximal the distal opening of the needle.

Figure 22:
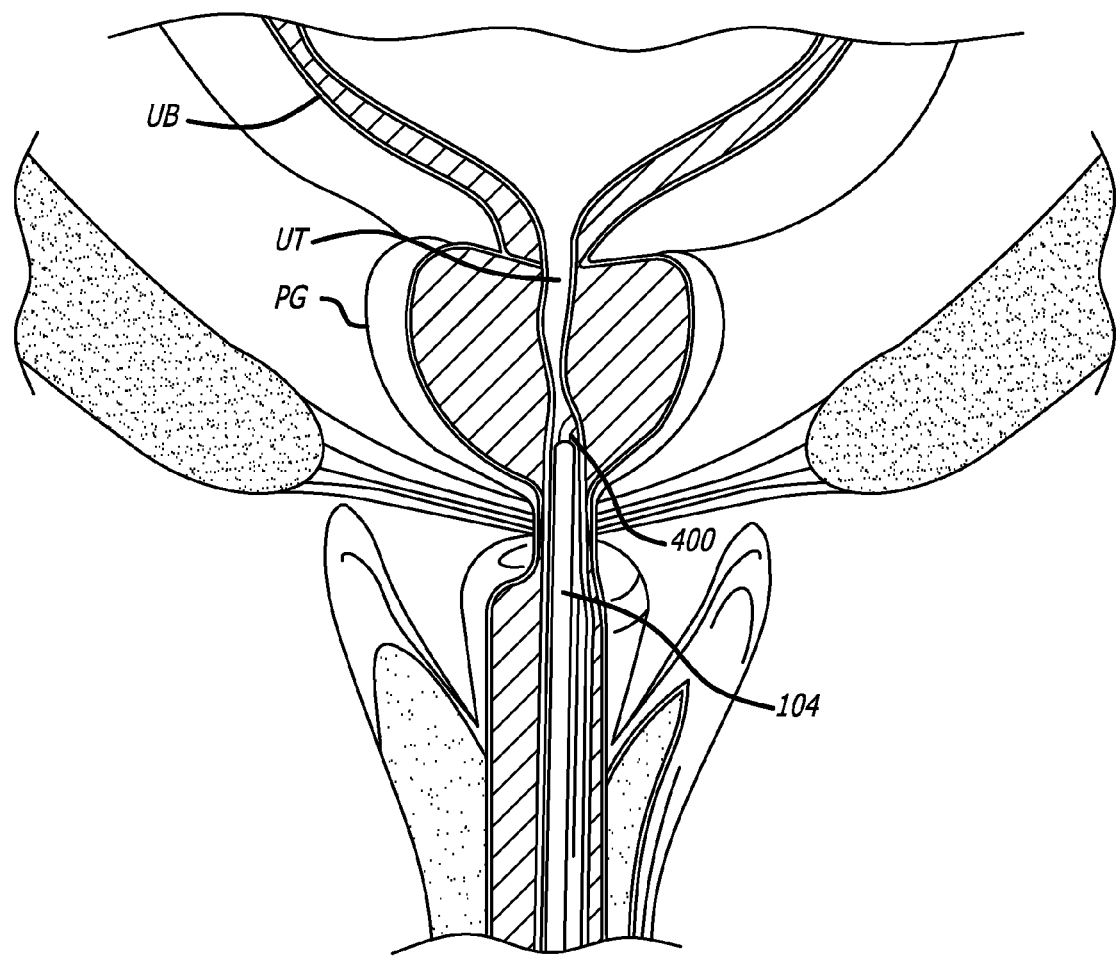
FIG. 22 is a cross-sectional view, depicting a first step involving an interventional procedure.

In one particular, non-limiting use in treating a prostate (See FIG. 22), the elongate tissue access portion 104 of a delivery device is placed within a urethra (UT) leading to a urinary bladder (UB) of a patient. The elongate portion 104 is advanced within the patient until a leading end 400 thereof reaches a prostate gland (PG).

Figure 23:
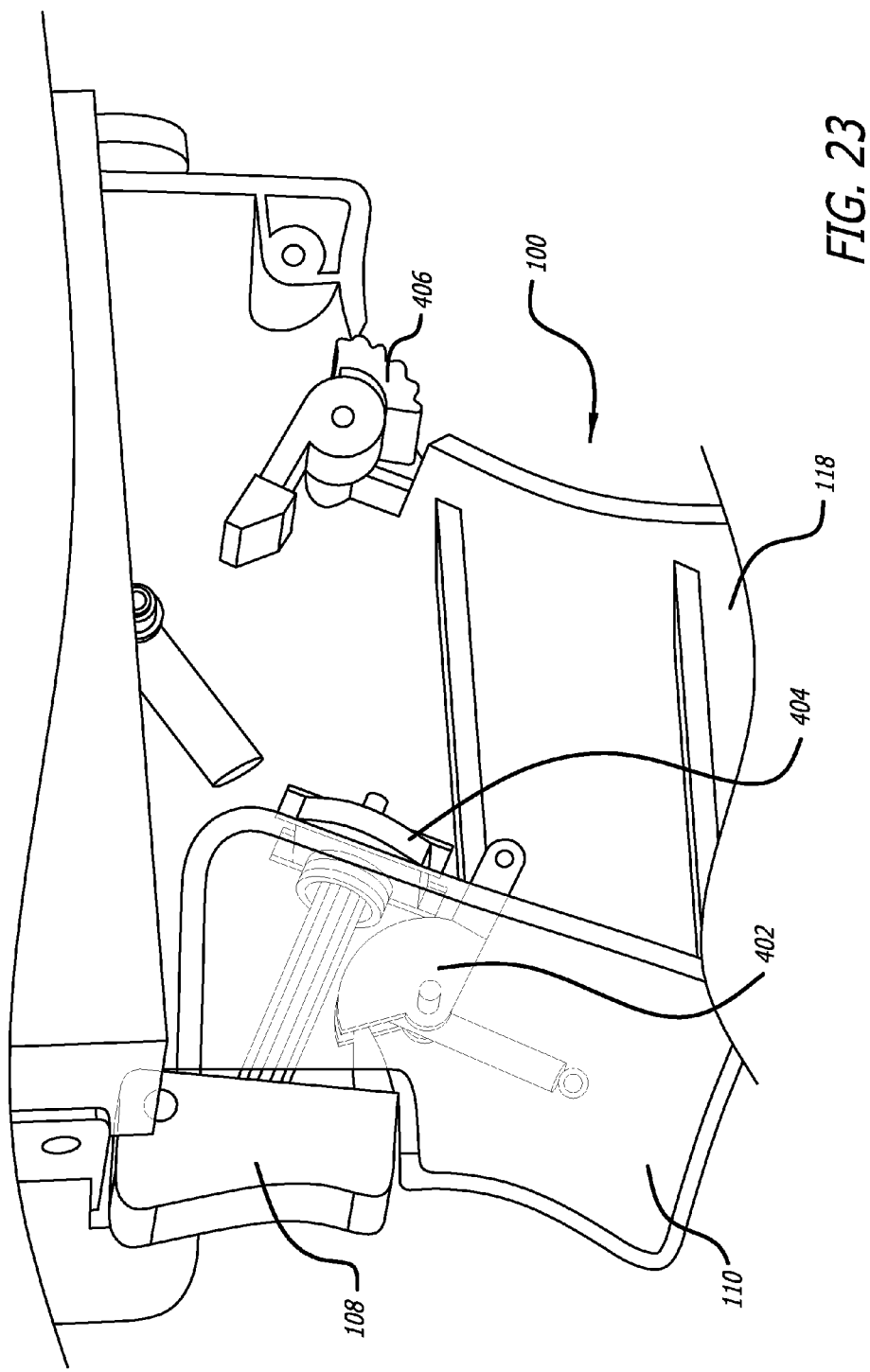
FIG. 23 is a partial cross-sectional view, depicting a delivery device in a non-actuated configuration.
Figure 24:
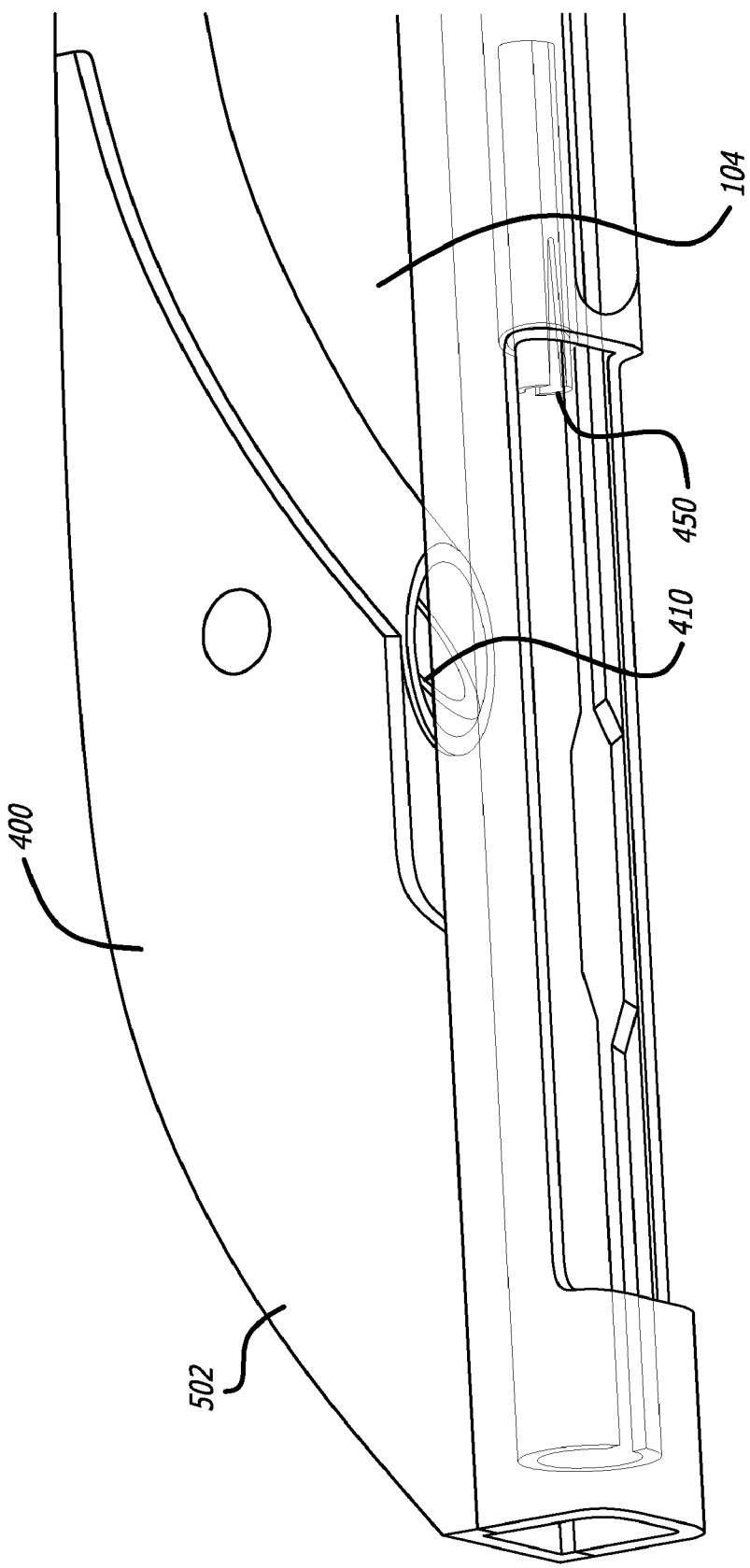
FIG. 24 is a perspective view partially in cross-section, depicting a distal terminal end of a delivery device.

As shown in FIG. 23, the delivery device 100 is at this stage configured in a ready state. The needle actuator 108 and the needle retracting lever 110 are in an inactivated position. The needle actuator 108 is spring biased by a rotating biasing assembly 402. A needle actuator safety (not shown) can be included to lock the needle trigger 108 in an inactive position. Upon depression of the needle actuator 108, a lock-out cam assembly 404 is rotated ninety degrees thereby permitting subsequent actuation of the needle retracting lever 110. The assembly further includes a lever lock 406 configured to hold the depressed needle retracting lever after retraction of the lever 110. It is at this stage also that the terminal end 400 of the elongate portion 104 of the delivery device houses a completely withdrawn needle assembly 410 and further includes a second anchor assembly component 450 registered for later deployment (See FIG. 24).

Figure 25:
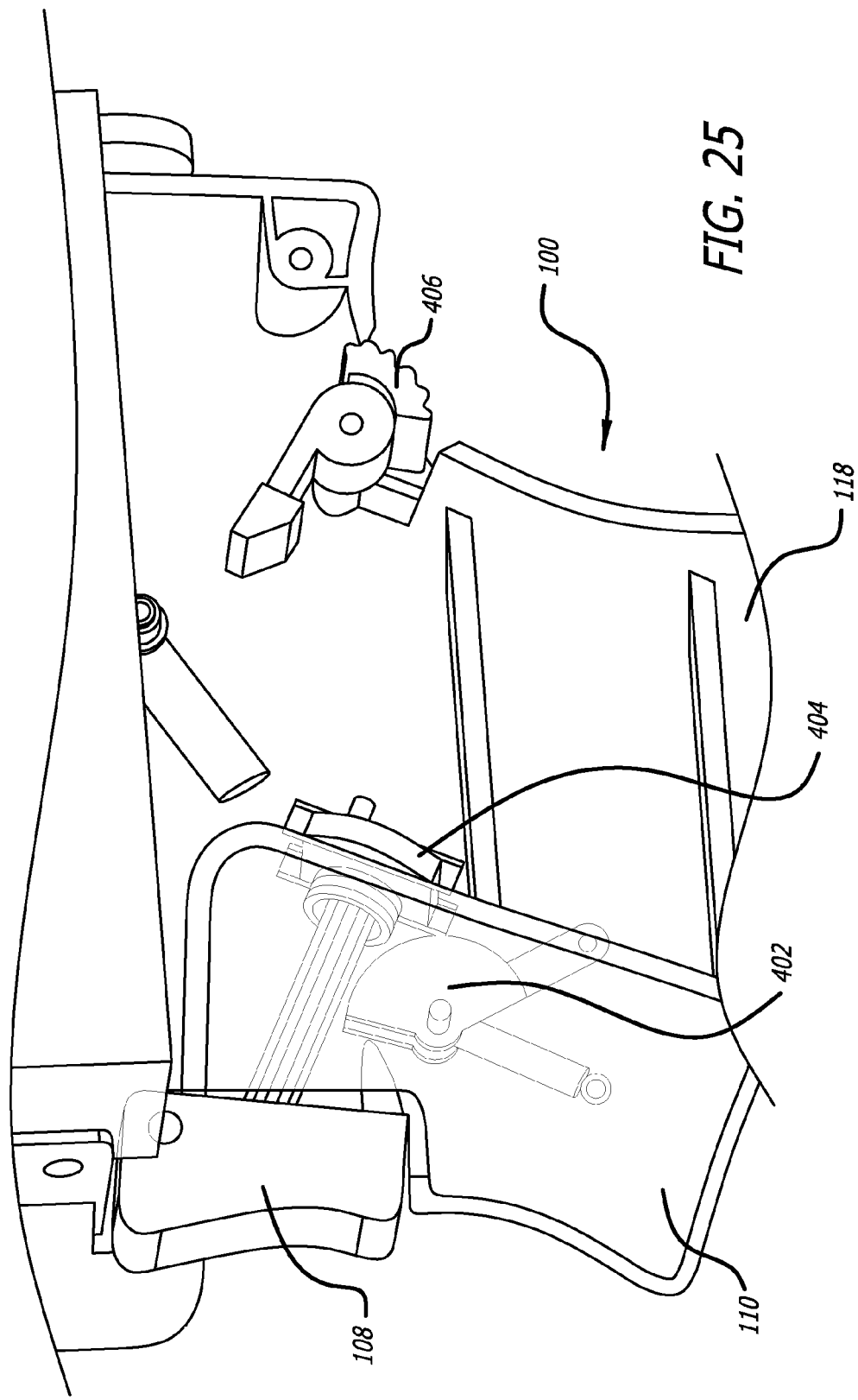
FIG. 25 is a partial cross-sectional view, depicting depression of an actuator of a delivery device.
Figure 26:
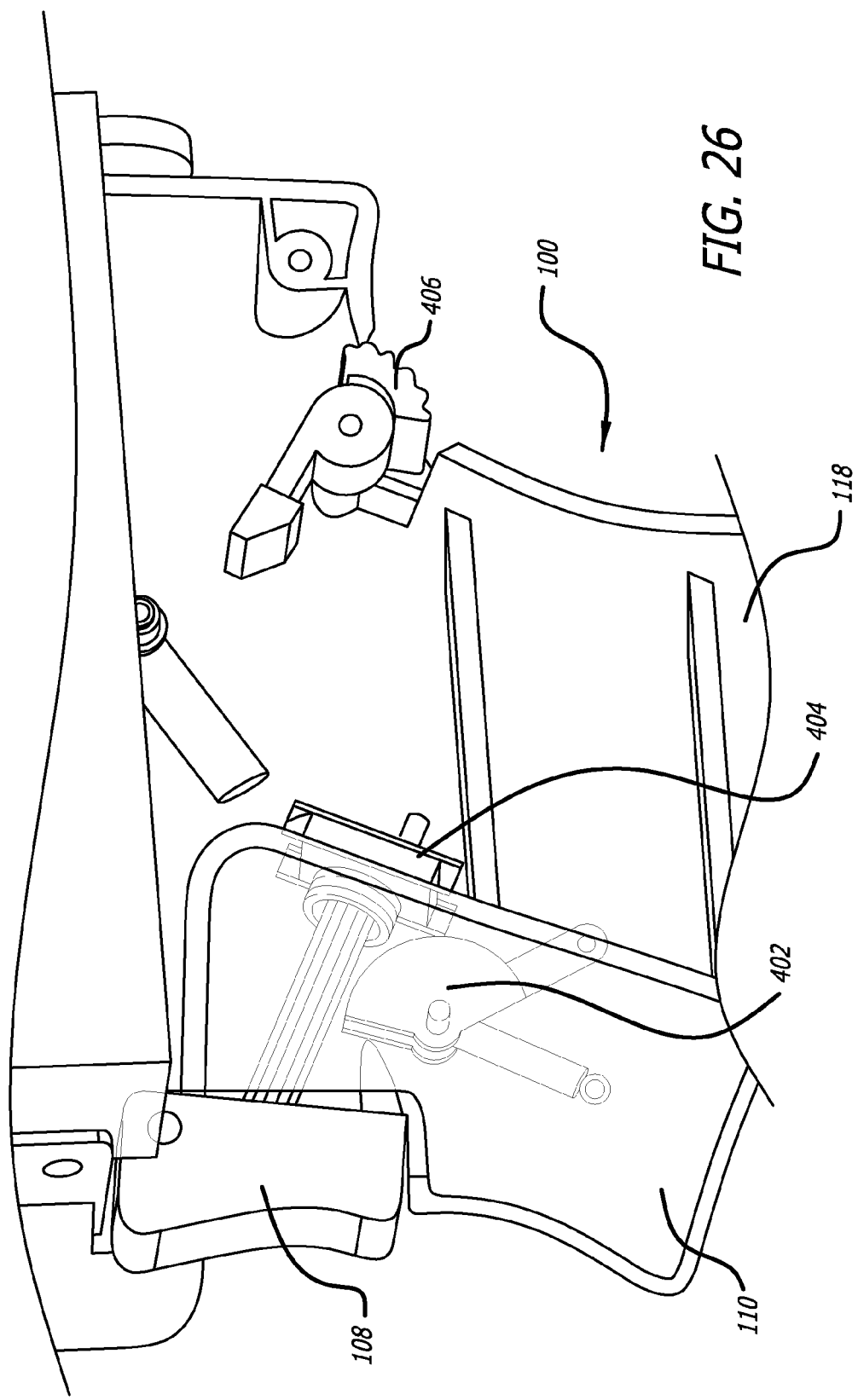
FIG. 26 is a partial cross-sectional view, depicting disengagement of an actuator of a delivery device.

Initial depression of the needle actuator 108 causes components of the biasing assembly 402 to pivot (See FIG. 25). Releasing the needle actuator 108 facilitates it returning to an undepressed condition and permits the lock-out cam assembly 404 to rotate ninety degrees (See FIG. 26). In this position, the lock-out cam assembly 404 is positioned to permit actuation of the needle retraction lever 110.

Figure 27:
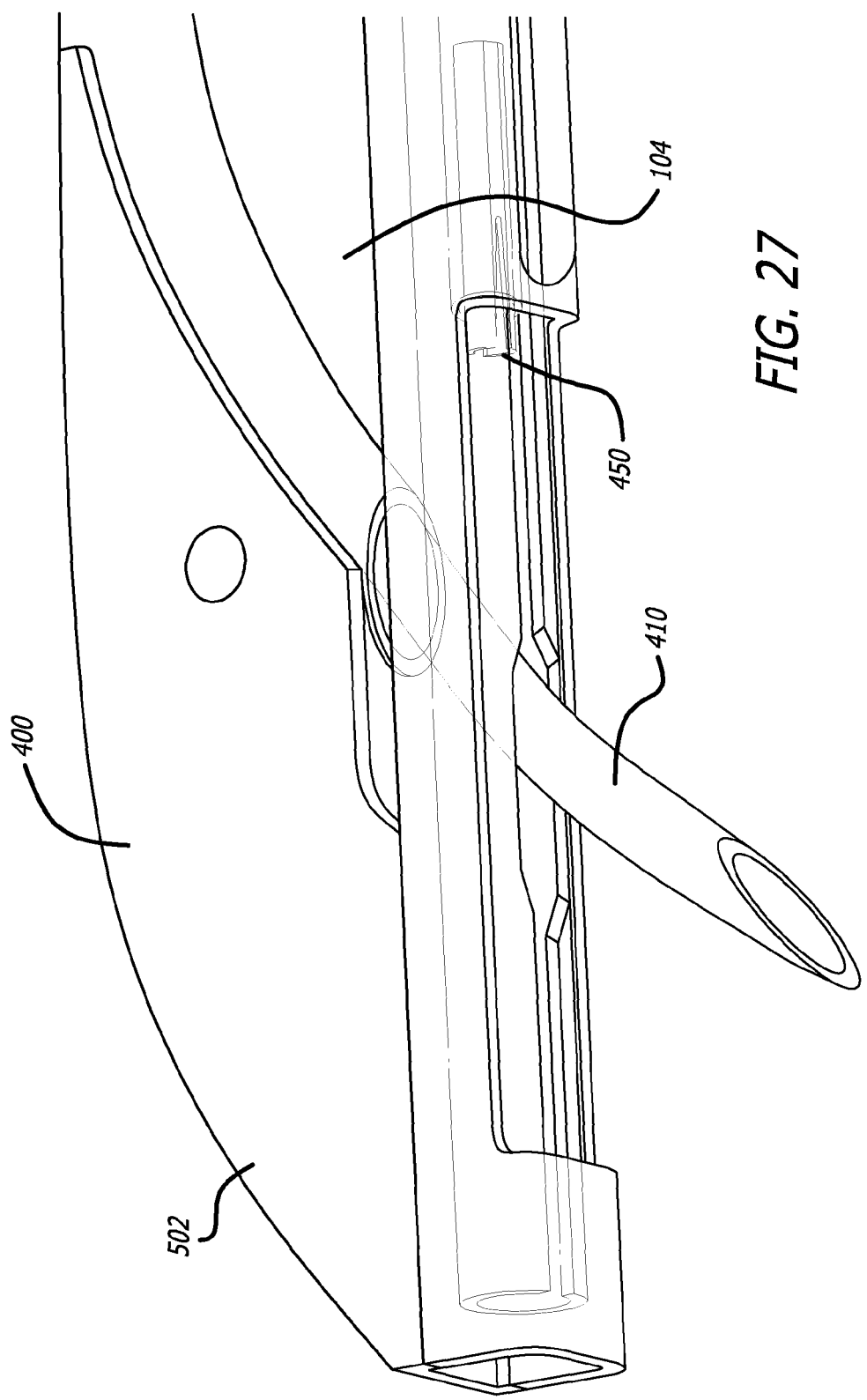
FIG. 27 is a perspective view in partial cross-section, depicting partial ejection of a needle assembly.
Figure 28:
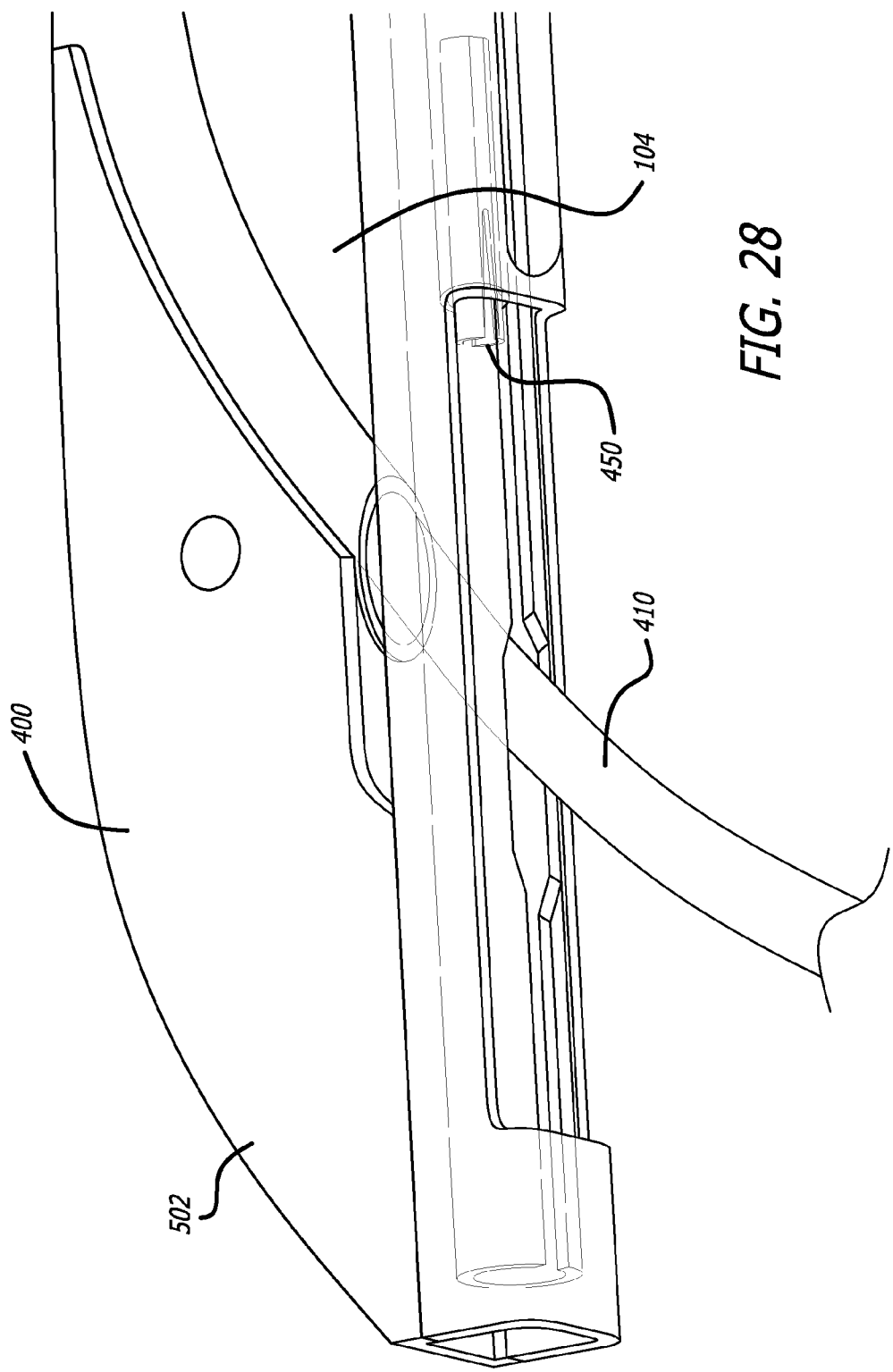
FIG. 28 is a perspective view in partial cross-section depicting complete ejection of a needle assembly ejection.
Figure 29:
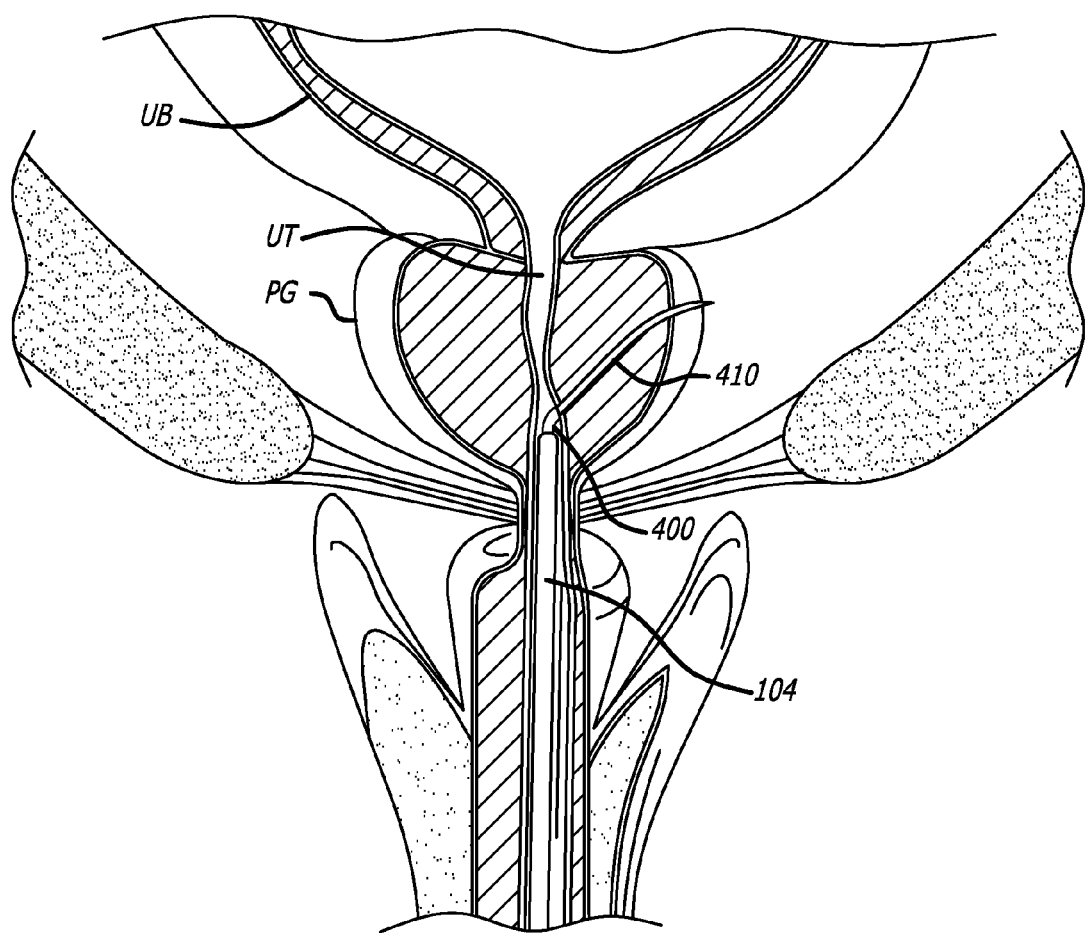
FIG. 29 is a cross-sectional view, depicting advancement of a needle assembly at an interventional site.

At the leading end 400 of the delivery device, as shown in FIGS. 27 and 28, such action results in the needle assembly being advanced from within the elongate member 104. As is to be appreciated, the needle is ejected by the needle deploy spring 206 in this embodiment in a direction commensurate with the direction the handle assembly extends. Moreover, the needle assembly can be configured so that it curves back toward the handle as it is ejected. In use in a prostate intervention (See FIG. 29), the needle assembly 410 is advanced through and beyond a prostate gland (PG). The spring deployment helps to ensure the needle tip passes swiftly through the tough outer capsule of the prostate without "tenting" the capsule or failing to pierce the capsule. In an alternate embodiment, the needle could be manually deployed by the user. In one approach, the needle 410 is made from Nitinol tubing and can be coated with Parylene N. Such a coating helps compensate for frictional or environmental losses (i.e. wetness) which may degrade effectiveness of needle penetration.

Figure 30:
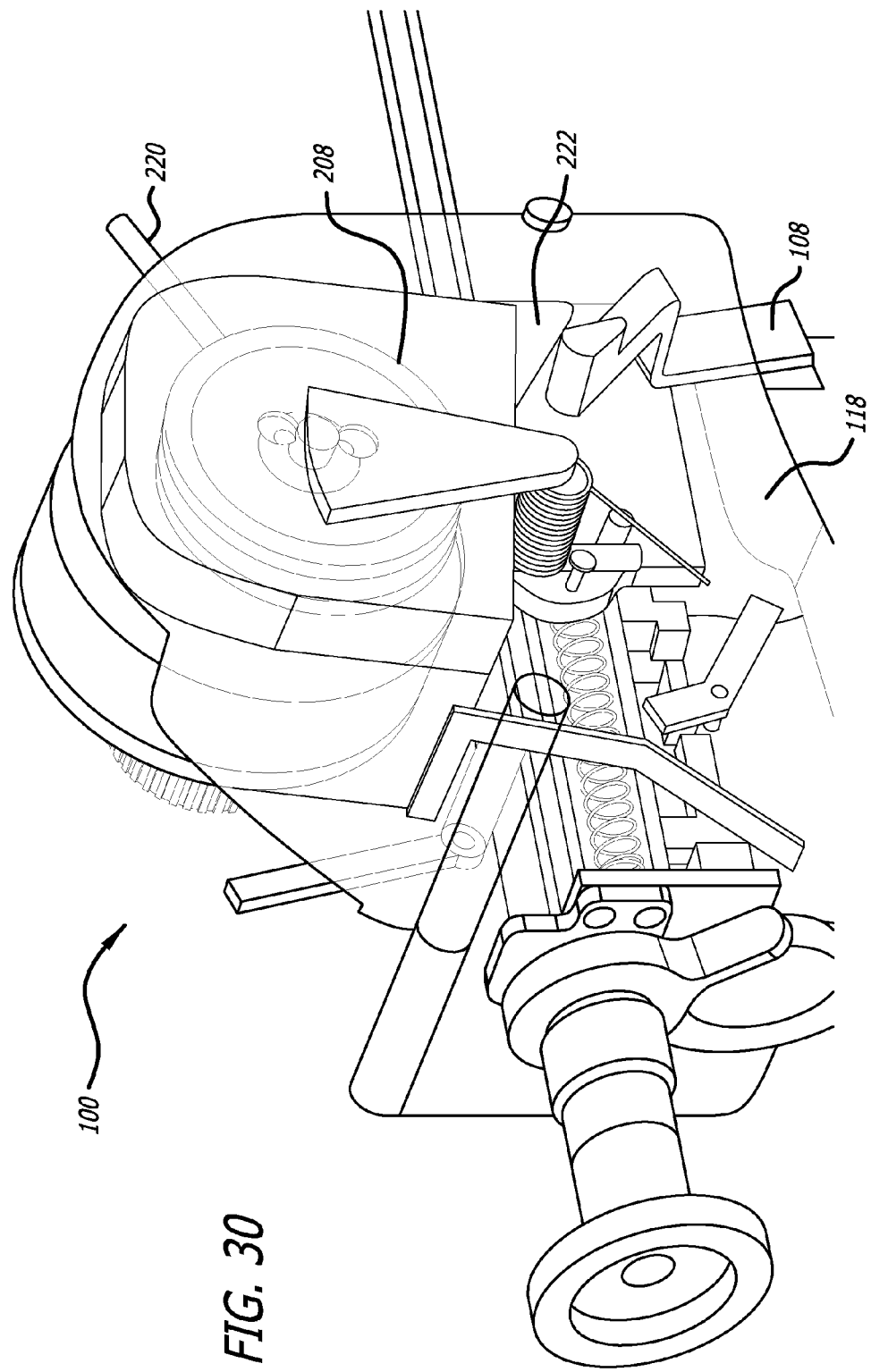
FIG. 30 is a partial cross-sectional view, depicting a delivery device in a ready state.
Figure 31:
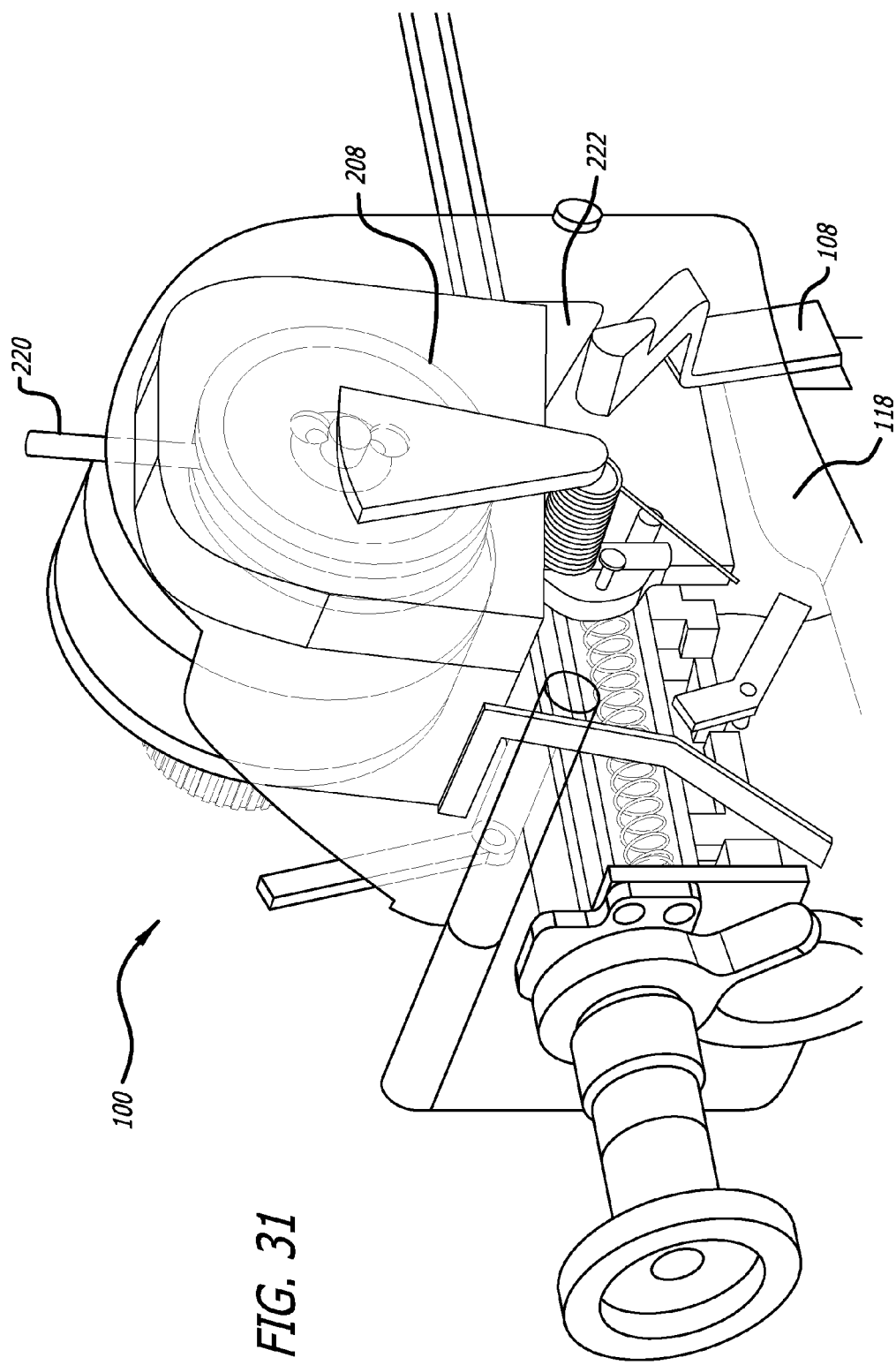
FIG. 31 is a partial cross-sectional view, depicting depression of an actuator of a delivery device.
Figure 32:
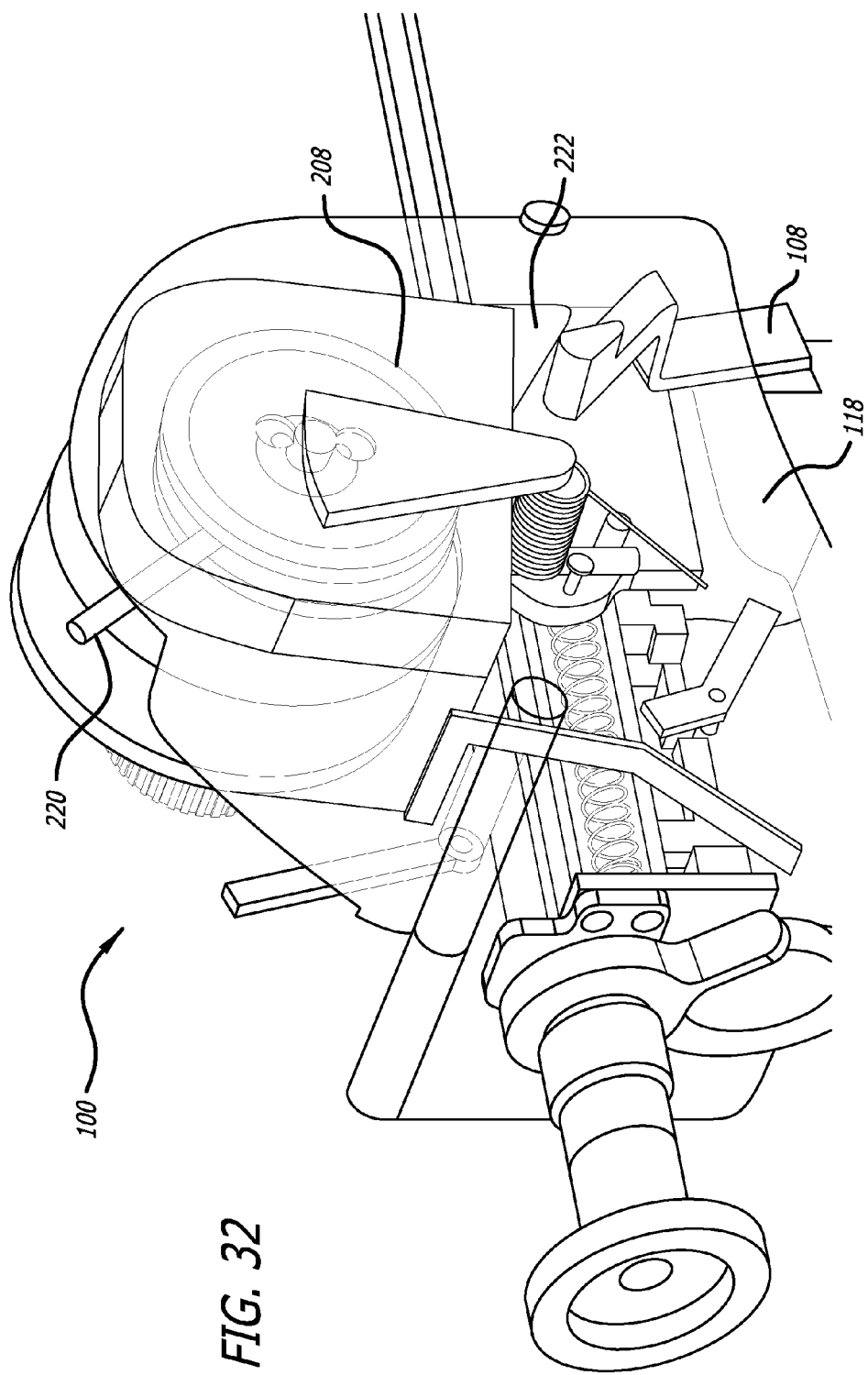
FIG. 32 is a partial cross-sectional view, depicting action of components of a delivery device upon depression of an actuator.

Referring to FIGS. 30-32, the actions of internal sub-components of the delivery device 100 upon actuation of the needle actuator 108 are described. FIG. 30 shows the needle actuator 108 in an unactuated state. As the needle actuator 108 is depressed (FIG. 31), it rotates and an extension thereof engages the needle deploy pawl 222. Continual depression of the needle actuator (FIG. 32) causes the needle pawl 222 to rotate from its engagement with the needle deploy spring arbor 208. This disengagement then permits the needle deploy spring 206 to rotate the needle deploy arbor 208, clutch plate 210, needle clutch cup 212 and needle spool 214 (See FIG. 9). Rotational motion of the needle deploy spring arbor 208 can be observed by noting the change in position of the needle spring reset lever 220. Again, through its connection with a needle assembly, rotation of the needle spool 214 causes the needle assembly to be advanced a desired distance.

Figure 33:
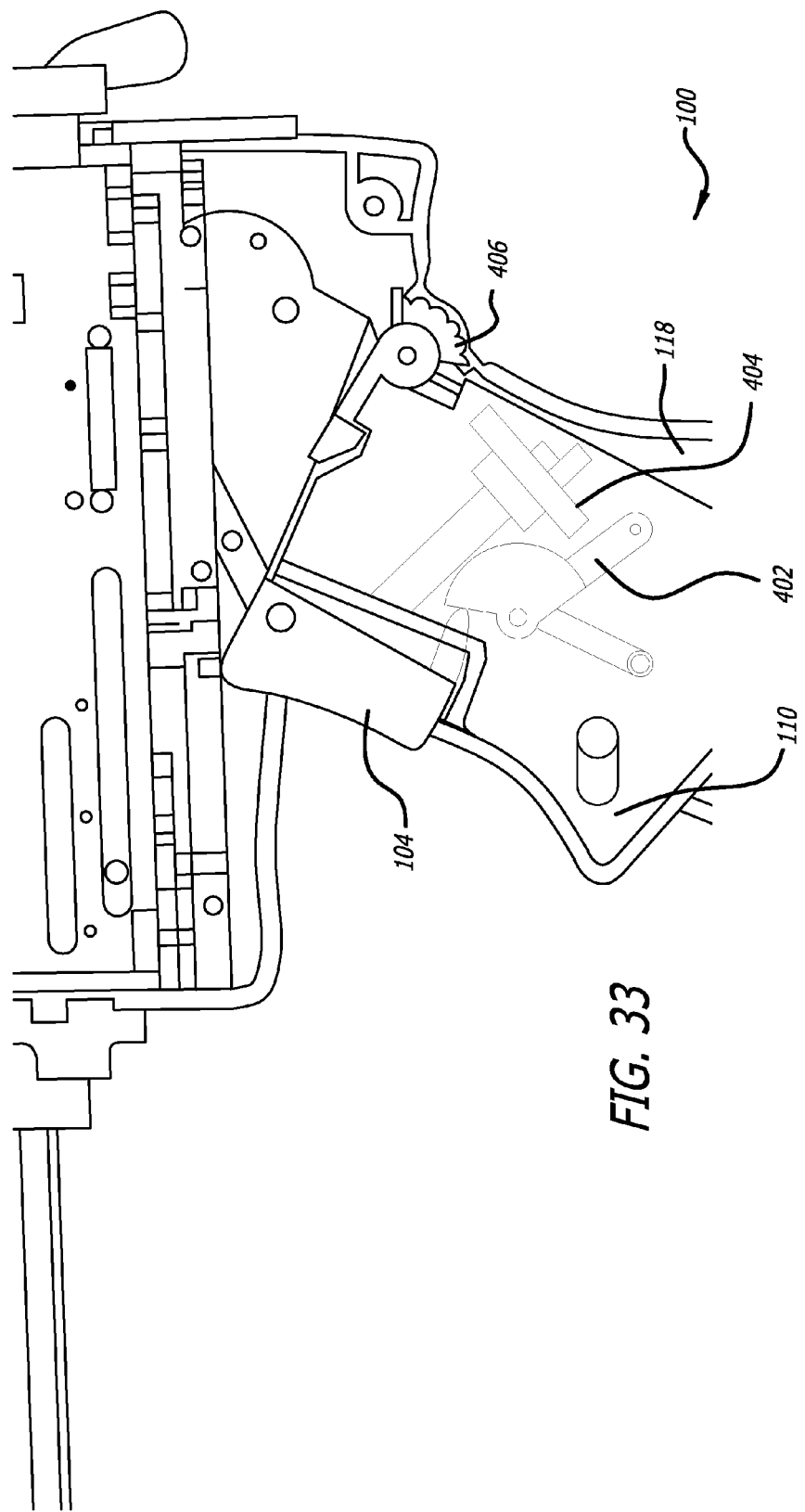
FIG. 33 is a partial cross-sectional view, depicting complete depression of a lever of a delivery system.
Figure 34:
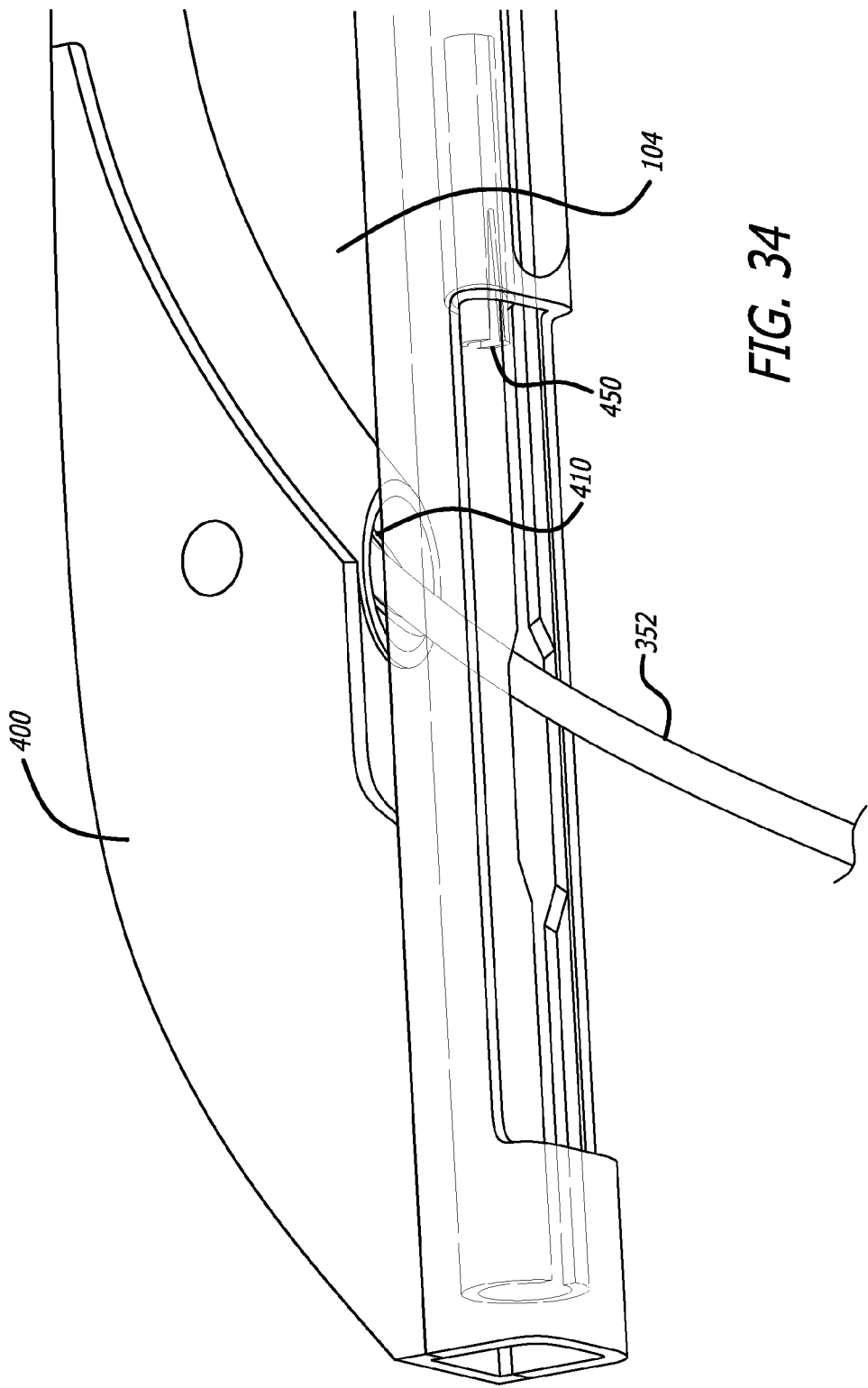
FIG. 34 is a perspective partial cross-sectional view, depicting withdrawal of a needle assembly leaving a connector element.
Figure 35:
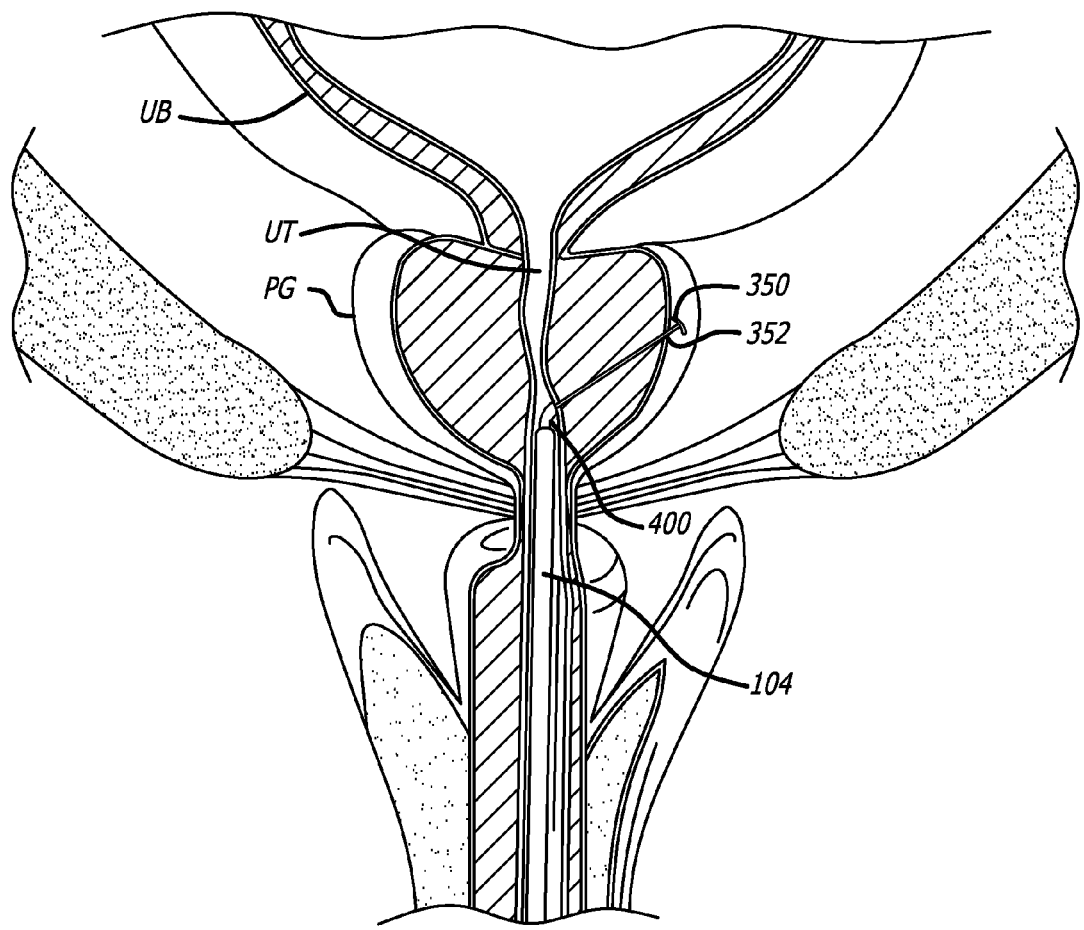
FIG. 35 is a cross-sectional view, depicting delivery of a first component of an anchor assembly at an interventional site.

Next, after complete depression of the needle actuator 108 and the unlocking of the needle retraction lever 110, the needle retraction lever 110 can be completely actuated (See FIG. 33). When so actuated, the lever lock 406 engages and locks the lever 110 in place. The lever lock 406 can be later manipulated to unlock the lever 110. Such action results in a withdrawal of the needle assembly 410, leaving the connector 352 of an anchor assembly in an extended position (See FIG. 34). When extended, the connector 352 extends through the needle window and is centered by suture guide structure. As shown in FIG. 35, in a prostatic interventional procedure, the same results in configuring a first or distal anchor component beyond an outer surface of a prostate gland (PG) with the connector 352 extending toward the terminal end 400 of a delivery device.

Figure 36:
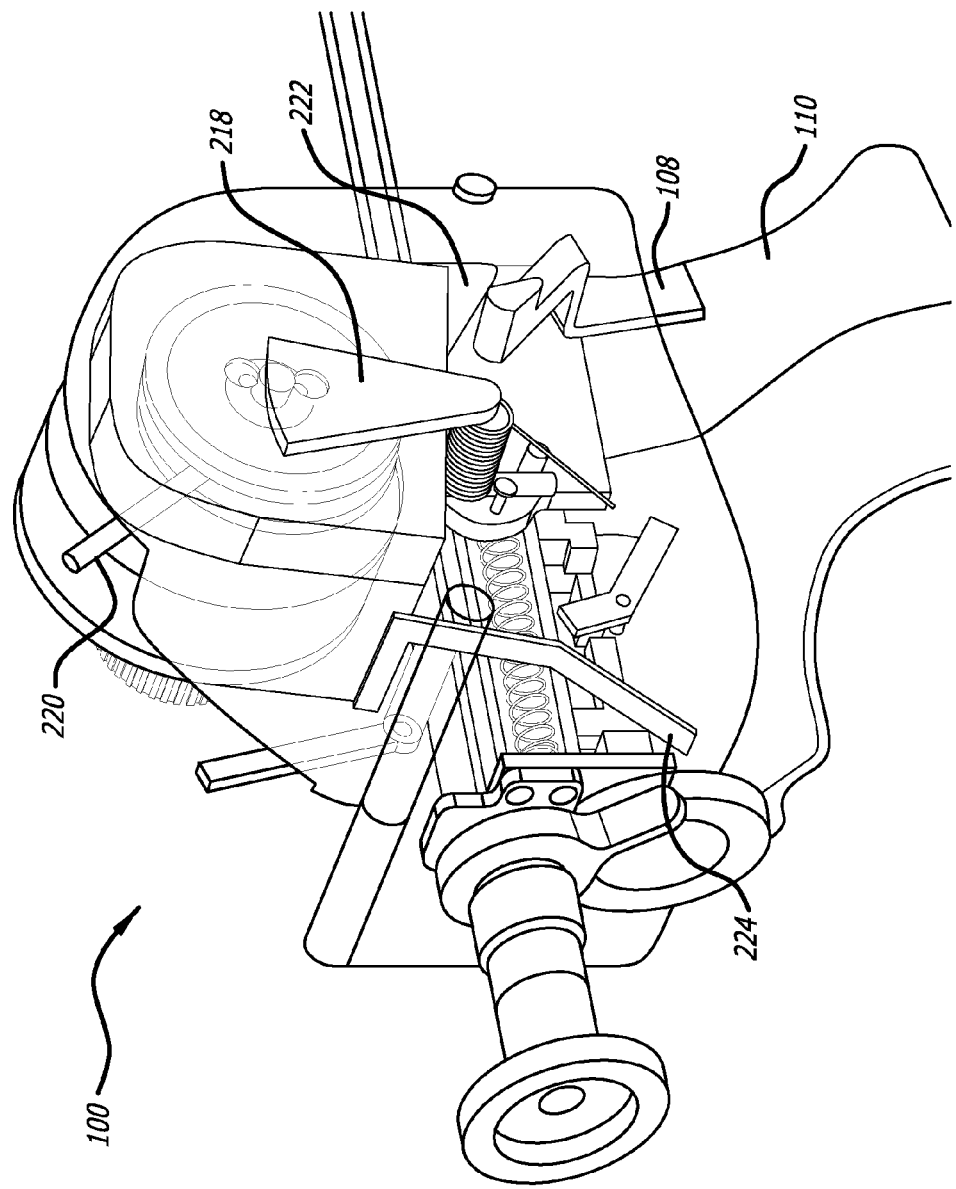
FIG. 36 is a partial cross-sectional view, depicting positional relationships of internal components of the delivery system upon actuation of an actuator.
Figure 37:
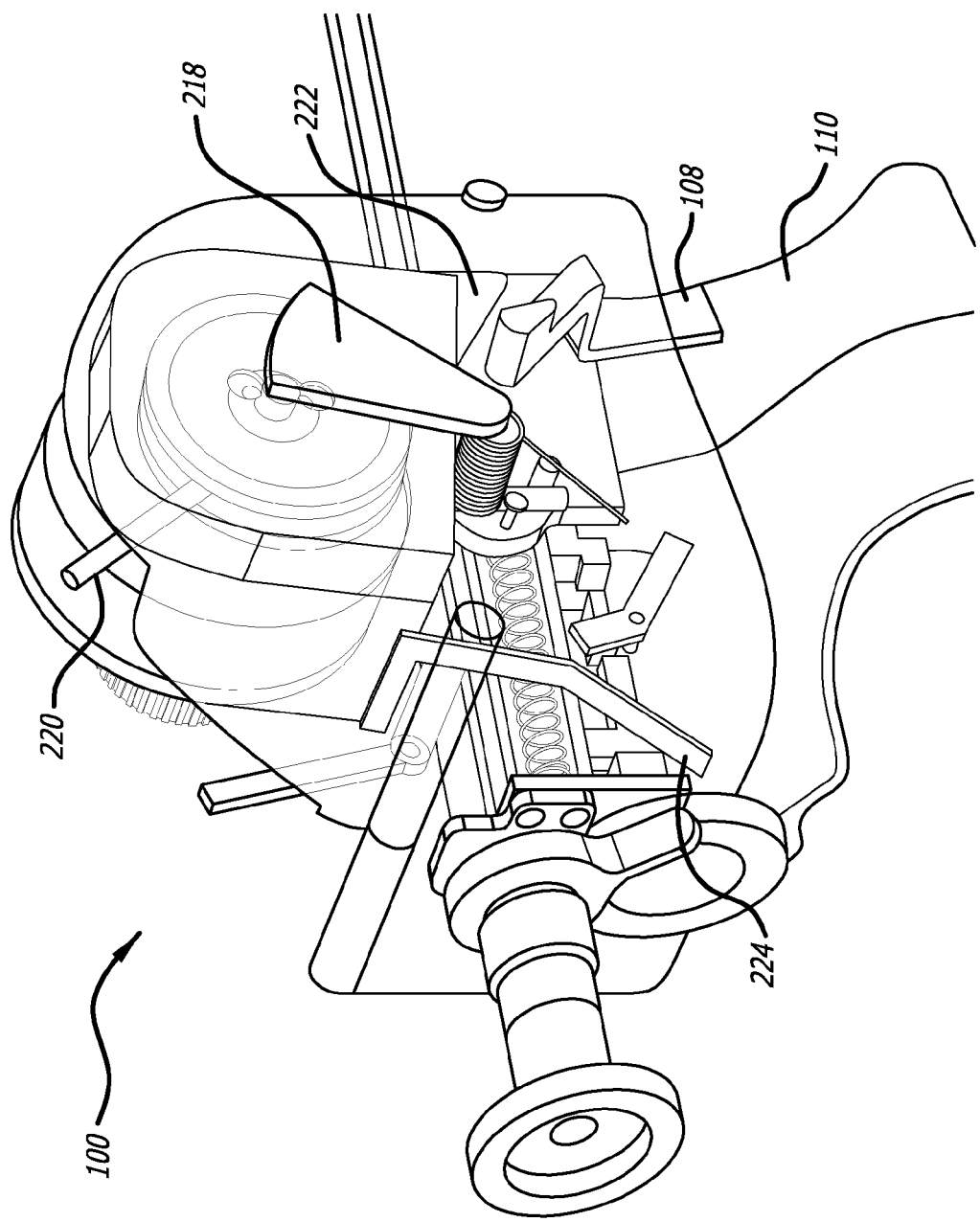
FIG. 37 is a partial cross-sectional view, depicting further action of internal components of the delivery device.
Figure 38:
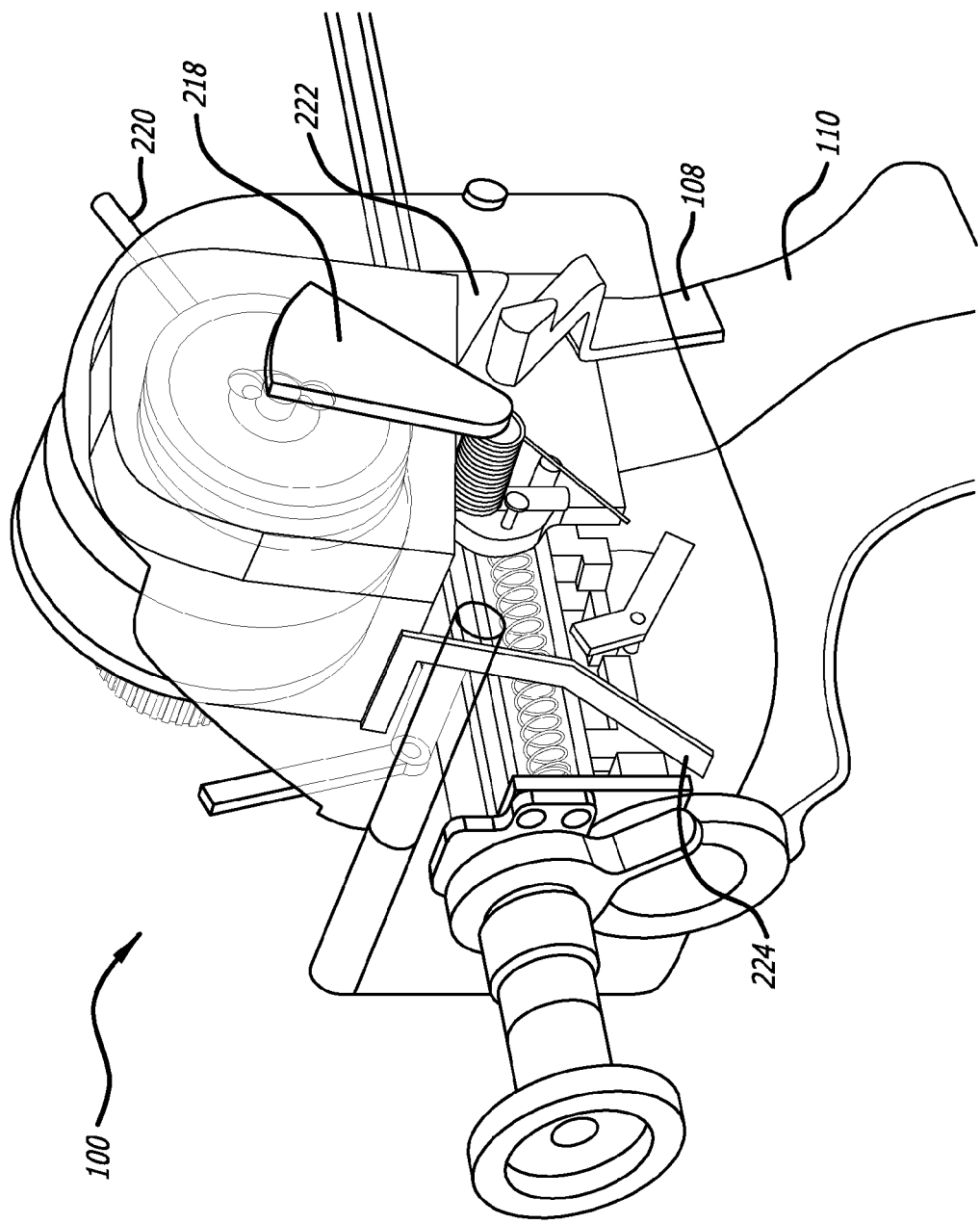
FIG. 38 is a partial cross-sectional view, depicting yet further action of internal components of the delivery device.
Figure 39:
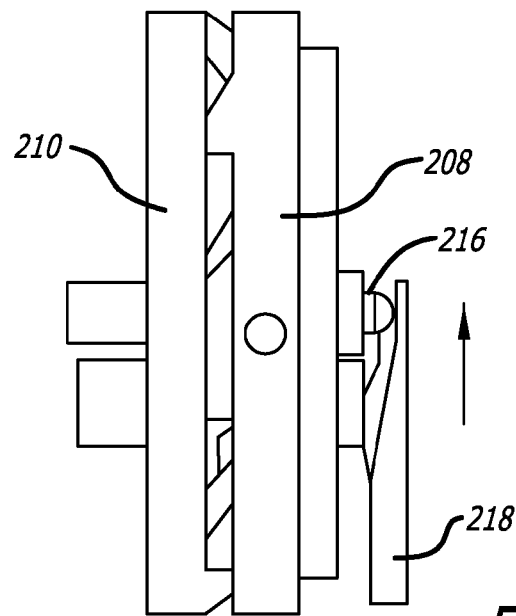
FIG. 39 is a side view, depicting components of a needle drive spool assembly.
Figure 40:
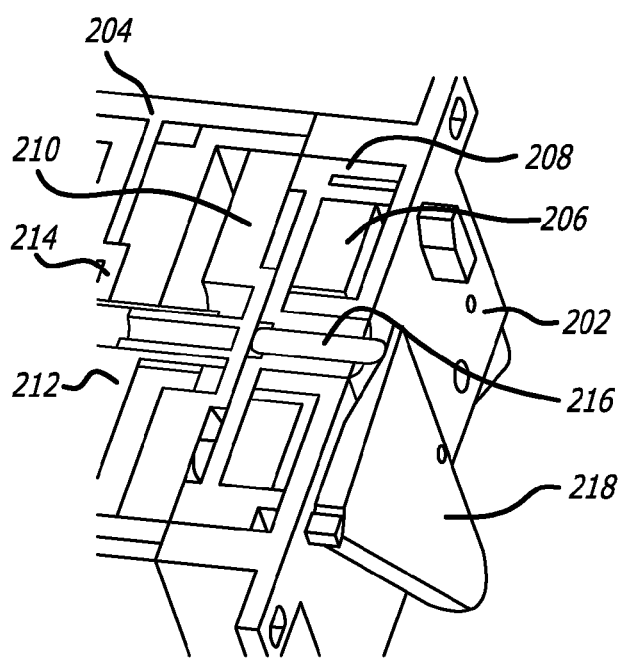
FIG. 40 is a cross-sectional view, depicting components of a needle drive spool assembly.
Figure 41:
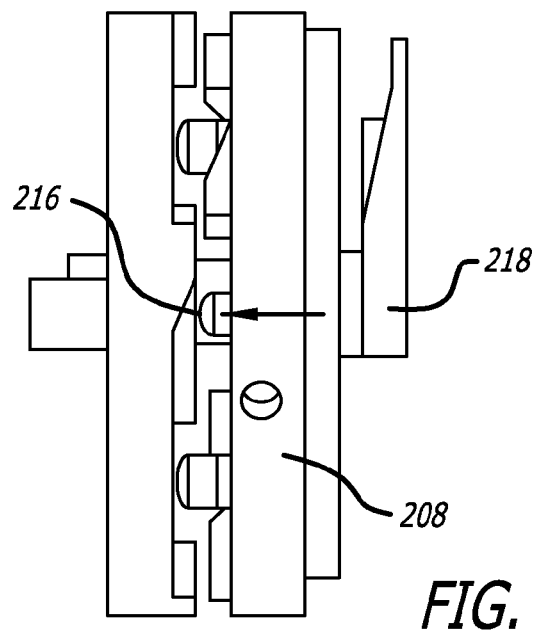
FIG. 41 is a side view, depicting action of components of a spool assembly.
Figure 42:
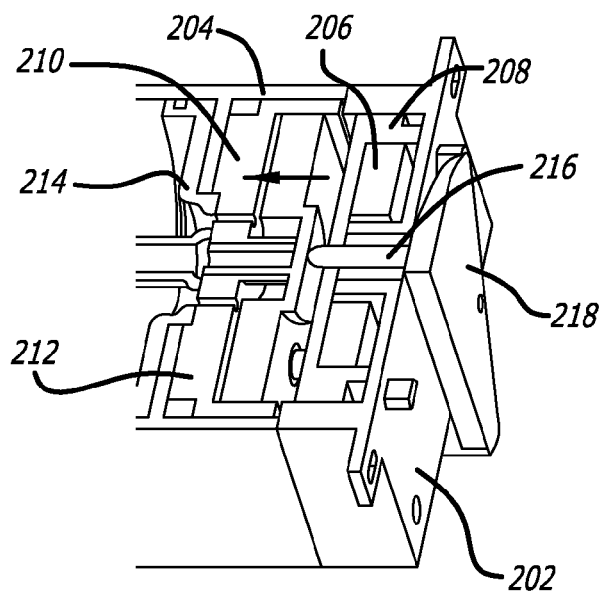
FIG. 42 is a cross-sectional view, depicting the structure of FIG. 41 after actuation.

Internal to the delivery device 100, actuation of the needle retraction lever 110 causes the rotation of the pivotable clutch actuator 218 (See FIGS. 31-38). As shown in FIG. 36, the clutch actuator 218 is in a home position. Upon actuation of the lever 110, the clutch actuator 218 rotates (See FIG. 37).

As best seen in FIGS. 39-42, rotation of the pivotable clutch actuator causes an inclined lever surface thereof to engage the push rod 216. This in turn causes lateral translation of the push rod 216 against the clutch plate 210 as well as a disengagement thereof from the spring arbor 208. This disengagement consequently results in configuring needle spool 214 to allow manual retraction of the needle assembly by manipulating the needle retraction lever 110 and to provide a tension on a connector of an anchor assembly. Manual retraction of the needle provides a simplified approach as well as tactile feedback to the operator to confirm completion of needle retraction. It is to be recognized that such unclutching of the needle deploy spring allows manipulation of the needle retraction lever 110 to be tolerable by the patient and with little to no delivery device tool movement. The tensioning spring 308 provides the tension forces which helps to ensure the distal anchor is pulled back into firm contact with a desired tissue plane such as, for example, the outer capsular surface of the prostate gland. Notably, the spring in a preferred embodiment provides a desired force such as up to 1-2 pounds or more of tension. In another embodiment, a spring can be used to automatically retract the needle assembly.

Figure 43:
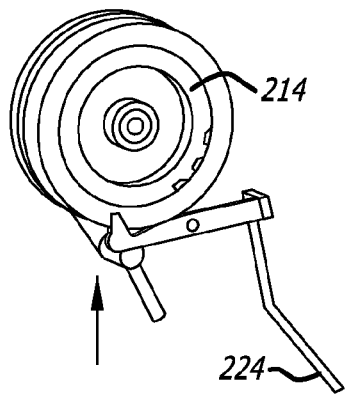
FIG. 43 is a perspective view, depicting components of a cartridge assembly in conjunction with components of a needle drive assembly.
Figure 44:
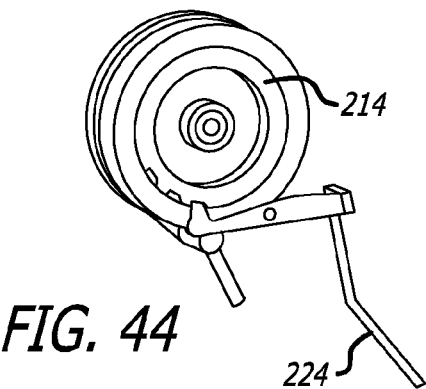
FIG. 44 is a perspective view, depicting the components of FIG. 43 subsequent to action of an actuator.
Figure 45:
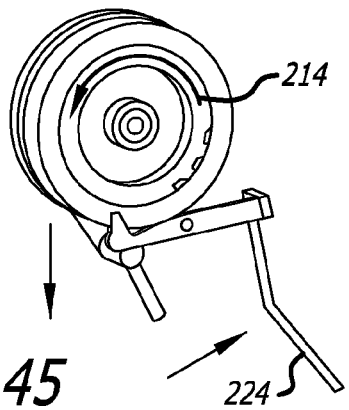
FIG. 45 is a perspective view, depicting further action of the components of FIG. 43 subsequent to action of a retraction lever.
Figure 46:
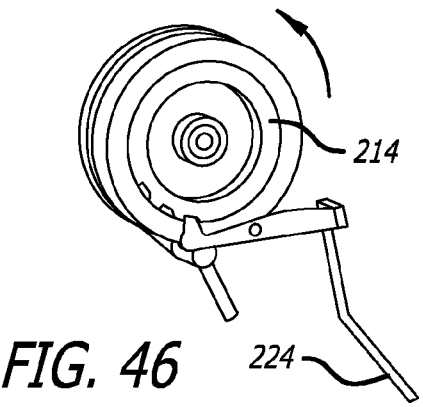
FIG. 46 is a perspective view, depicting yet further action of the components of FIG. 43.

The timing of the needle retraction and tensioning is accomplished through the interaction of the unsheathing pawl 224 and the needle spool 214. As shown in FIGS. 43 and 44, the unsheathing pawl 224 is configured to permit a clockwise rotation of the needle spool which occurs during needle actuator depression until the unsheathing pawl 224 registers within grooves formed in the needle spool. Actuation of the needle retraction lever 110 causes a deflection of the unsheathing pawl 224 (See also FIG. 38) which disengages the unsheathing pawl 224 from the needle spool 214. Since the needle spool 214 is at this point disengaged from the operation of the spring arbor as described above, the needle spool 214 is permitted to rotate in a counterclockwise direction as illustrated in FIG. 46. This counterclockwise rotation continues until the unsheathing pawl 224 again registers in recesses 516 formed in the needle spool 214 (FIG. 46). Such recesses can be spaced to provide desired corresponding needle depths. Also, this structure can be equipped with a roller-clutch (not shown) which would provide a continuous process of longitudinal movement. The tensioning spring of the cartridge assembly 122 (See FIG. 14) is then left to automatically provide a consistent tensioning force on a connector of an anchor assembly. It is at this juncture that the connector gets pulled into suture guide structure 411 (see FIG. 34) to center the connector and ready it for engagement with a second anchor component. Such tensioning results in seating a distal or first anchor component 350 as desired within an interventional site such as shown in FIG. 35 as well as to minimize a distance between two anchor members of an implanted anchor assembly. Again, the tension generated after seating the anchor component 350 can be different from that during delivery of the connector of the anchor assembly.

A more detailed description of the shaft assembly and trigger assembly now follow as does a description of the operation of the trigger assembly to achieve assembly of a second or proximal anchor component to a connector of an anchor assembly and release of a complete anchor assembly at the interventional site.

Figure 47:
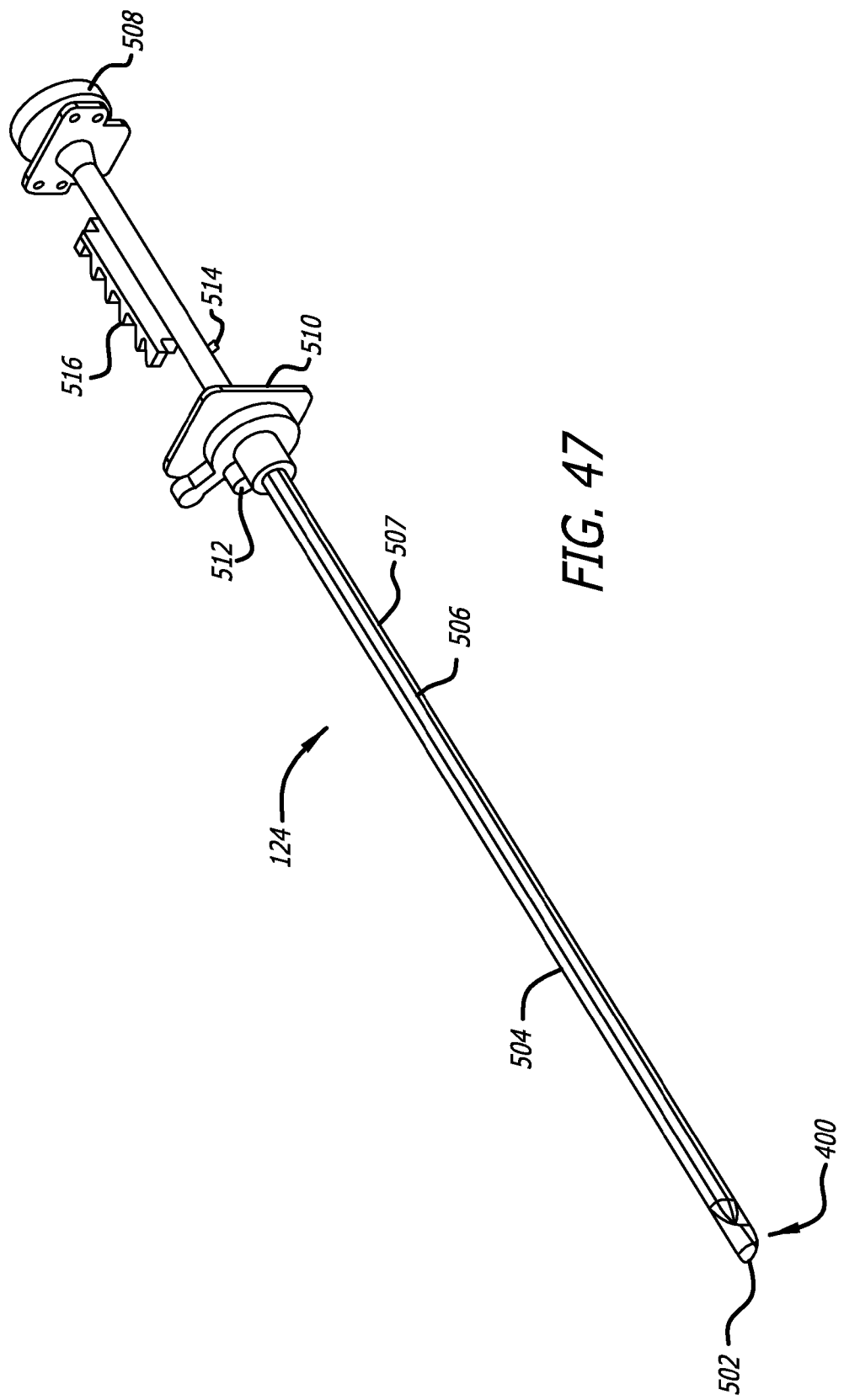
FIG. 47 is a perspective view, depicting a shaft assembly of the delivery device.

With reference to FIG. 47, there is shown an embodiment of a shaft assembly 124. As previously disclosed, a trigger assembly (described below) is mounted to the shaft assembly 124 and the shaft assembly 124 includes components residing within the device case assembly 106 as well as structure extending therefrom. A terminal end portion 400 of the shaft assembly 124 includes an atraumatic tip sleeve 502. Proximally located to the tip sleeve 502 is a tubular shaft assembly 504 which is sized and shaped to slidably receive the needle assembly. A distal end portion of the tubular shaft assembly 504 is curved so that a needle projecting therefrom extends in a direction generally corresponding to that of the handle of the delivery device. Configured longitudinally adjacent the tubular shaft assembly is a scope tube 506 which is sized and shaped to receive a scope. Configured below and longitudinally adjacent the scope tube 506 is an elongate cover 507 which is sized to receive elongate portions of the cutter and pusher assemblies.

At a proximal end of the shaft assembly 124 is a scope mount lock screw assembly 508. A sheath mount assembly 510 including a screw lock 512 is spaced distal and longitudinally from the scope mount assembly 508. Configured between these assemblies are components of a cutter assembly 514 and a pusher assembly 516. It is to be recognized, however, that both the cutter and pusher assemblies include elongate portions extending toward a distal end 400 of the shaft assembly 124.

Figure 48:
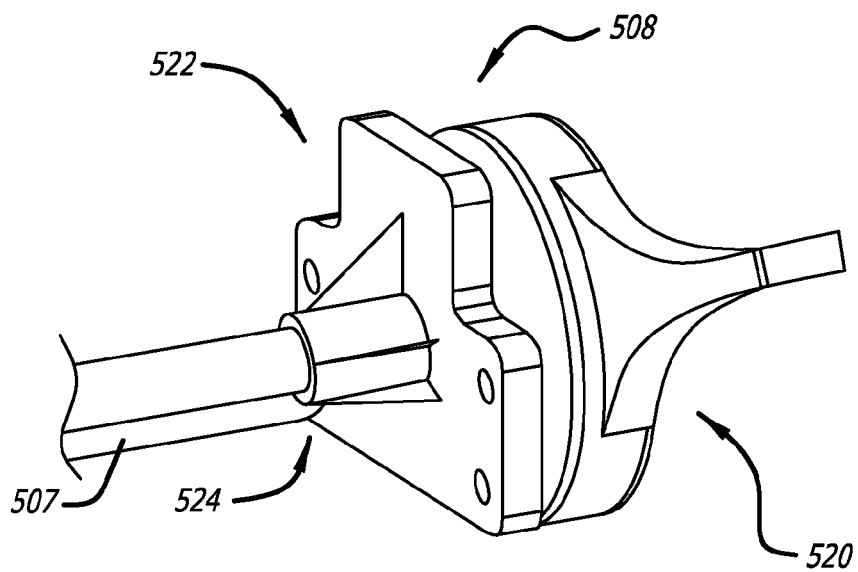
FIG. 48 is a perspective view, depicting structure defining a scope mount.

As shown in FIG. 48, the scope mount lock screw assembly 508 includes a screw lock 520 rotatably positioned adjacent a scope mount receiver 522. The scope mount assembly further includes a handle pusher support snap fit 524. As best seen in previously presented FIGS. 3-5, the scope mount lockingly engages a scope 550 which has a longitudinal dimension sufficient to extend longitudinally substantially a length of the scope tube 506.

Figure 49:
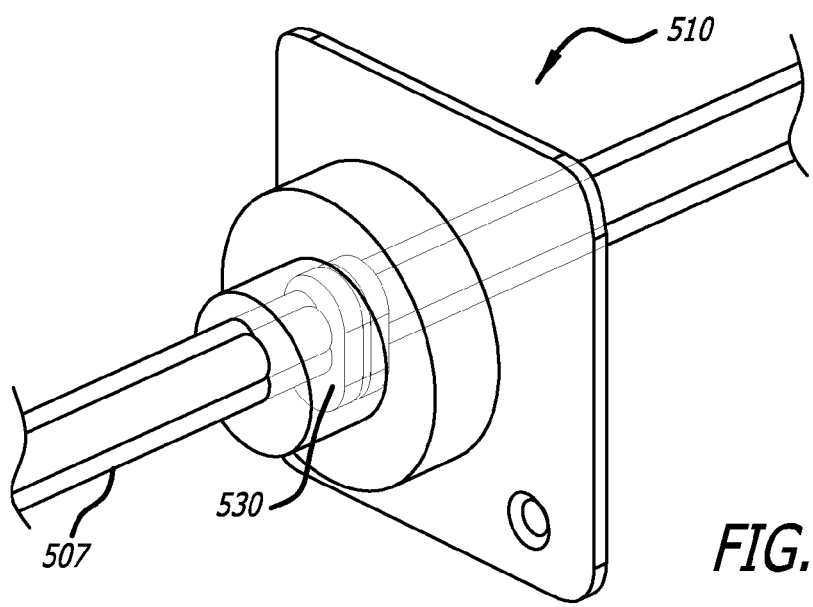
FIG. 49 is a perspective view and partial cross-sectional view, depicting a sheath mount assembly.

The sheath mount 510 can be screwed to elongate portions of the shaft assembly (See FIG. 49). The sheath mount 510 can include a seal 530 which functions to seal and minimize fluid ingress into the handle portion of a delivery device.

Figure 50:
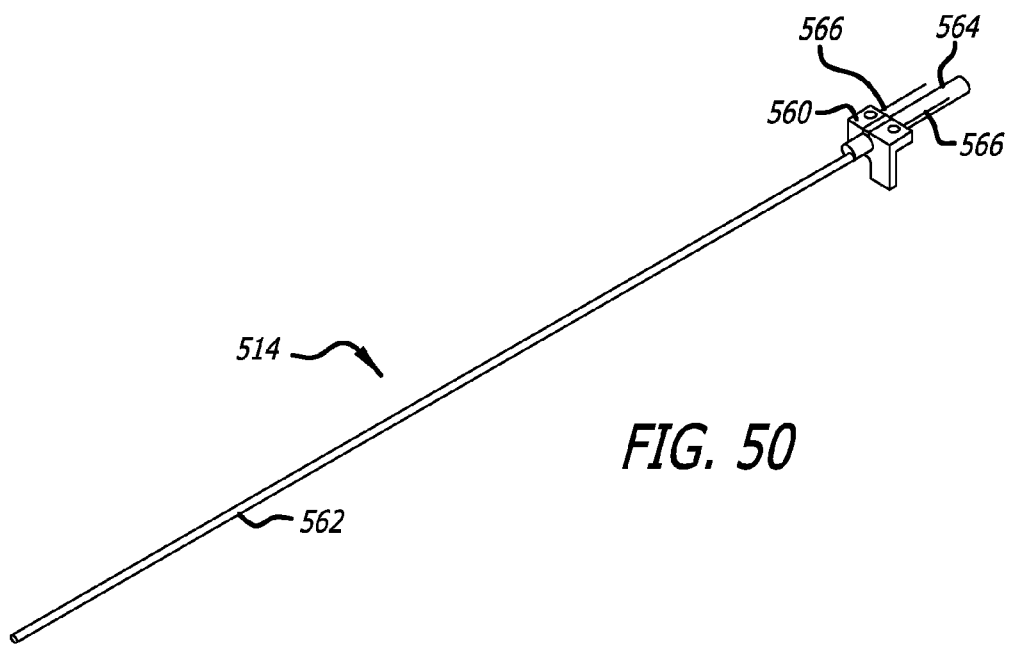
FIG. 50 is a perspective view, depicting a cutter assembly of the delivery device.
Figure 51:
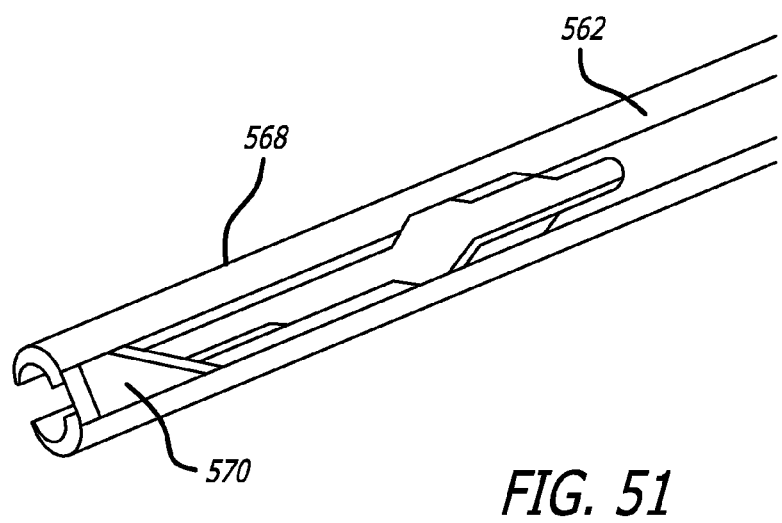
FIG. 51 is a perspective view, depicting a terminal end of the cutter assembly of FIG. 50.

As best shown in FIGS. 50 and 51, an embodiment of the cutter assembly 514 includes a cutter plate 560 supporting a distally directed, elongate cutter tube 562 and a guide 564. A pair of spring extensions 566 are also provided and are each configured to be attached to a cutter spring. A distal end 568 of the cutter tube 562 is configured with a blade so that once cutter springs are permitted to withdraw the cutter assembly 514, the blade can sever as desired a connector of an anchor assembly.

Figure 52:
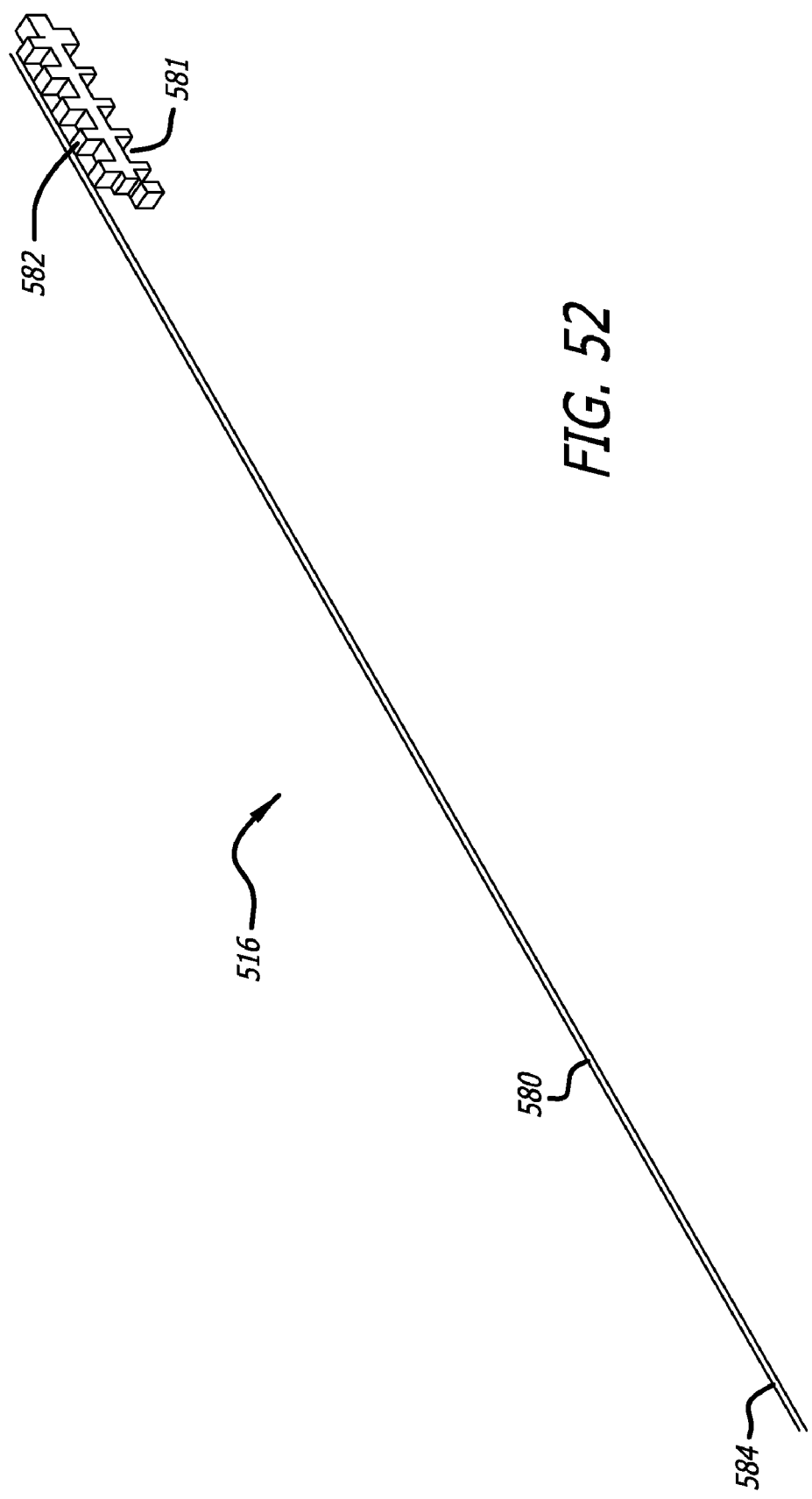
FIG. 52 is a perspective view, depicting a pusher assembly of the delivery device.

With reference to FIG. 52, an embodiment of the pusher assembly 516 of the shaft assembly 124 is described. The pusher assembly 516 includes an elongate pusher member 580 extending from a pusher block 582 to a pusher extension 584. As described in more detail below, the pusher extension 584 engages a proximal end of a second or proximal anchor component. The pusher block 582 further includes a plurality of recesses 586 sized and shaped to receive corresponding structure of the trigger assembly.

Figure 53:
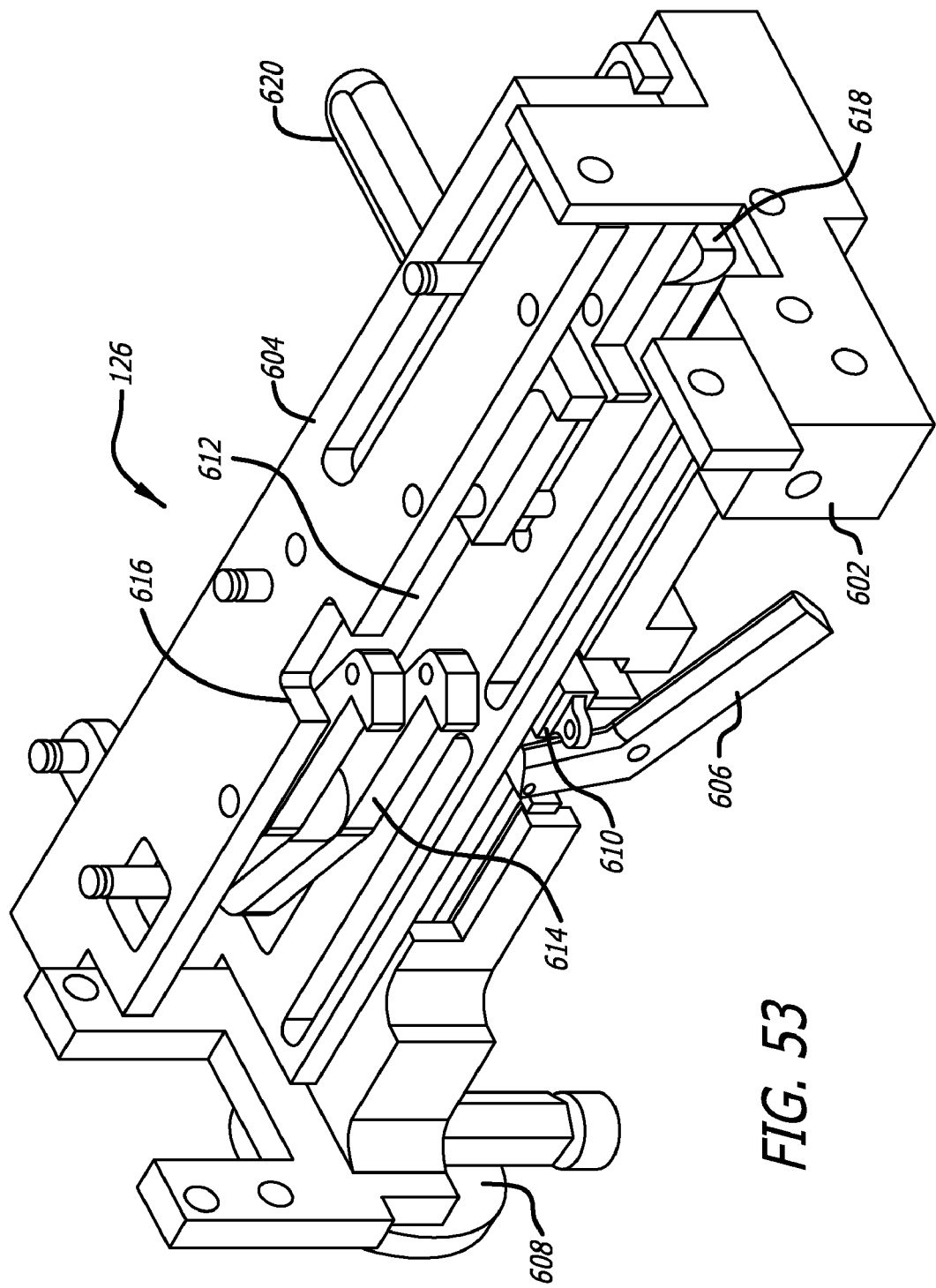
FIG. 53 is a perspective view, depicting a trigger assembly of the delivery device.
Figure 54:
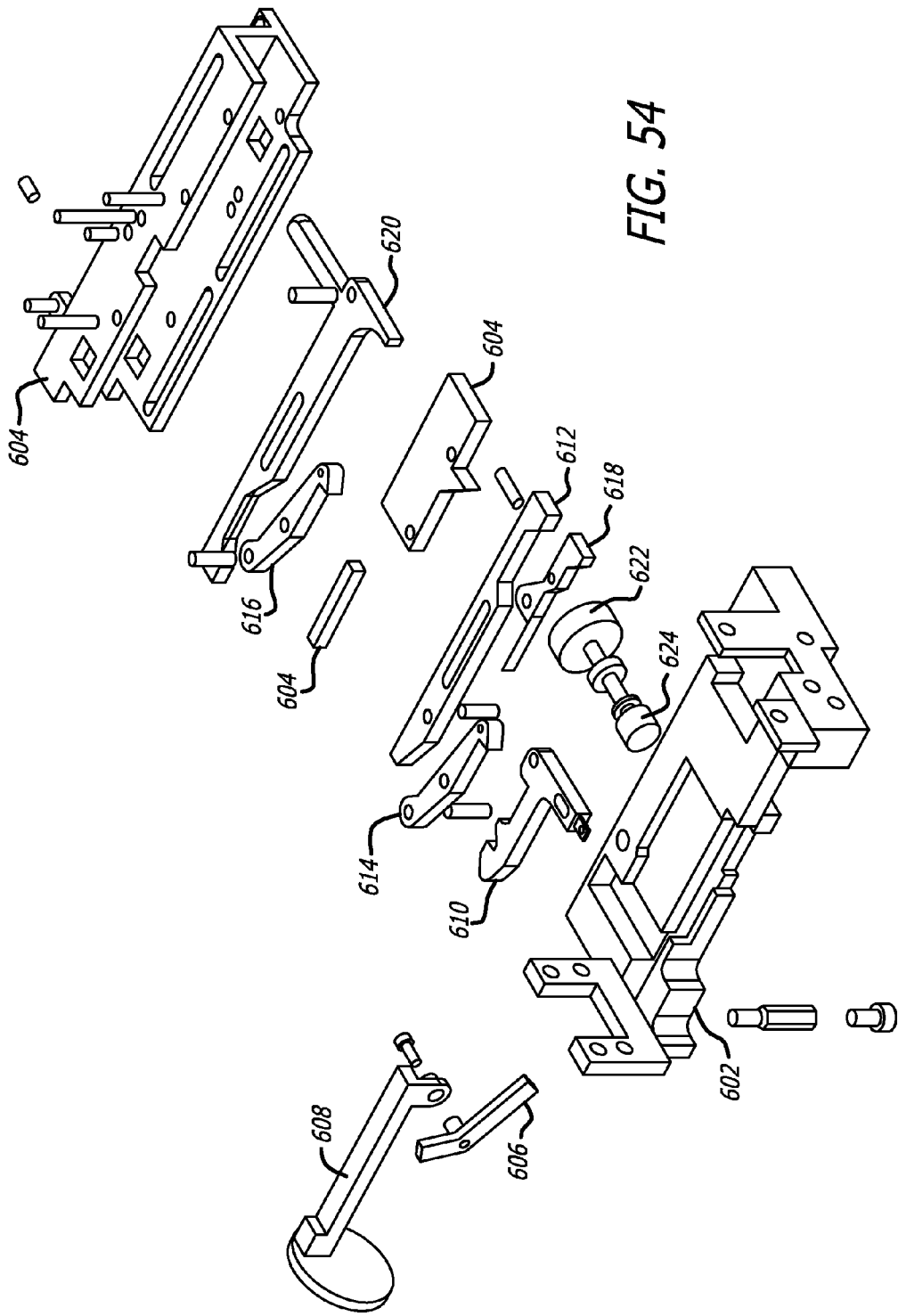
FIG. 54 is an exploded view, depicting the components of the trigger assembly of FIG. 53.

Details of an embodiment of the trigger assembly 126 are depicted in FIGS. 53 and 54. The assembly 126 includes a base 602 and a frame 604 to which other components are affixed or supported. A lever pivot 606 is rotatably attached to a proximal anchor actuator assembly 608. As described below, the lever pivot 606 is rotated through action of the lever from a first position where it locks the rear or proximal anchor actuator 608 against actuation to a second position where actuation of the proximal anchor actuator is possible. Eventual actuation of the proximal anchor actuator assembly 608 causes a deflection of a trigger 610 which releases a tripper 612 having cammed surfaces. A first pawl 614 is further provided and placed against both the camming surfaces of the tripper 612 and into recesses formed in the pusher block of the above disclosed pusher assembly. As described below, a second pawl 616 follows the action of the first pawl 614 to engage as desired the pusher block. A cutter pawl 618 is also placed into engagement with camming surfaces of the tripper 612, the cutter pawl cooperating to actuate the cutter assembly. Furthermore, the trigger assembly 126 also includes a reset lever 620 and a cutter bailout assembly 622 including a biasing spring 624, operation of which will be described below. It is to be recognized, however, that the system can be configured such that manipulation of the needle retract lever, for example, can accomplish resetting the device as well as the bailout function.

Figure 55:
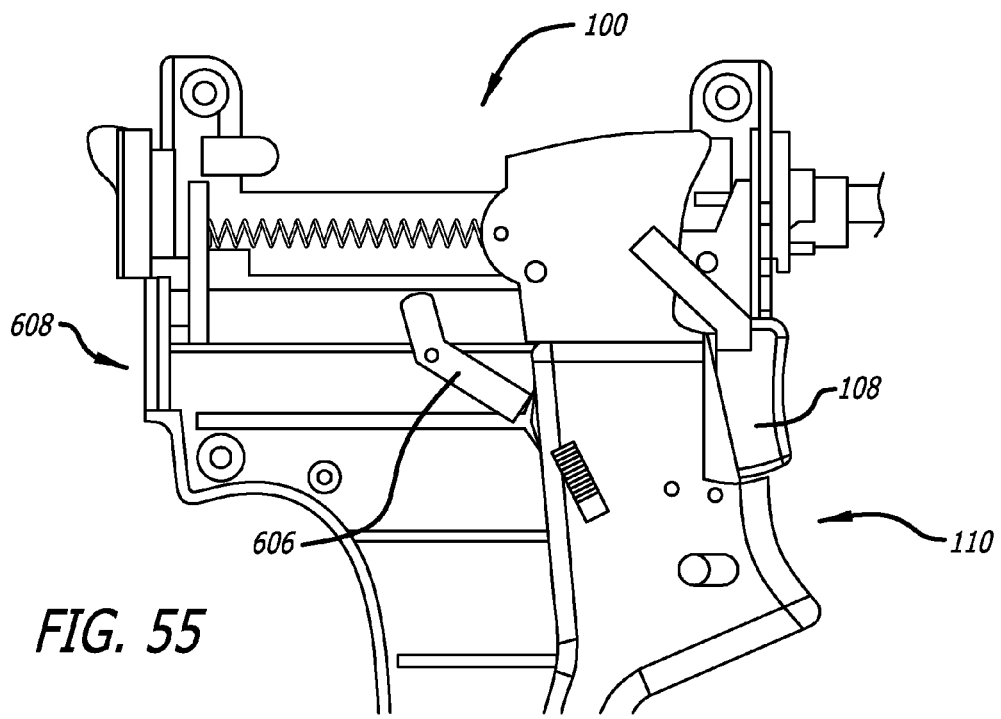
FIG. 55 is a partial cross-sectional view, depicting the delivery device prior to depression of the retraction lever.
Figure 56:
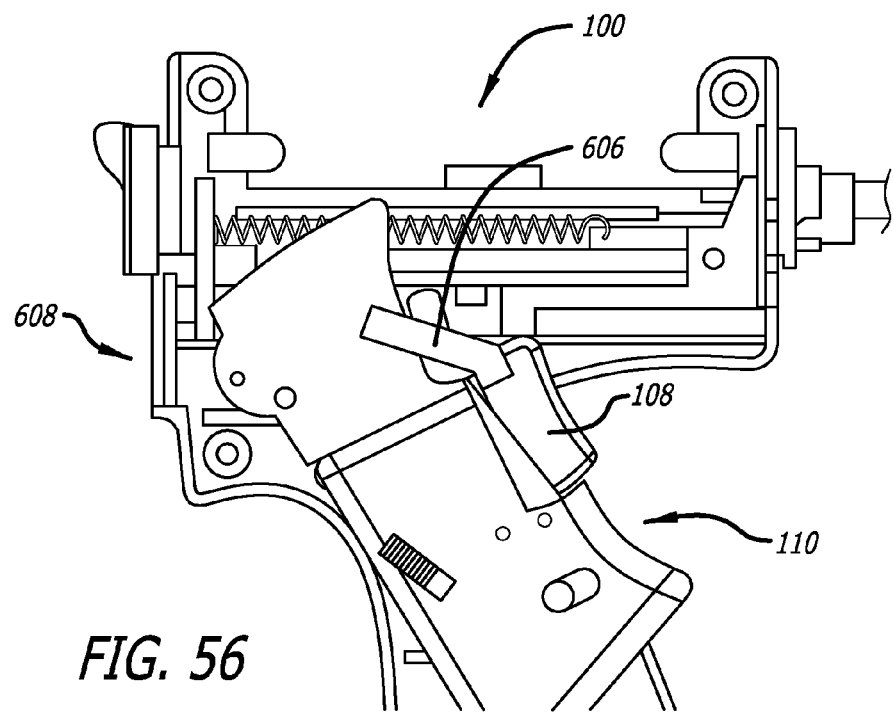
FIG. 56 is a partial cross-sectional view, depicting the device of FIG. 55 after depression of the retraction lever.
Figure 57:
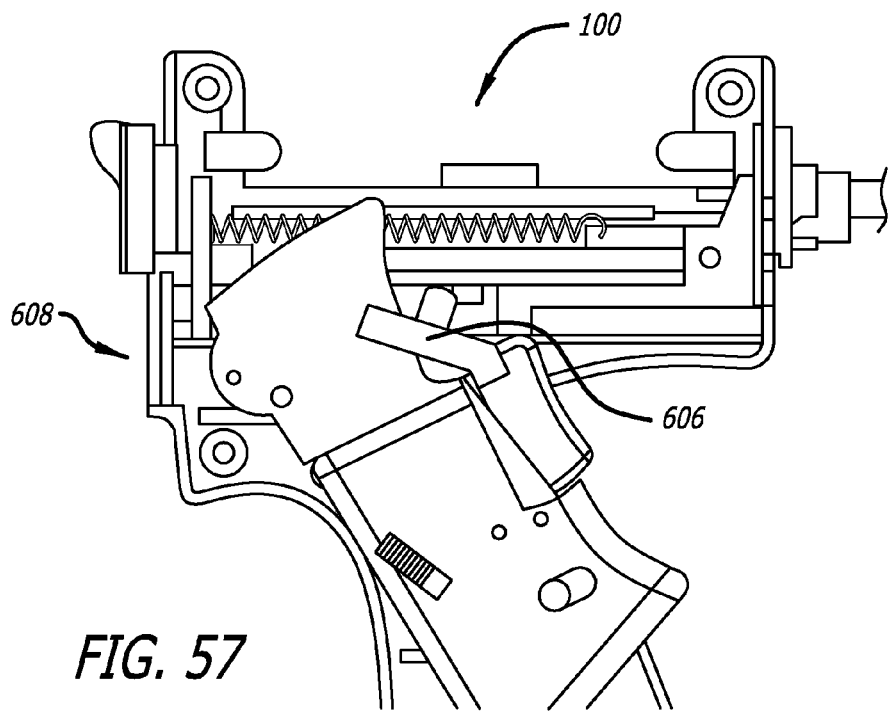
FIG. 57 is a partial cross-sectional view, depicting further action of components of the device depicted in FIG. 56.
Figure 58:
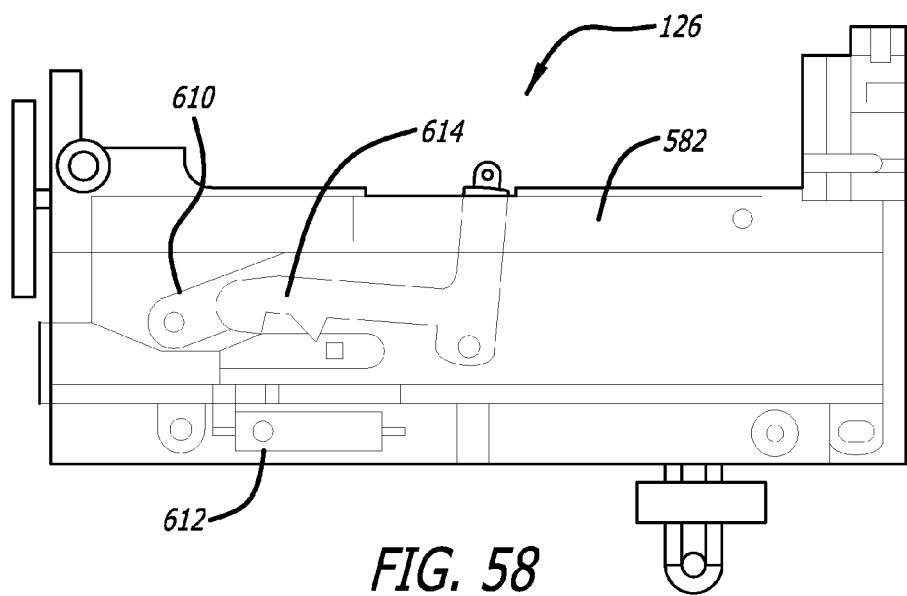
FIG. 58 is a partial cross-sectional (inferior) view, depicting action of the trigger assembly.

With reference now to FIGS. 55-58, an embodiment of the anchor delivery is shown in cross-section to illustrate locked and unlocked configurations of the trigger assembly 126. In FIG. 55, the needle actuator 108 and needle retractor lever 110 are in a non-actuated position and the lever pivot 606 is in a first position locking the button pad assembly 608 against actuation. Upon depression of the needle actuator 108 and subsequent actuation of the retraction lever 110 (See FIG. 56), the lever pivot 606 is rotated out of engagement with the proximal anchor actuator assembly 608. It is at this stage that the proximal anchor actuator 608 is unlocked and can be depressed (See FIG. 57). Once depressed, the proximal anchor actuator assembly 608 translates longitudinally to rotate the trigger 610 out of locking engagement with the tripper 612. This, in turn, initiates the action of the trigger assembly 126.

Figure 59:
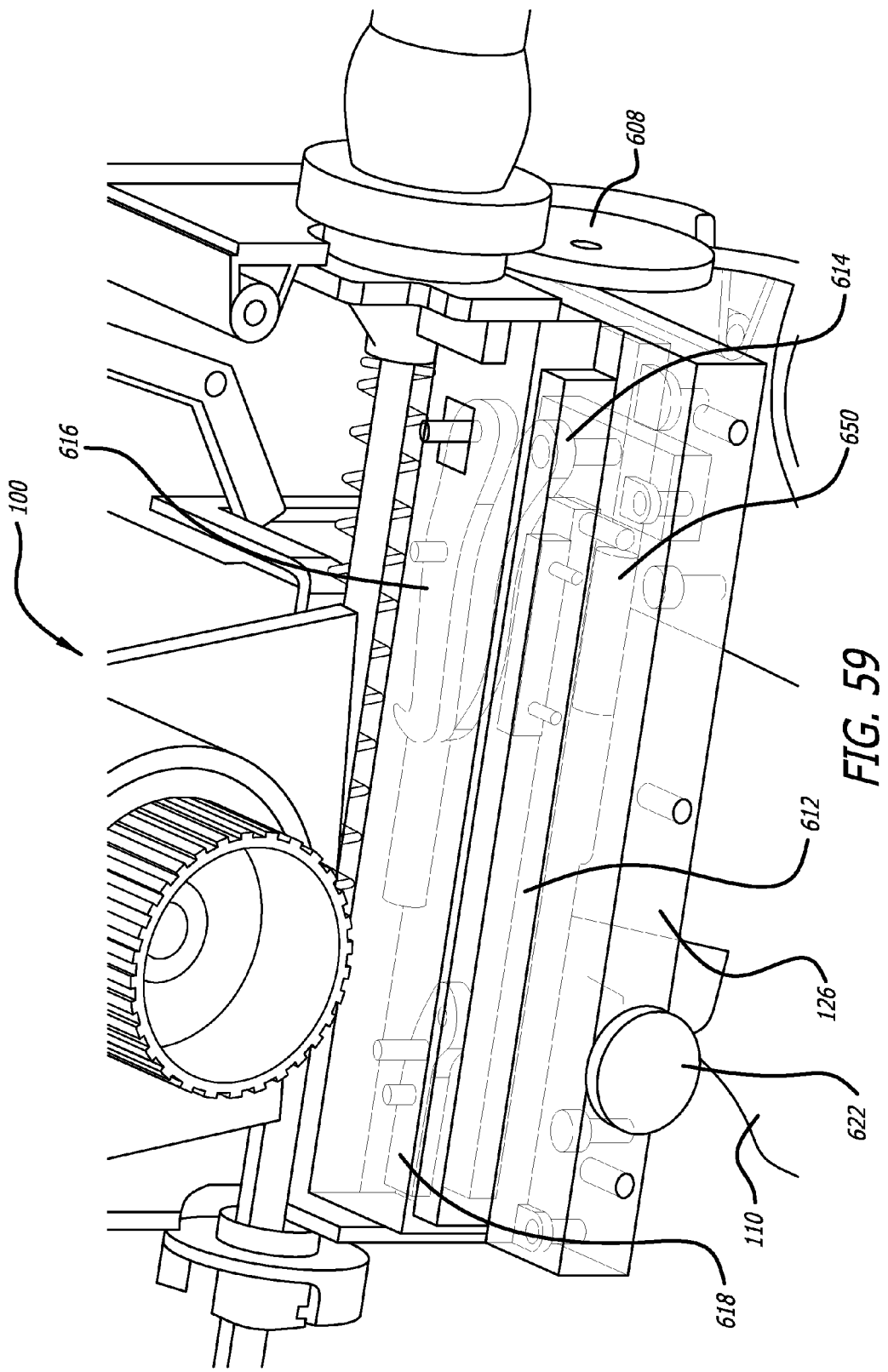
FIG. 59 is a partial cross-sectional view, depicting a delivery device readied for depression of the proximal anchor actuator.

Turning now to FIG. 59, the trigger assembly 126 is shown prior to actuation. As shown, the proximal anchor actuator 608 is readied for depression and the trigger 612 is in its longitudinally distal position. Also, the first pawl 614 is in a first position in locking engagement with the pusher 582 of the pusher assembly (See Also FIG. 58).

Figure 60:
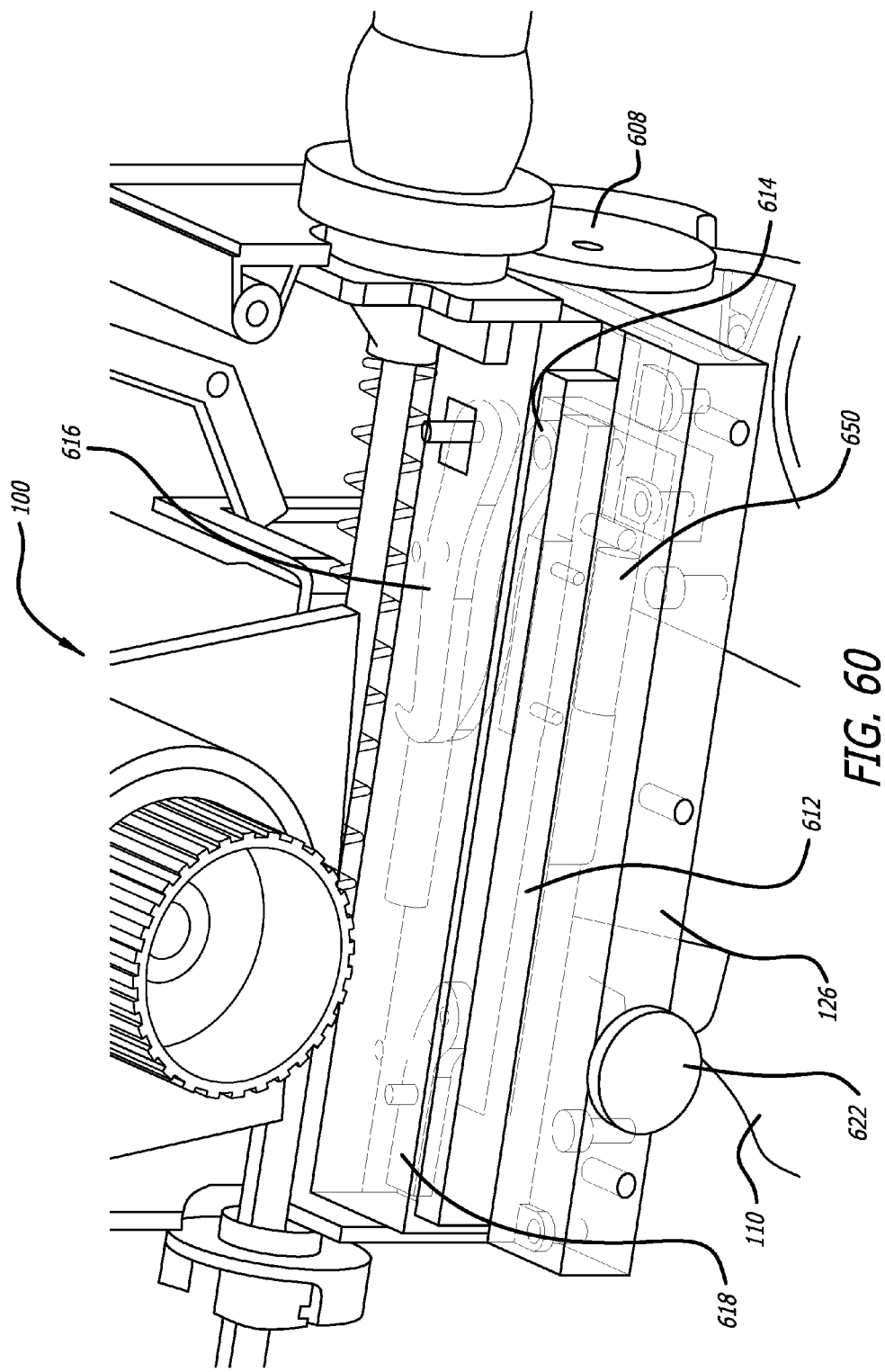
FIG. 60 is a partial cross-sectional view, depicting a depression of the proximal anchor actuator of the device shown in FIG. 59.
Figure 61:
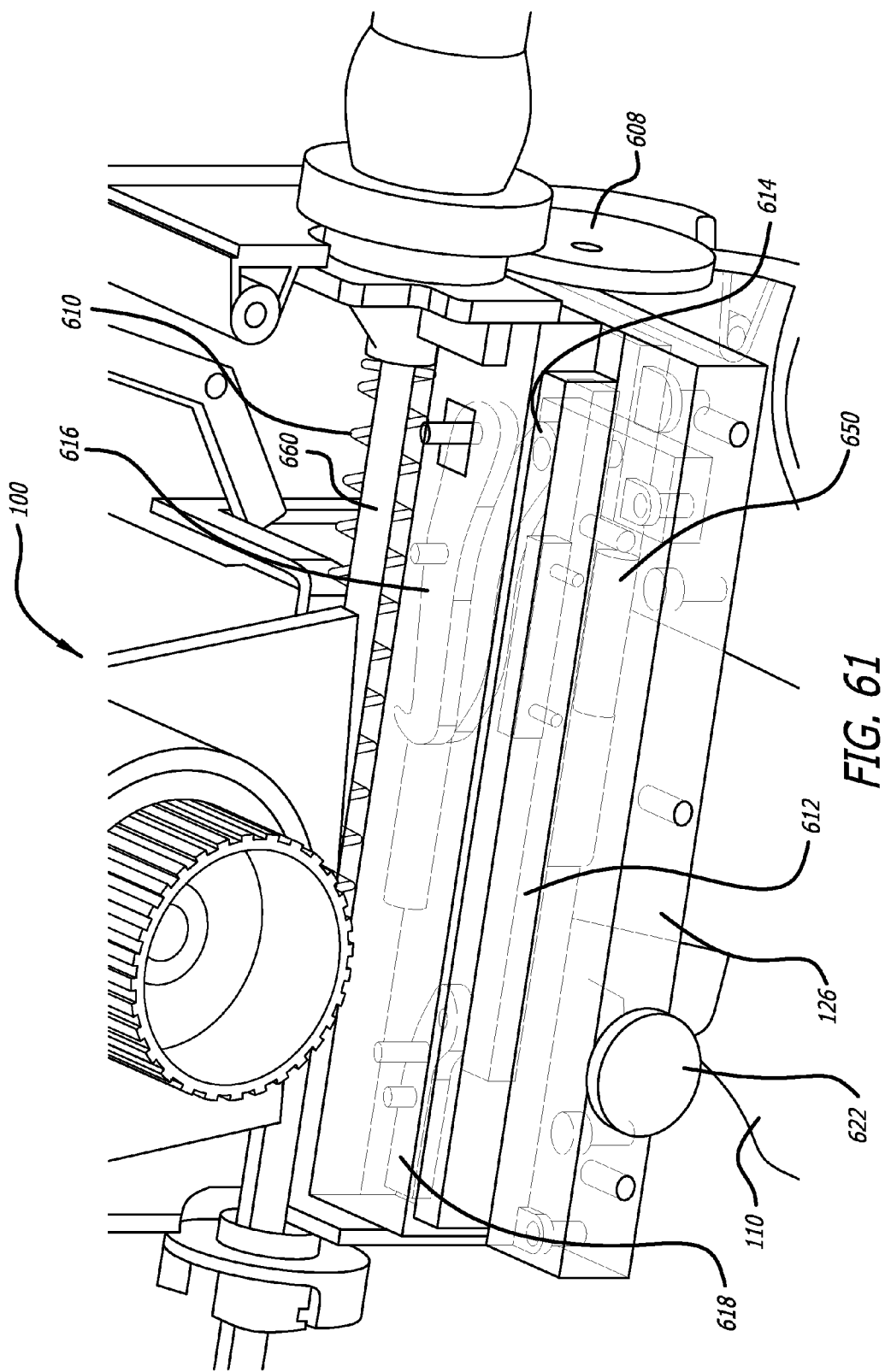
FIG. 61 is a partial cross-sectional view, depicting action of internal components of a delivery device after depression of the proximal anchor actuator.

Pressing the proximal anchor actuator assembly 608, as above stated, releases the tripper 612. Being biased by a spring assembly 650, upon release the tripper 612 moves proximally relative to an operator (See FIG. 60). As it moves proximally, camming surfaces on the tripper 612 rotate the first pawl out of engagement with the pusher 582. This action results in the release of the pusher assembly (See also FIG. 52) to move longitudinally in the distal direction. Control of the longitudinal translation of the pusher assembly is maintained by the second pawl 616 which follows movement of the first pawl, and which rotates to again lock the pusher 662.

Figure 62:
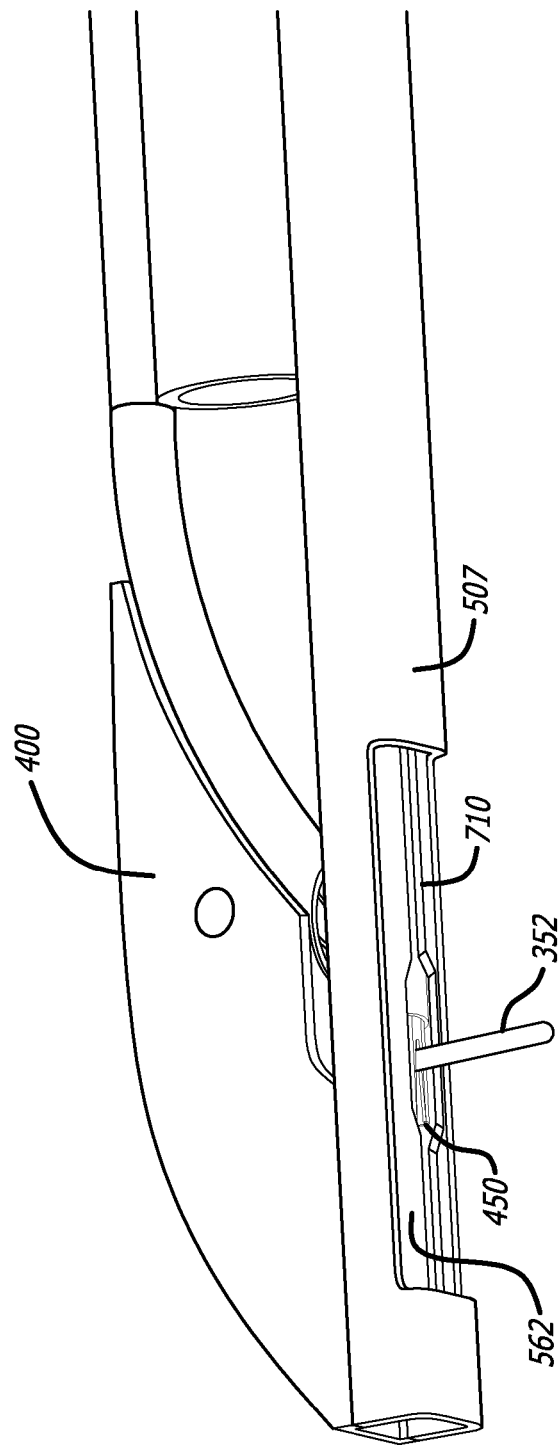
FIG. 62 is a perspective view, depicting advancement of a second anchor component into engagement with a connector.
Figure 63:
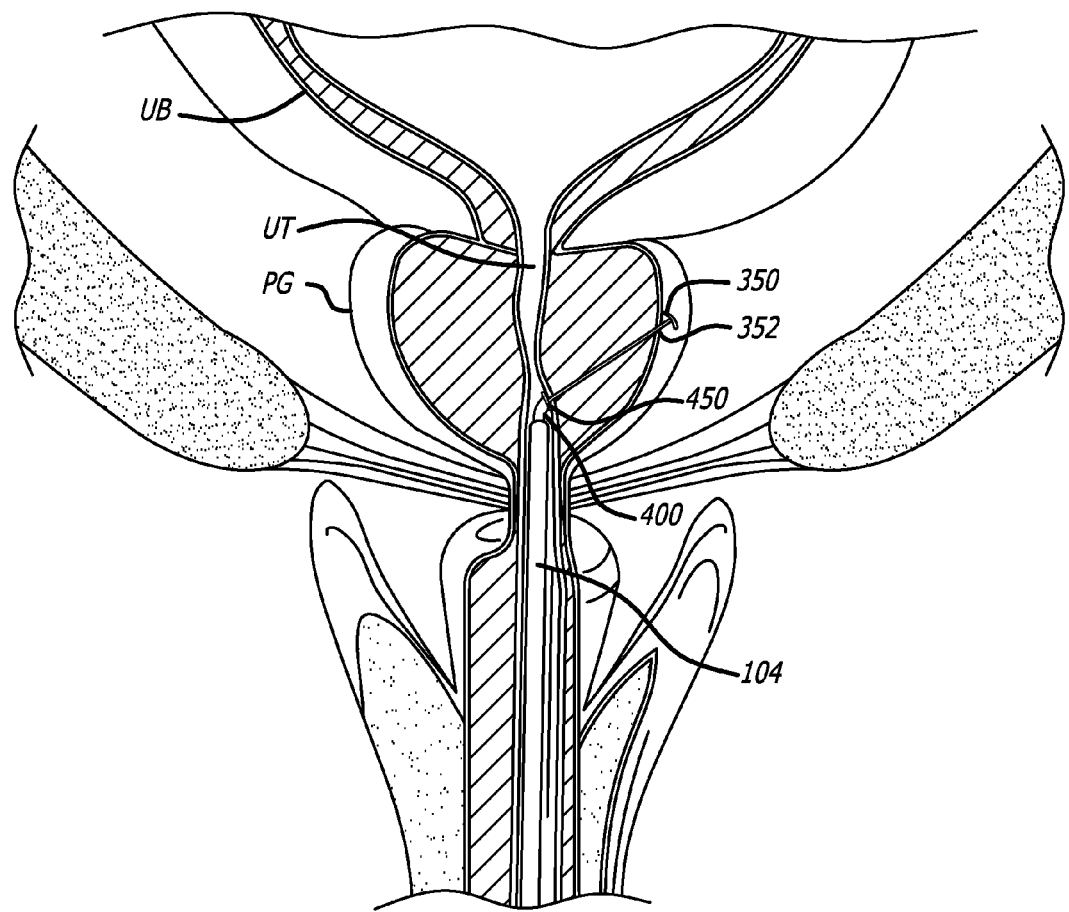
FIG. 63 is a cross-sectional view, depicting release of a second anchor component within an interventional site.
Figure 64:
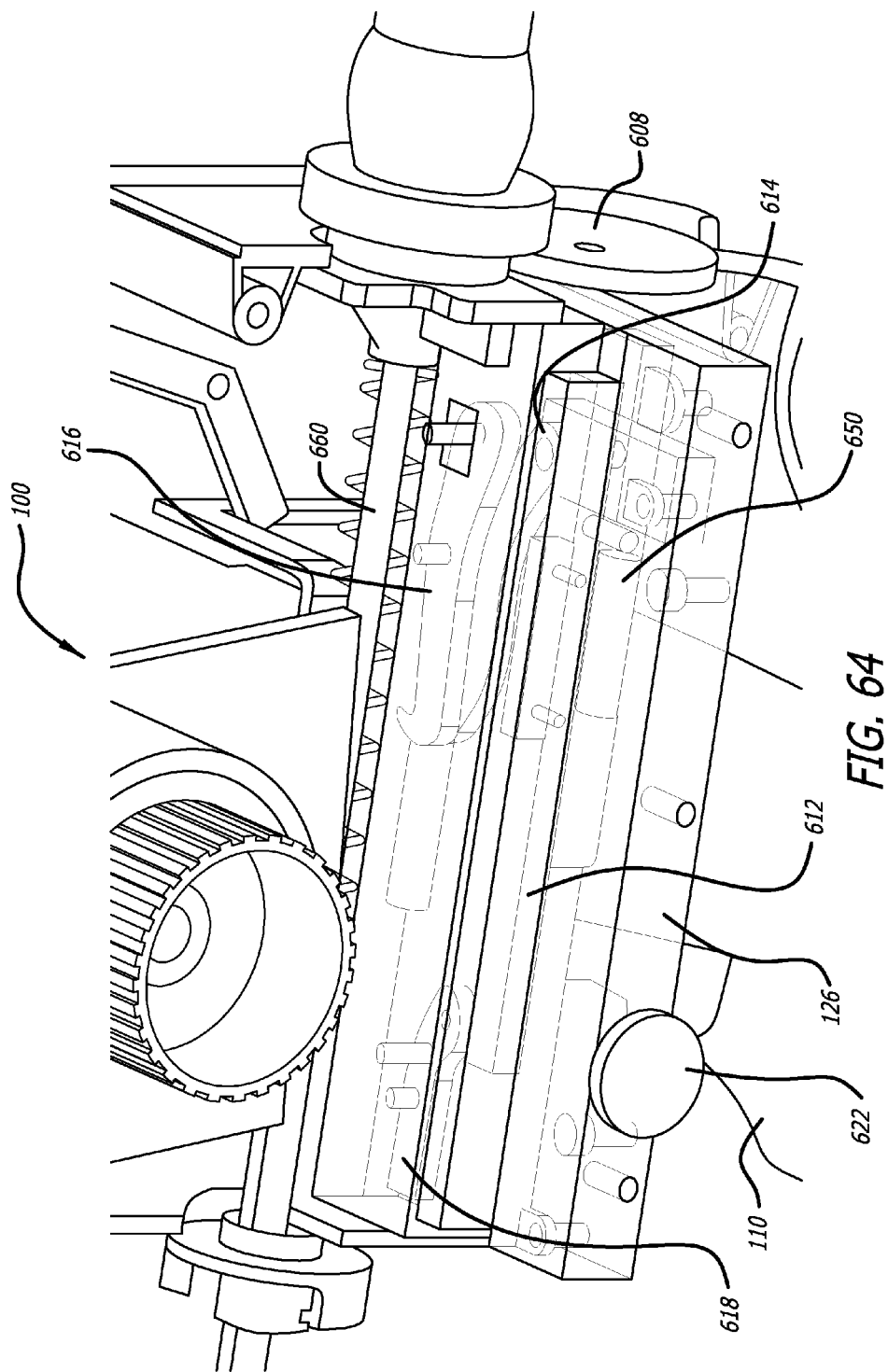
FIG. 64 is a partial cross-sectional view, depicting yet further action of components internal to the delivery device.
Figure 65:
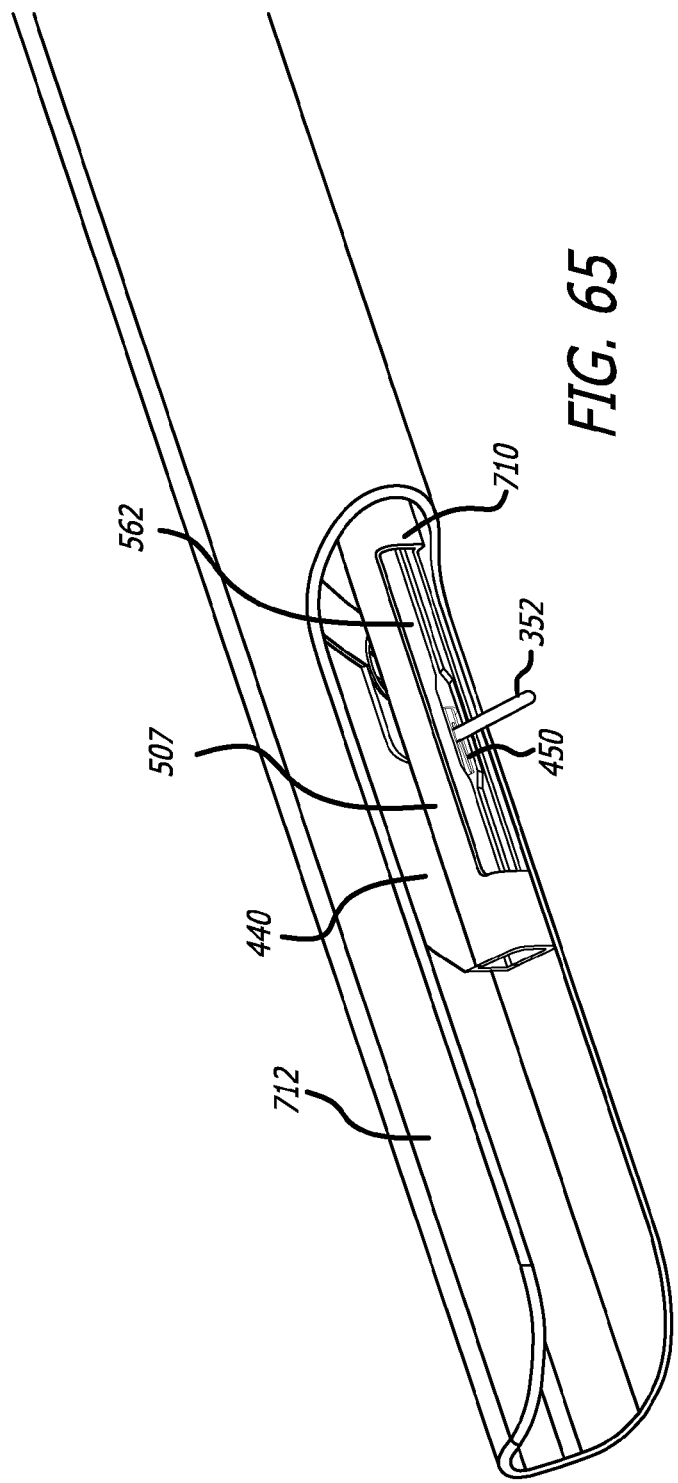
FIG. 65 is a perspective view, depicting cutting of a connector.
Figure 66:
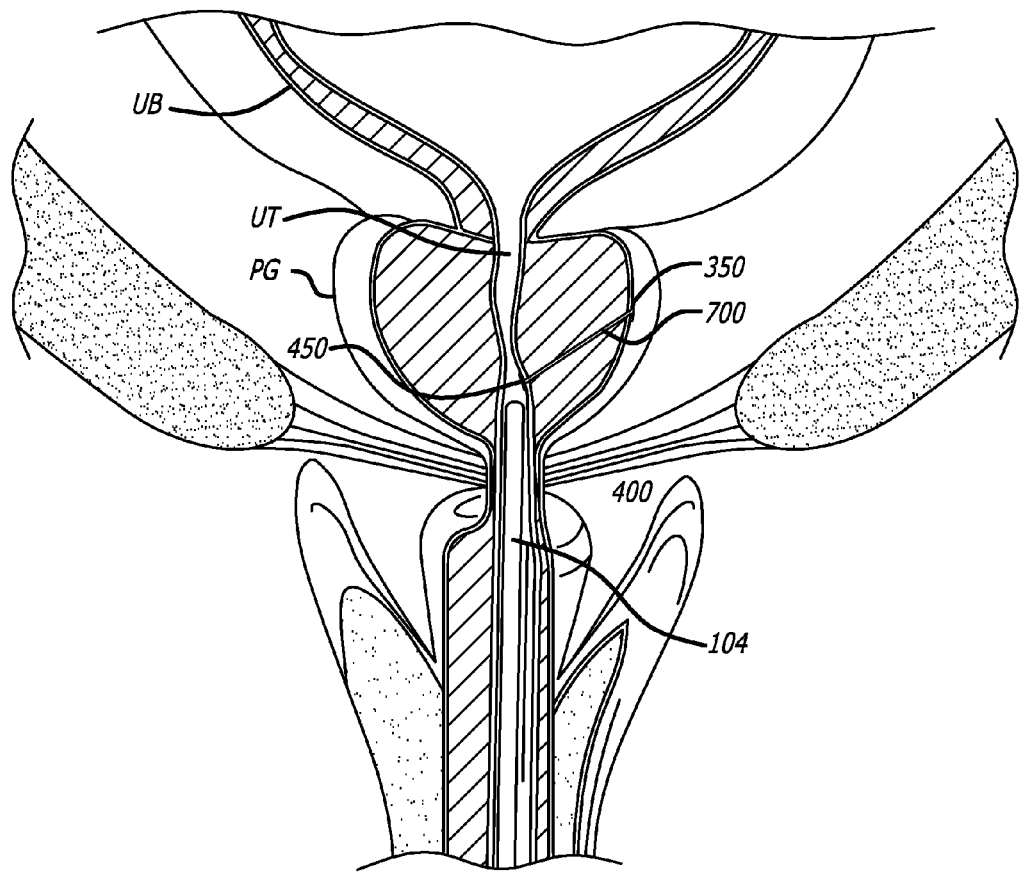
FIG. 66 is a cross-sectional view, depicting release of an assembled anchor assembly within an interventional site.
Figure 67:
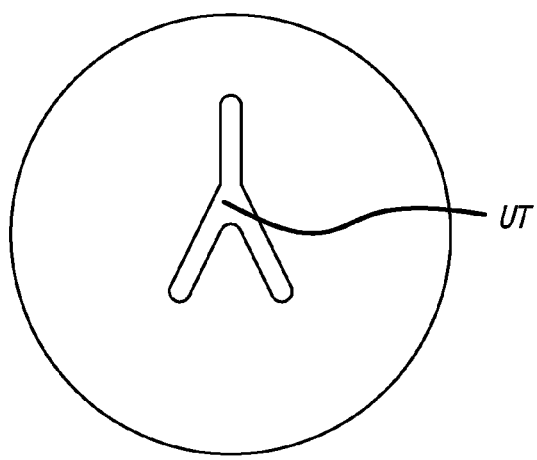
FIG. 67 is a cross-sectional view, depicting an untreated interventional site.
Figure 68:
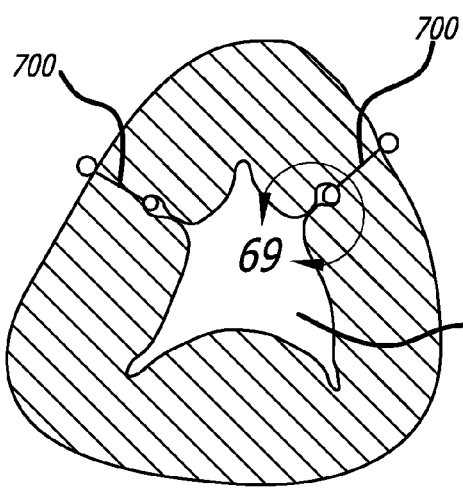
FIG. 68 is a cross-sectional view, depicting implantation of two anchor assemblies at an interventional site.
Figure 69:
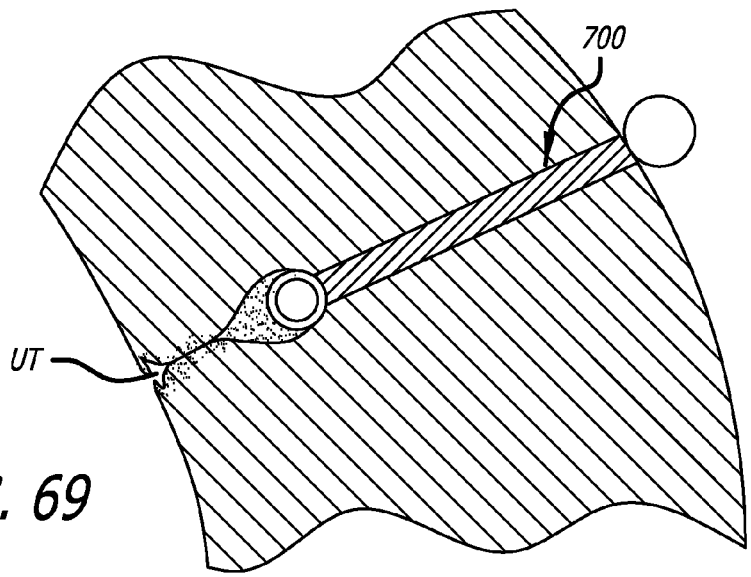
FIG. 69 is an enlarged view of a portion of FIG. 68.

Accordingly, release of the pusher assembly accomplishes advancing the pusher thereof distally resulting in advancing a second component 450 of an anchor assembly into locking engagement with a connector of an anchor assembly (See FIG. 62). Such action causes the pusher 582 to advance an anchor component 450 onto a connector (e.g., a suture) with sufficient speed and force to seat the anchor 450 with reliable retention force. Within a patient's body, as shown in FIG. 63, the anchor assembly is configured across anatomy within the interventional site. Longitudinally displaced cutter cam surfaces formed on the tripper 612 then subsequently engage the cutter pawl 618 to rotate it out of engagement with the cutter assembly (See FIGS. 50-55) to thereby allow it to be withdrawn by action of springs 660 biasing the cutter assembly (See FIG. 64). Upon withdrawal of the cutter assembly, the blade portion 570 (See FIGS. 51 and 65) thereof is brought across the connector 352 thereby severing it close to the second anchor component 450. The resultant implanted anchor assembly 700 is shown in FIGS. 65, 68 and 69. FIG. 68 depicts a partial cross-sectional view of the urethra (UT) widened due to the anchor assembly compressing the surrounding enlarged prostate tissue due to the fact that the outer capsular tissue is rather strong, non-compressible and non-displaceable and the adenoma of the prostate gland and the urethral wall are compressible and displaceable. By way of comparison, FIG. 67 depicts a partial cross-sectional view of an untreated interventional site of the urethra (UT) narrowed by the surrounding enlarged prostate tissue.

As shown in FIGS. 62 and 65, the delivery device 100 can be configured to retain and deploy multiple second anchor components 450. The anchor components 450 are placed in-line and arranged such that a single anchor component is advanced one deployed anchor length with each trigger actuation. Upon reset of the trigger assembly a next sequential anchor component is readied for deployment. In this regard, the cover 507 can be configured with a spring-like distal tab 710 which engages a slot formed in the second to most distally positioned anchor component and which facilitates maintaining proper positioning of the most distal anchor prior to deployment. The cover 507 can further be equipped with a proximal suture slot (not shown) and include an interior arranged to include at least one flat registration surface to align anchor components 450 with connector members 352 (See FIG. 62). Furthermore, the distal end of the delivery device can be equipped with a flexible/elastomer cover. This cover shields the anchor deployment space to ensure reliable anchor seating on connector and to allow for ejection of an implant from a delivery tool. In FIG. 65, the distal end of the delivery device is shown within cystoscopic sheath 712.

The second anchor component can be embodied in a slotted anchor configured to secure to a connector. The slotted proximal anchor can include a flattened-tubular back end that resembles a flattened tube in shape, with a width in lateral cross-section that is greater than its thickness. The slotted proximal anchor also includes a pair of spaced apart prongs extending from the back end of the slotted proximal anchor to the front end of the slotted proximal anchor. The spaced prongs join together at a slot inception. The prongs are shaped and sized of a configuration and of a rigidity to substantially prevent deflection of the prongs. The prongs can include inwardly facing protrusions that are configured to capture and deform the connector between the protrusions and prevent the connector from disengaging from the slotted anchor device once engaged. The mechanism of suture attachment and strength of the assembly is a combination of compression of the suture between the stiff slotted prongs of the anchor as well as disruption of the suture surface by the discreet edges of the slotted, flattened-tubular anchor. The discreet edges provide a lower contact surface area between anchor prongs and suture and focuses the compressive forces in focal points that cause the suture to conform around both internal recesses and external faces. It is also to be recognized that various further embodiments of slotted anchors or anchors forming a clip are also contemplated. In particular, various embodiments of structures which accordingly provide alternative approaches to attach to a connector can be employed. That is, the anchors can be deformable, deflectable, latching, nested, meltable and/or coiled in structure.

Accordingly, the present invention contemplates both pushing directly on anchor portions of an anchor assembly as well as pushing directly upon the connector of the anchor assembly. Moreover, as presented above, the distal or first anchor component is advanced and deployed through a needle assembly and at least one component of the proximal or second anchor component is advanced and deployed from a housing portion of the anchor deployment device. Further, both a single anchor assembly or multiple anchor assemblies can be delivered and deployed at an intervention site by the deployment device. Consequently, in the context of prostate treatment, the present invention is used for the compression of the prostate gland and the opening of the prostatic urethra, the delivering of an implant at the interventional site, and applying tension between ends of the implant. Moreover, drug delivery is both contemplated and described as a further remedy in BPH and over active bladder treatment as well as treating prostate cancer and prostatitis.

Once implanted, the anchor assembly of the present invention accomplishes desired tissue manipulation, compression or retraction as well as cooperates with the target anatomy to provide an atraumatic support structure. In one preferred embodiment, the shape and contour of the anchor assembly 700 is configured so that the assembly invaginates within target tissue, such as within natural folds formed in the urethra by the opening of the urethra lumen by the anchor assembly (See FIGS. 68-69). In fact, in situations where the anchor assembly is properly placed, wispy or pillowy tissue in the area collapses around the anchor structure. Eventually, the natural tissue can grow over the anchor assembly 700 and new cell growth occurs over time (see FIG. 69). Such cooperation with target tissue facilitates healing and avoids unwanted side effects such as calcification or infection at the interventional site.

The disclosed anchor delivery device can be configured for multiple or single use. In this regard, multiple or a single first anchor component can be loaded within the delivery device via a cartridge assembly, which is a removable and replaceable assembly. Further, multiple or a single second anchor component can be configured within the shaft assembly such as shown in FIG. 34. In this regard, the second anchor components can be lined up end to end within the shaft assembly with a proximal most second anchor component being placed into engagement with a lead end of the pusher assembly.

Additionally, after a first use, the spool assembly of the delivery device can be reset for further use through the manipulating of the reset lever 220 (See FIGS. 30-32, 36-38). An initial step in resetting the device would involve releasing the needle retraction lever 110 from its engagement with the locking mechanism 406 (See FIG. 33). Further, the trigger assembly can be reset through the actuator of the trigger reset lever 620.

It has also been observed that in certain situations there may be a need for a cutter bailout assembly 622 (See FIGS. 54, 58 and 59) after the first anchor component has been delivered within an interventional site (FIG. 35). Depression of the cutter bailout assembly 622, when needed, results in tripping the cutter pawl thereby releasing the cutter assembly and subsequently cutting a connector of an anchor assembly prior to completing assembly of the anchor. It is contemplated within the present invention the ability to retract the needle at any time including arresting a moving needle and retracting an incompletely deployed needle.

Furthermore, in addition to an intention to cooperate with natural tissue anatomy, the present invention also contemplates approaches to accelerate healing or induce scarring. Manners in which healing can be promoted can include employing abrasive materials, textured connectors, biologics and drugs.

It has been observed that placing the anchors at various desired positions within anatomy can extract the best results. For example, when treating a prostate, one portion of an anchor assembly can be placed within an urethra and a second component beyond the outer surface of the prostate. It has been found that implanting the anchor assemblies by using the distal end of the device to displace the prostate lobe on either side (while the tension spring is taking up slack in the connector after the delivery needle has been retracted) while deploying the second anchor component so that the ten o'clock and two o'clock positions (when looking along the axis of the urethra) are supported or retained, effectively holds the anatomy open and also facilitates invagination of the anchor portion within natural tissue. This is particularly true in the regions of anatomy near the bladder and the juncture at which the ejaculatory duct connects to the urethra.

Additionally, it is contemplated that all components of the anchor assembly or selected portions thereof (of any of the anchor assemblies described or contemplated), may be coated or embedded with therapeutic or diagnostic substances (e.g. drugs or therapeutic agents). Again, in the context of treating a prostate gland, the anchor assembly can be coated or imbedded with substances such as 5-alpha-reductase which cause the prostate to decrease in size. Other substances contemplated include but are not limited to phytochemicals generally, alpha-1a-adrenergic receptor blocking agents, smooth muscle relaxants, and agents that inhibit the conversion of testosterone to dihydrotestosterone. In one particular approach, the connector 95 can for example, be coated with a polymer matrix or gel coating which retains the therapeutic or diagnostic substance and facilitates accomplishing the timed release thereof. Additionally, it is contemplated that bacteriostatic coatings as well as analgesics and antibiotics for prostatitis and other chemical coatings for cancer treatment, can be applied to various portions of the anchor assemblies described herein. Such coatings can have various thicknesses or a specific thickness such that it along with the connector itself matches the profile of a cylindrical portion of an anchor member affixed to the connector. Moreover, the co-delivery of a therapeutic or diagnostic gel or other substances through the implant deployment device or another medical device (i.e. catheter), and moreover an anchor assembly including the same, is within the scope of the present invention as is radio-loading devices (such as a capsular or distal ends of implants for cancer or other treatment modalities). In one such approach, the deployment device includes a reservoir holding the gel substance and through which an anchor device can be advance to pick up a desired quantity of therapeutic or diagnostic gel substance.

It is to be recognized that the timing of the dual advancement of the needle and connector assemblies and subsequent relative motion between the assemblies is coordinated. That is, the needle assembly first provides access to an interventional site and then the connector assembly is left extending beyond a terminal end of the needle assembly through the relative motion of the needle and connector assemblies.

It is further contemplated that in certain embodiments, the anchor delivery device can include the ability to detect forces being applied thereby or other environmental conditions. Various sections of the device can include such devices and in one contemplated approach sensors can be placed along the needle assembly. In this way, an operator can detect for example, whether the needle has breached the target anatomical structure at the interventional site and the extent to which such breaching has occurred. Other sensors which can detect particular environmental features can also be employed such as blood or other chemical or constituent sensors. Moreover, one or more pressure sensors or sensors providing feedback on the state of deployment of the anchor assembly during delivery or after implantation are contemplated. For example, tension or depth feedback can be monitored by these sensors. Further, such sensors can be incorporated into the anchor assembly itself, other structure of the deployment device or in the anatomy.

Moreover, it is to be recognized that the foregoing procedure is reversible. In one approach, the connection of an anchor assembly can be severed and a proximal (or second) anchor component removed from the patient's body. For example, the physician can simply cut the connector and simultaneously remove the second anchor previously implanted for example, in the patient's urethra using electro-surgical, surgical or laser surgical devices used in performing transurethral prostate resection.

An aspect that the various embodiments of the present invention provide is the ability to deliver multiple, anchor assemblies having a customizable length and distal anchor components, each anchor assembly being implanted at a different location without having to remove the device from the patient. The various embodiments provide for variable needle depth and variable connector length for each of the multiple anchor assemblies delivered. Other aspects of the various embodiments of the present invention are load-based delivery, preferably 1 pound, of an anchor assembly, anchor assembly delivery with a device having integrated connector, (e.g. suture), cutting, and anchor assembly delivery with an endoscope in the device. The delivery device is uniquely configured to place such a load (half pound to five pounds) between spaced first anchor members as well as between or on an implanted first anchor to help ensure that the first anchor component sits firmly against a tissue plane (e.g., the outer capsule of the prostate) and is held relatively firm as the second anchor component is attached to the connector and the delivery device. In this aspect, the needle assembly acting as a penetrating member can be cooperatively connected to a mechanism which produces a desired tension between the various anchor members while the needle assembly is retracted. Moreover, this load can be accomplished between first and second implanted anchor members.

It is to be recognized that various materials are within the scope of the present invention for manufacturing the disclosed devices. Moreover, one or more components such as distal anchor, proximal anchor, connector, of the one or more anchor devices disclosed herein may be designed to be completely or partially biodegradable or biofragmentable.

Further, as stated, the devices and methods disclosed herein may be used to treat a variety of pathologies in a variety of lumens or organs comprising a cavity or a wall. Examples of such lumens or organs include, but are not limited to urethra, bowel, stomach, esophagus, trachea, bronchii, bronchial passageways, veins (e.g. for treating varicose veins or valvular insufficiency), arteries, lymphatic vessels, ureters, bladder, cardiac atria or ventricles, uterus, fallopian tubes, etc.

Finally, it is to be appreciated that the invention has been described hereabove with reference to certain examples or embodiments of the invention but that various additions, deletions, alterations and modifications may be made to those examples and embodiments without departing from the intended spirit and scope of the invention. For example, any element or attribute of one embodiment or example may be incorporated into or used with another embodiment or example, unless to do so would render the embodiment or example unpatentable or unsuitable for its intended use. Also, for example, where the steps of a method are described or listed in a particular order, the order of such steps may be changed unless to do so would render the method unpatentable or unsuitable for its intended use. All reasonable additions, deletions, modifications and alterations are to be considered equivalents of the described examples and embodiments and are to be included within the scope of the following claims.

Thus, it will be apparent from the foregoing that, while particular forms of the invention have been illustrated and described, various modifications can be made without parting from the spirit and scope of the invention.

We claim:

1. A system for treatment of body tissue, comprising:
   an anchor assembly, the anchor assembly including a first component and a second component; and
   a delivery device, the delivery device including a needle assembly, a needle deploy actuator and a retract lever;
   wherein the actuator accomplishes automated deployment of the needle assembly and the lever accomplishes manual withdrawal of the needle assembly;
   wherein the delivery device includes a needle deployment spring and actuation of the actuator results in the needle deployment spring automatically advancing the needle assembly with a force sufficient to penetrate target tissue;
   wherein actuation of the lever accomplishes manual retraction of the needle assembly without involvement of the deployment spring;
   wherein the delivery device includes a spool assembly controlling the position of the needle assembly.

2. The system of claim 1, wherein the spool assembly includes the needle deployment spring.

3. The system of claim 2, wherein the delivery device includes a cartridge assembly, the cartridge assembly housing one anchor component.

4. The system of claim 3, wherein the cartridge assembly is replaceable.

5. The system of claim 4, wherein the cartridge assembly is configured to releasably engage the spool assembly.

6. The system of claim 5, wherein the cartridge assembly is configured to feed the one anchor component within the needle assembly.

7. The system of claim 6, wherein the cartridge assembly includes a spring.

8. The system of claim 7, wherein a clutch is provided to disassociate the cartridge assembly from at least a portion of the spool assembly.

9. The system of claim 8, wherein the spring is configured to apply a tension on the one anchor component.

10. The system of claim 9, wherein the delivery device includes a trigger assembly.

11. The system of claim 10, wherein the trigger assembly is configured to effect assembly of the anchor assembly.

12. The system of claim 11, wherein the trigger assembly controls severing of a third component of the anchor assembly.

13. The system of claim 12, wherein the delivery device includes a bail-out assembly configured to sever the third component of the anchor assembly.

14. The system of claim 13, wherein the delivery device includes a first reset lever configured to reset the needle spool assembly.

15. The system of claim 14, wherein the delivery device includes a second reset lever configured to reset the trigger assembly.

16. A system for treatment of body tissue, comprising:
    an anchor assembly; and
    a delivery device including a needle assembly, a spool assembly, a trigger assembly, a first actuator, a second actuator and a third actuator;
    wherein actuation of the first actuator advances the needle assembly and a portion of the anchor assembly, actuation of the second actuator withdraws the needle assembly and actuation of the third actuator accomplishes assembly of the anchor assembly.

17. The system of claim 16, wherein the delivery device includes a first reset lever and a second reset lever, wherein the first reset lever resets the spool assembly and the second reset lever resets the trigger assembly.

18. The system of claim 17, wherein the delivery device includes a bail-out assembly and actuation of the bail-out assembly accomplishes severing a component of the anchor assembly.

19. The system of claim 16, wherein the delivery device includes a lock-out assembly which locks the lever until after depression of the first actuator.

20. The system of claim 16, wherein the delivery device includes a locking mechanism which locks the lever in a depressed condition.

21. The system of claim 16, wherein the delivery device includes a first actuator lock which prevents accidental needle deployment.

22. The system of claim 16, wherein the delivery device includes structure to avoid premature deployment of the third actuator until the second actuator is fully depressed.

23. The system of claim 16, wherein a needle moves along a curved trajectory within the needle assembly.

* * * * *